(12) United States Patent
Winters et al.

(10) Patent No.: US 11,053,139 B2
(45) Date of Patent: Jul. 6, 2021

(54) **METHODS AND USES OF ENCAPSULATED EXUDATES AND DRIED *EUGLENA* BIOMASS FOR BINDING METAL**

(71) Applicant: NOBLEGEN INC., Peterborough (CA)

(72) Inventors: Cameron Winters, Omemee (CA); Vaughn Mangal, Ajax (CA); Ainsely Lewis, Peterborough (CA); Celine Gueguen, Sherbrooke (CA); Adam Noble, Peterborough (CA); Adam Long, Peterborough (CA)

(73) Assignee: NOBLEGEN INC., Peterborough (CA)

( * ) Notice: Subject to any disclaimer, the term of this patent is extended or adjusted under 35 U.S.C. 154(b) by 0 days.

(21) Appl. No.: 16/603,361

(22) PCT Filed: Apr. 6, 2018

(86) PCT No.: PCT/CA2018/050431
§ 371 (c)(1),
(2) Date: Oct. 7, 2019

(87) PCT Pub. No.: WO2018/184120
PCT Pub. Date: Oct. 11, 2018

(65) Prior Publication Data
US 2020/0140289 A1 May 7, 2020

Related U.S. Application Data

(60) Provisional application No. 62/482,952, filed on Apr. 7, 2017.

(51) Int. Cl.
*C02F 1/28* (2006.01)
*B01J 20/24* (2006.01)
(Continued)

(52) U.S. Cl.
CPC .............. *C02F 1/286* (2013.01); *B01J 20/24* (2013.01); *B01J 20/3208* (2013.01);
(Continued)

(58) Field of Classification Search
CPC .... C02F 1/286; C02F 3/348; C02F 2101/103; C02F 2101/106; C02F 2101/203;
(Continued)

(56) References Cited

U.S. PATENT DOCUMENTS 8,308,944 B2   11/2012  Horst
8,663,953 B2    3/2014  Behrens et al.
(Continued)

FOREIGN PATENT DOCUMENTS

CA          2103495 A1    5/1994
CA          2166717 A1    1/1995
(Continued)

OTHER PUBLICATIONS

100th Canadian Chemistry Conference and Exhibition (CSC 2017); see p. 11, "17:20"; Technical Program shows title only, May 28, 2017.
(Continued)

*Primary Examiner* — Fred Prince
(74) *Attorney, Agent, or Firm* — Troutman Pepper Hamilton Sanders LLP

(57) ABSTRACT

A method of binding a target metal in solution. The method of binding a target metal comprises contacting a solution containing i) a target metal with ii) an encapsulated exudate of a culture of algal flagellate, or a fraction thereof; or an encapsulated dried *Euglena* biomass or a fraction thereof, to form a complex between the target metal, and the encapsulated exudate or fraction thereof, or the encapsulated dried *Euglena* biomass or the fraction thereof; and optionally separating the complex from the solution. The disclosure
(Continued)

also relates to a biosorbent element, as well as methods of using same in binding a metal in solution.

21 Claims, 34 Drawing Sheets

(51) Int. Cl.
    *B01J 20/32*     (2006.01)
    *C02F 3/34*     (2006.01)
    *C12N 11/08*     (2020.01)
    *C12N 11/10*     (2006.01)
    *C02F 101/10*     (2006.01)
    *C02F 101/20*     (2006.01)
    *C02F 101/22*     (2006.01)
    *C02F 103/10*     (2006.01)

(52) U.S. Cl.
    CPC ....... *B01J 20/3265* (2013.01); *B01J 20/3293* (2013.01); *C02F 3/348* (2013.01); *C12N 11/08* (2013.01); *C12N 11/10* (2013.01); *B01J 2220/4843* (2013.01); *C02F 2101/103* (2013.01); *C02F 2101/106* (2013.01); *C02F 2101/203* (2013.01); *C02F 2101/206* (2013.01); *C02F 2101/22* (2013.01); *C02F 2103/10* (2013.01)

(58) Field of Classification Search
    CPC ............ C02F 2101/206; C02F 2101/22; C02F 2103/10; C02F 2101/20; C02F 3/34; B01J 20/24; B01J 20/3208; B01J 20/3265; B01J 20/3293; B01J 2220/4843; B01J 20/3268; C12N 11/08; C12N 11/10; B01D 15/00
    USPC ..... 210/602, 631, 912, 913, 914; 435/257.1, 435/257.3, 257.4, 257.5, 257.6
    See application file for complete search history.

(56) References Cited

U.S. PATENT DOCUMENTS

| | | | |
|---|---|---|---|
| 8,951,773 | B2 | 2/2015 | Kato et al. |
| 9,045,785 | B2 | 6/2015 | Pfeifer, III et al. |
| 9,249,434 | B2 | 2/2016 | Behrens et al. |
| 9,457,108 | B2 | 10/2016 | Schaap et al. |
| 2008/0197075 | A1 | 8/2008 | Musale et al. |
| 2010/0176065 | A1 | 7/2010 | Looney et al. |
| 2011/0153213 | A1 | 6/2011 | Buchanan |
| 2014/0242676 | A1* | 8/2014 | Abdel-Fattah ......... C12N 11/04 435/257.1 |
| 2015/0275166 | A1 | 10/2015 | Feris et al. |
| 2016/0281021 | A1* | 9/2016 | Schiff-Deb .......... C10M 159/02 |
| 2017/0327427 | A1 | 11/2017 | Blaney et al. |
| 2019/0210898 | A1 | 7/2019 | Gueguen et al. |
| 2020/0407252 | A1 | 12/2020 | Gueguen et al. |

FOREIGN PATENT DOCUMENTS

| | | |
|---|---|---|
| CN | 107673483 A | 2/2018 |
| DE | 3713882 A1 | 11/1988 |
| DE | 102010001907 A1 | 8/2011 |
| EP | 0288917 B1 | 9/1992 |
| EP | 1706500 B1 | 9/2010 |
| GB | 1395462 A | 5/1975 |
| WO | 2012151673 A1 | 11/2012 |
| WO | 2013138899 A1 | 9/2013 |
| WO | 2018032115 A1 | 2/2018 |
| WO | 2018184120 A1 | 10/2018 |

OTHER PUBLICATIONS

Abdel-Aal et al., 2015. Successive solvent extraction and GC-MS analysis for the evaluation of the phytochemical constituents of the filamentous green alga Spirogyra longata. The Egyptian Journal of Aquatic Research. 41(3): 233-46.

Aiken et al.; Dissolved Organic Matter in the Florida Everglades: Implications for Ecosystem Restoration. Environ. Sci. Technol. 2011, 41 (1), 271-248.

Aluwihare et al., 1997. A major biopolymeric components to DOC in surface sea water. Letters to Nature 387(8): p. 166-169.

Amon et al.; Photochemical and microbial consumption of dissolved organic carbon and dissolved oxygen in the Amazon River System. Geochimica. Cosmochim. Acta. 1996, 60 (10), 41-51.

Baars et al., 2014. ChelomEx: Isotope-assisted discovery of metal chelates in complex media using high-resolution LC-MS. Analytical Chemistry. 86(22): p. 11298-11305.

Baba et al., 2013. Biosynthesis of Lipids and Hydrocarbons in Algae, Photosynthesis: Agricultural and Biological Sciences. ISBN: 978-953-51-1161-0.

Bagwell et al., 2014. A diverse assemblage of indole- 3-acetic acid producing bacteria associated with unicellular green algae. Applied Biochemistry and Biotechnology. 173(8): 1977-84.

Balch J et al.; Effects of Molecular Weight on the Diffusion Coefficient of Aquatic Dissolved Organic Matter and Humic Substances. Chemosphere. 2015, 119, 498-503.

Barkay T. et al., "Effects of Dissolved Organic Carbon and Salinity on Bioavailability of Mercury", App. Environ. Micro.1997, 63 (11), 4267-4273.

Bauersachs. 2010. (Thesis) Development and application of proxies for past cyanobacterial N2 fixation.

Benoit et al.; Constants for Mercury Binding by Dissolved Organic Matter Isolates from the Florida Everglades. Geochim. Cosmochim. Acta. 2001, 65 (24), 4445-4451.

Bertrand, S.; Siderophore Base—The WebData Base of Microbial Siderophores. 2014.

Bronk et al., 2007. DON as a source of bioavailable nitrogen for phytoplankton. Biogeosciences. 4: p. 283-296.

Cabaniss S.E. et al., "A stochastic model for the synthesis and degradation of natural organic matter. Part I. Data structures and reaction kinetics", Biogeochem. 2005, 76, 319-347.

Chen, H., et al., Identification of Mercury and Dissolved Organic Matter Complexes Using Ultrahigh Resolution Mass Spectrometry. Environ. Sci. Technol. Lett., 2017, 4, 59-65.

Chiasson-Gould S.A. et al., "Dissolved Organic Matter Kinetically Controls Mercury Bioavailability", Environ. Sci. Technol. 2014, 48, 3153-3161.

Choi et al., 1987. Lipid content and fatty acid composition of green algae Scenedesmus obliquus grown in a constant cell density apparatus. Food Biotechnology. I (1): 117-28.

Cole et al.; Differential support of lake food webs by three types of ten-estrial carbon. Ecolo. Lett. 2006, 9 (5), 558-568.

Cortez-Rocha et al., 2002. Effect of extrusion processing on fumonisin B(I) and hydrolyzed fumonisin B(I) in contaminated alkali-cooked com. Bull Environ Contam Toxicol. 69(4): p. 471-8.

Cory et al.; Singlet Oxygen in the Coupled Photochemical and Biochemical Oxidation of Dissolved Organic Matter. Environ. Sci. Technol. 2010, 44, 3683-3689.

Cuss et al.; Impacts of Microbial Activity on the Optical and Copper-Binding Properties of Leaf-Litter Leachate. Front. Microbial. 2012, 3 (166), 1-10.

D' Andrilli et al.; Characterization of IHSS Pony Lake fulvic acid dissolved organic matter by electrospray ionization Fourier transform ion cyclotron resonance mass spectrometry and fluorescence spectroscopy. Org. Geochem. 2013, 65, 19-28.

Diez et al., 2016. Role of Settling Particles on Mercury Methylation in the Oxic Water Colunm of Freshwater Systems. Environmental Science & Technology. 50(21): p. 11672-11679.

Doran et al., A computer program to simplify analysis of mass scan data of organometallic compounds from high-resolution mass spectrometers. Rap. Comm. Mass Spec., 2016, 30, 2561-67.

Drexel et al.; Mercury (II) sorption to two Florida Everglades peats: evidence for strong and weak binding and competition by dissolved organic matter released from the peat. Environ. Sci. Technol.2002, 36 (19), 4058-4064.

(56) References Cited

OTHER PUBLICATIONS

Driscoll et al.; Mercury as a Global Pollutant: Sources,Pathways and Effects. Environ Sci. Technol. 2013, 47, 4967-4983.

Duong et al.; 2015. High protein- and high lipid-producing microalgae from northern Australia as potential feedstock for animal feed and biodiesel. Frontiers in Bioengineering & Biotechnology. 3(53): p. 1-7.

Dupont et al., 2004. Diurnal cycling of GSH in marine phytoplankton: Field and culture studies. Limnology and Oceanography. 49( 4): p. 991-996.

Everall et al., 1997. The identification and signifigance of chemicals released from decomposing barley straw during reservoir algal control. Water Research. 31(3): p. 614-620.

Freire-Nordi, CS et al., "The metal binding capacity of Anabaena spiroides extracellular polysaccharide: an EPR study.", Process Biochemistry 40 (2005): 2215-2224.

Gonzalez-Davila, M et al., "Binding of Cu(II) to the Surface and Exudates of the Alga Dunaliella tertiolecta in Seawater.", Environmental Science & Technology 29 (1995): 289-301.

Graham et al.; Dissolved Organic Matter Enhances Microbial Mercury Methylation Under Sulfidic Conditions. Environ Sci. Technol. 2012, 46, 2715-2723.

Greene, "Removal of heavy metal ions from contaminated water by Chlorella vulgaris", 29th Annual New Mexico Water Conference Proceedings, WRRI Report No. 181, Jul. 1984.

Haitzer et al., 2002. Binding of Hg to DOM the role of the Hg DOM ratio. Environmental Science & Technology. 36: p. 3564-3570.

Hammer et al.; PAST: Paleontological Statistics Software Package for Education and Data Analysis. Palaeontol. Electron. 2001, 4 (1), 9.

Han et al.; 2008. Towards high-throughput metabolomics using ultrahigh-field Fourier transform ion cyclotron resonance mass spectrometry. Metabolomics. 4(2): p. 128-140.

Hasterberg et al.; Bonding of Hg (II) to reduced organic sulfur in humic acid as affected by S/Hg ratio. Environ. Sci. Technol. 2001, 35 (13), 2741-2745.

Hernes et al., 2007. Fractionation of lignin during leaching and sorption and implications for organic matter "freshness". Geophysical Research Letters. 34(17): p. 1-6.

Hider, R.C. et al., "Chemistry and biology of siderophores", Natural Product Reports. 27(5): p. 637-57, 2009.

Holguin at al., 2013. Characterization of microalgal lipid feedstock by direct-infusion FT-ICR mass spectrometry. Algal Research. 2(1): p. 43-50.

Hopkinson et al.; Terrestrial inputs of organic matter to Coastal Ecosystems: An Intercomparison of Chemical Characteristics and Bioavailability. Biogeochem. 1998, 43, 211-234.

Hughes et al., 1998. The thiol oxireductase ERp57 is a component of the MHC class I peptide-loading complex. Current Biology. 8(12):p. 709-713.

Johnstone et al., 2015. Beyond iron: non-classical biological functions of bacterial siderophores. Dalton Transactions. 44(14): p. 6320-6339.

Kanehisa et al., 2000. KEGG-Kyoto Encyclopedia of Genes and Genomes. Nucleic Acids Research. 28(1): p. 27-30.

Kaplan, D et al., "Chelating properties of extracellular polysaccharides from *Chlorella* spp.", Applied and Environmental Microbiology 53 (1987): 2953-2956.

Kim et al.; Graphical Method dor Analysis of Ultrahigh-Resolution Broadband Mass Spectra of natural Organic Matter, the Van Krevelen Diagram. Anal. Chem. 2003, 75, 5336-5344.

Koch et al.; From mass to structure: An aromaticity Index for High-Resolution Mass Data of Natural Organic Matter. Rap. Comm. Mass. Spec. 2006, 20, 926-932.

Koukal, B et al., "Effect of Pseudokirchneriella subcapitata (Chlorophyceae) exudates on metal toxicity and colloid aggregation.", Water Research 41 (2007): 63-70. [Abstract].

Kumar et al., 2015. Green synthesis and characterization of silver nanoparticles using Andean blackberry fruit extract. Saudi Journal of Biological Sciences. 24(1):45-50.

European Extended Search Report for European Patent Application No. 17840680.7 dated Jan. 7, 2020.

International Search Report and Written Opinion for PCT/CA2018/ 050431 dated Jul. 12, 2018.

Miller et al., Influence of Dissolved Organic Matter on the Complexation of Mercury Under Sulfidic Conditions, (2007), Environmental Toxicology and Chemistry, vol. 26, No. 4, p. 624-633.

Dieguez et al., Influence of dissolved organic matter character on mercury incorporation by planktonic organisms: An experimental study using oligotrophic water from Patagonian lakes, (2013), Journal of Environmental Sciences, pp. 1980-1991.

Kurepa et al., 2014. Direct isolation of flavonoids from plants using ultra-small anatase TiO2 nanoparticles. The Plant Journal. 77(3):443-53.

Lancelot, C. 1984. Extracellular Release of Small and Large Molecules by P hytoplankton in the Southers Bight of the North Sea. Estuaries, Coastal & Shelf Science. 18: p. 65-77.

Le Faucheur, S. et al. "Interactions between mercury and phytoplankton: speciation, bioavailability, and internal handling", Environmental Toxicology & Chemistry. 33(6): p. 1211-24, 2014.

Leclerc, M. et al, "Relationship between Extracellular Low-Molecular-Weight Thiols and Mercury Species in Natural Lake Periphytic Biofilms", Environmental Science & Technology.49(13): p. 7709-16, 2015.

Lehnherr et al.; 2011. Methylation of inorganic mercury in polar marine waters. Nat Geosci. 4:298-302.

Lemire et al.; Antimicrobial activity of Metals: Mechanism, Molecular Targets and Applications. Nat. Rev. Microbial 2016, 11, 371-384.

Levy, J et al., "Using diffusive gradients in thin films to probe the kinetics of metal interaction with algal exudates", Environmental Chemistry 8 (2011): 517-524.

Ma et al.; Mercury (II) Adsorption on Three Contrasting Chinese Soils Treated with Two Sources of Dissolved Organic Matter: II. Spectroscopic Characterization. Soil Sed. Cont.2015, 24, 719-730.

Malik, D. "Algal biomass as adsorbents for heavy metal sorption from aqueous solutions." Loughborough University Institutional Repository. Doctoral Thesis. 1999.

Mangal et al., Molecular characterization of phytoplankton dissolved organic matter (DOM) and sulfur components using high resolution Orbitrap Mass Spectrometry. Anal. Bioanal. Chem. 2016, 408 (7), 1891-1900.

Mangal et al.; Examining concentrations and molecular weights of thiols in microorganism cultures and in Churchill River (Manitoba) using a fluorescent-labeling method coupled to asymmetrical flow field-flow fractionation. Anal. Bioanal. Chem. 2015, 407, 4305-4313.

Mangal, V., "Assessing cadmium and vanadium accumulation using diffusive gradient in thin-films (DGT) and phytoplankton in the Churchill River estuary", Manitoba. Chemosphere. 163: p. 90-8, 2016.

Martone et al., 2009. Discovery of lignin in seaweed reveals convergent evolution of cell-wall architecture. Current Biology. 19(2): p. 169-75.

McIntyre, AM et al., "Binding interactions of algal-derived dissolved organic matter with metal ions.", Chemosphere 90 (2013): 620-626.

Michaelson et al., 2010. Viral trans-dominant manipulation of algal sphingolipids. Trends Plant Science. 15(12): p. 651-655.

Mierle et al.; The Role of Flumic Substances in the mobilization of Mercury from watersheds. WaterAir Soil Pollut. 1991, 56 349-357.

Moreau et al.; The Effect of Natural Organic Matter on Mercury Methylation by Desulfobulbus propionicus I pr3. Front. Microbial. 2015, 6 (1389), 1-15.

Muresan B. et al., "Measurement and modeling of mercury complexation by dissolved organic matter isolates from freshwater and effluents of a major wastewater treatment plant", Appl. Geochem. 2011, 26, 2057-2063.

Müller et al., 2006. Brunsvicamides A-C: Sponge-Related Cyanobacterial Peptides with *Mycobacterium tuberculosis* Protein Tyrosine Phosphatase Inhibitory Activity. J. Med. Chem. 49, 4871-4878. doi:10.1021/jm060327w.

(56) References Cited

OTHER PUBLICATIONS

Ndu et al.; Effect of Inorganic and Organic Ligands on the Bioavailability of Methylmercury as Determined by Using a mer-lux Bioreporter. App. Environ. Microbial. 2012, 78 (20), 7276-7282.

Ngu-Schwemlein et al., Synthesis and ESI mass spectrometric analysis of the association of mercury(II) with multi-cysteinyl peptides. J Inorg Biochem, 2014, 133, 8-23.

Oestreich et al.; Colored Dissolved Organic Matter in Shallow Estuaries: Relationships between Carbon sources and light attenuation. Biogeosciences. 2016, 13, 583-595.

Ohno et al., Influence of heteroatom pre-selection on the molecular formula assignment of soil organic matter components determined by ultrahigh resolution mass spectrometry. Anal. Bioanal. Chem., 2013, 405 (10), 3299-3306.

Percopo et al., 2013. A new potentially toxic *Azadinium* species (Dinophyceae) from the Mediterranean Sea, *A. dexteroporum* sp. nov. J. Phycol. 49, n/a-n/a. doi: 10.1111/jpy.12104.

Peuravuori et al.; ESI-MS analyses of Lake Dissolved Organic Matter in Light of Supramolecular Assembly. Anal. Bioanal Chem. 2007, 389, 1559-1568.

Pirastru et al., 2012. Long-term stress induced by nitrate deficiency, sodium chloride, and high light on photosystem II activity and carotenogenesis of green alga *Scenedesmus* sp. Botany. 90(10): p. 1007-1014.

Prince et al., 1983. The glucose effect in Bacillus subtilis. European Journal of Biochemistry. 134: 105-7.

Qi et al.. Absorption-Mode: The Next Generation of Fourier Transform Mass Spectra. Anal. Chem. 2012, 84, 2923-2929.

Quoc et al., "Identification of Organic Ligands in Dissolved Organic Matter Produced by Scenedesmus obliquus Using Fourier Transform Ion Cyclotron Resonance Mass Spectomerty", [powerpoint presented on May 29, 2017].

Rasala et al., 2015. Photosynthetic biomanufacturing in green algae; production of recombinant proteins for industrial, nutritional, and medical uses. Photosynthesis Research. 123(3): p. 227-239.

Ravichandran M., "Interactions between Mercury and Dissolved Organic Matter—A Review",. Chemosphere. 2004, 55:319-331.

Rehman, A., "Heavy Metals Uptake by Euglena proxima Isolated from Tannery Effluents and Its Potential Use in Wastewater Treatment", Department of Microbiology and Molecular Genetics, ISSN 1067-4136, Russian Journal of Ecology, 2011, vol. 42, No. 1, pp. 44-49.

Remucal et al., 2012. Low molecular weight components in an aquatic humic substance as characterized by membrane dialysis and orbitrap mass spectrometry. Environmental Science & Technology. 46(17): p. 9350-9359.

Riedel, T., "Molecular fractionation of dissolved organic matter with metal salts", Environ Sci Technol, 2012, 46, 4419-4426.

Rodriguez, MS et al. , "Metal biosorption onto dry biomass of Arthrospira (Spirulina) platensis and Chlorella vulgaris: multi-metal systems.", Journal of Hazardous Materials 217 (2012): 246-255.

Rossolini et al., 2006. New beta-lactamases a paradigm for the rapid response of bacterial evolution in the clinical setting. Future Microbiology. 1(2): p. 295-308.

Roth et al., Latitude and pH driven trends in the molecular composition of DOM across a north south transect along the Yenisei River. Geochim Cosmochim Acta, 2013, 123, 93-105.

Roth et al., The molecular composition of dissolved organic matter in forest soils as a function of pH and temperature. PLoS One, 2013, 10 (3), 1-23.

Schaefer et al.; Effect of Divalent Metals on Hg (II) Uptake and Methylation by Bacteria. Environ. Sci. Technol. 2014, 48, 3007-3013.

Schartup A.T. et al., "Contrasting Effects of Marine and Terrestrially Derived Dissolved Organic Matter on mercury Speciation and Bioavailability in Seawater", Environ. Sci. Technol. 2015, 49, 5965-5972.

Schnitzer et al.; The alkaline hydrolysis of humic substances. Geoderma. 1975, 13, 171-188.

Schulze et al.; 2016. A one-stage cultivation process for lipid- and carbohydrate-rich biomass of Scenedesmus obtusiusculus based on artificial and natural water sources. Bioresource Technology. 218: p. 498-504.

Seitzinger S.P. et al., "Molecular-level chemical characterization and bioavailability of dissolved organic matter using electrospray ionization mass spectrometry", Limnol. Oceanogr. 2005, 50 (1), 1-12.

Selifonova et al.; Bioluminescent Sensors for Detection of Bioavailable Hg (II) in the Environment. Appl. Environ. Micro. 1993, 59 (9), 3083-3090.

Singh P. K., 1975. Sensitization of algal virus to UV by the incorporation of 5-bromouracil and mutations of host alga Plectonema boryanum. Journal of Basic Microbiology. 75(7):547-52.

Sipler et al., 2017. Microbial Community Response to Terrestrially Derived Dissolved Organic Matter in the Coastal Arctic. Frontiers in Microbiology. 8(1018): p. 1018.

Smith et al.; 2005. Metlin—A metabolite mass spectral database. Therapeutic Drug Monitoring. 27(6): p. 747-751.

Smith, S.; Metal Speciation in Natural Waters with Emphasis on Reduced Sulfur Groups as Strong Metal Bindings Sites. Comp Biochem Phys C. 2002, 133, 65-74.

Solliec et al., Quantitative performance of liquid chromatography coupled to Q-Exactive high resolution mass spectrometry (HRMS) for the analysis of tetracyclines in a complex matrix. Anal Chim Acta, 2015, 853, 415-424.

Sun L., Perdue E.M. et al., "Use of Elemental Composition to Predict Bioavailability of Dissolved Organic Matter in Georgia River", Limnol. Oceanogr. 1997, 42 (4), 714-721.

Superville et al.; Identification and on-line monitoring of reduced sulfur species (RSS) by voltammetry in oxic waters. Talanta. 2013, 112, 55-62.

Thornton, D.C.O. "Dissolved organic matter (DOM) release by phytoplankton in the contemporary and future ocean", European Journal of Phycology. 49(1): p. 20-46, 2014.

Vestola et al., 2014. Hassallidins antifunfal glycolipopeptides are widespread among cyanobacteria and are the end product of a nonribosomal pathway. Proceedings of the National Academy of Sciences. 111 (18): E1909-17.

Ward et al., 2016. Complete and Partial Photo-oxidation of Dissolved Organic Matter Draining Permafrost Soils. Environmental Science & Technology. 50(7): p. 3545-53.

Xia et al.; A. X-Ray Absorption Spectroscopic Evidence for the Complexation of Hg (II) by Reduced Sulfur in Soil Humic Substances. Environ. Sci. Technol. 1999, 33, 257-261.

Yamada, E. et al. "Biodegradation of Dissolved Organic Matter released from Phytoplankton in Lake Biwa", Analytical Sciences. 28: p. 675-681, 2012.

Yamamoto et al., 2014. Determination of volatile compounds in four commercial samples of Japanese green algae using SPE GO-MS. The Scientific World Journal. 2014:1-8.

Yang et al.; Silver Nanoparticle Behavior, Uptake and Toxicity in Caenorhabditis elegans: Effect of Natural Organic Matter. Environ. Sci. Technol. 2014, 48, 3486-3495.

European Examination Report for European Patent Application No. 17840680.7 dated Oct. 7, 2020.

European Extended Search Report for European Patent Application No. 18780942.1 dated Jan. 11, 2021.

Guo et. al: "Study of metal bioaccumulation by nuclear microprobe analysis of algae fossils and living algae cells", Nuclear Instruments & Methods in Physics Research Section B: Beam Interactions With Materials and Atoms, Elsevier BV, NL, vol. 161-163, Mar. 1, 2000 (Mar. 1, 2000), pp. 801-807.

Winters et al.: "Equilibrium and kinetic studies of Cu(II) and Ni(II) sorption on livingEuglena gracilis", Journal of Applied Phycology, Kluwer, Dordrecht, NL, vol. 29, No. 3, Dec. 24, 2016 (Dec. 24, 2016), pp. 1391-1398.

Kumar et al.: "Microalgae—A promising tool for heavy metal remediation", Ecotoxicology and Environmental Safety, vol. 113, Mar. 1, 2015 (Mar. 1, 2015), pp. 329-352.

Morene-Garrido et al.: "Microalgae immobilization: Current techniques and uses" Bioresource Technology, Elsevier, Amsterdam, NL, vol. 99, No. 10, Mar. 13, 2008 (Mar. 13, 2008), pp. 3949-3964.

(56) References Cited

OTHER PUBLICATIONS

Naomi P. Barkley: "Extraction of Mercury from Groundwater Using Immobilized Algae", Journal of the Air and Waste Management Association, vol. 41, No. 10, Oct. 1, 1991 (OCT. 1, 1991), pp. 1387-1393.

Vilchez et al.: "Microalgae-mediated chemicals production and wastes removal", Enzyme and Microbial Technology, vol. 20, No. 8, Jun. 1, 1997 (Jun. 1, 1997), pp. 562-572.

\* cited by examiner

Fig. 4
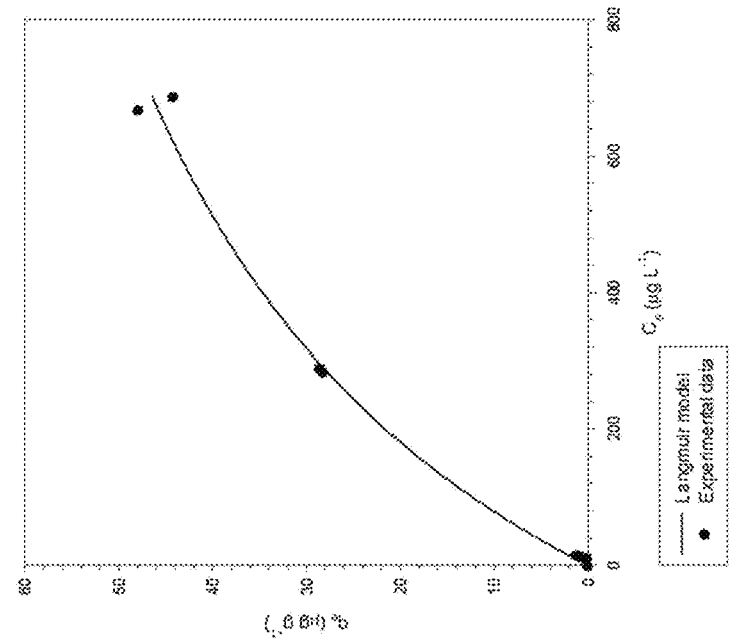
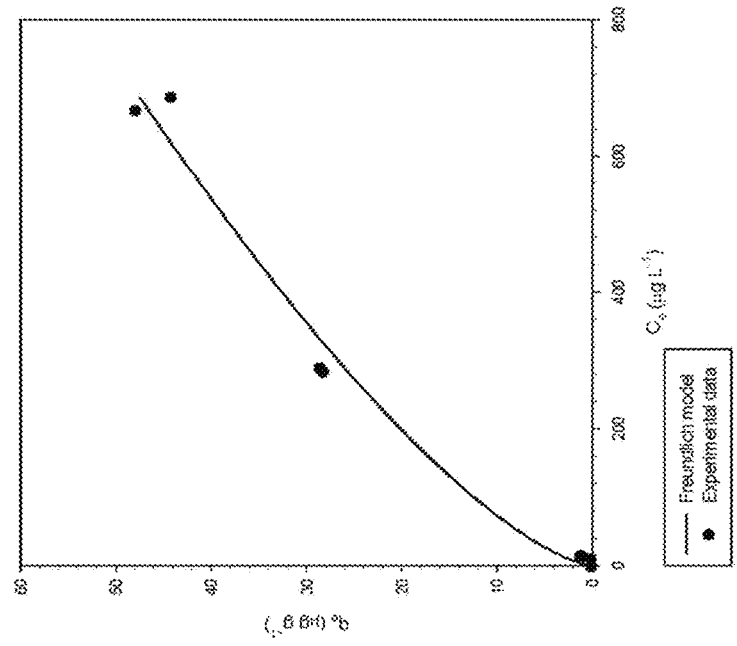

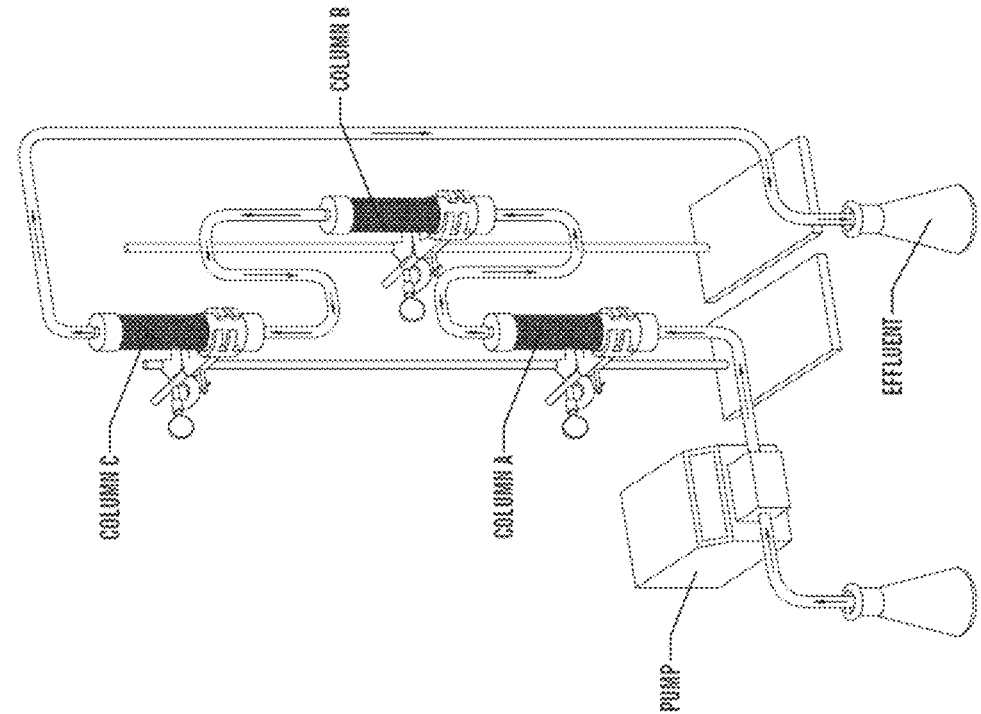
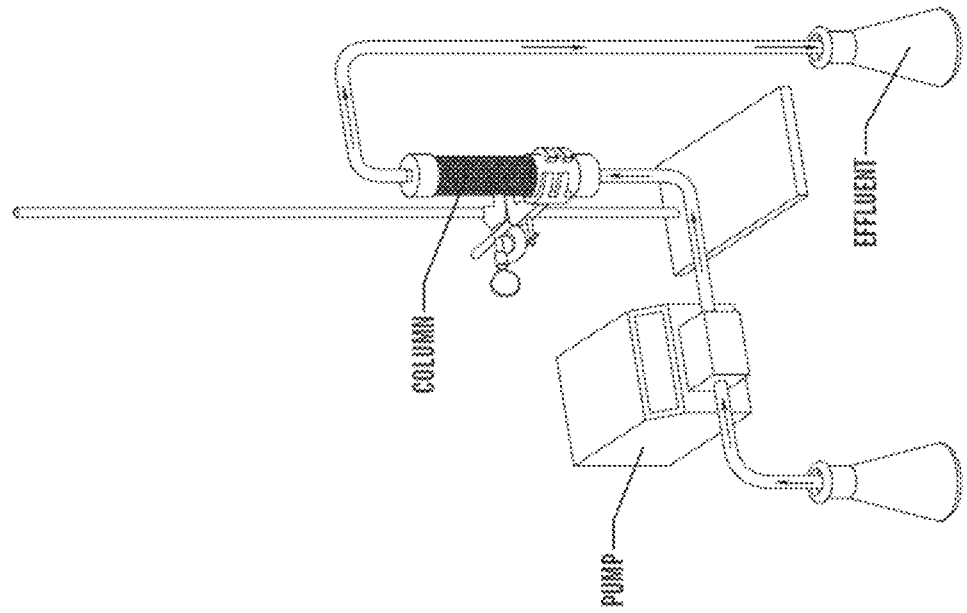
Fig. 8

Fig. 9
(A)
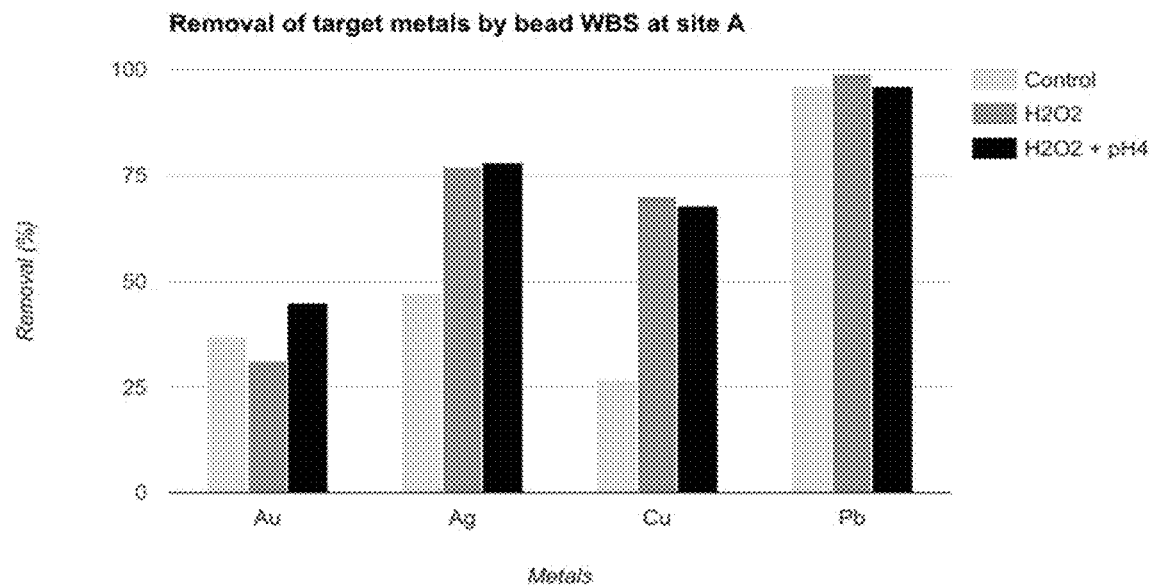
(B)
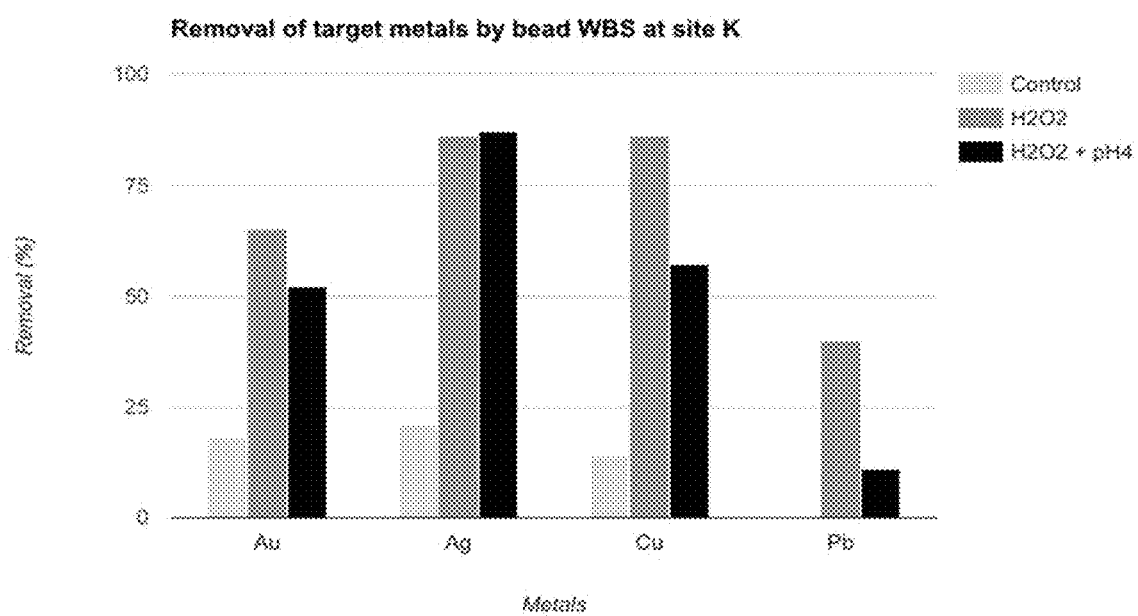

Fig. 11
(A)
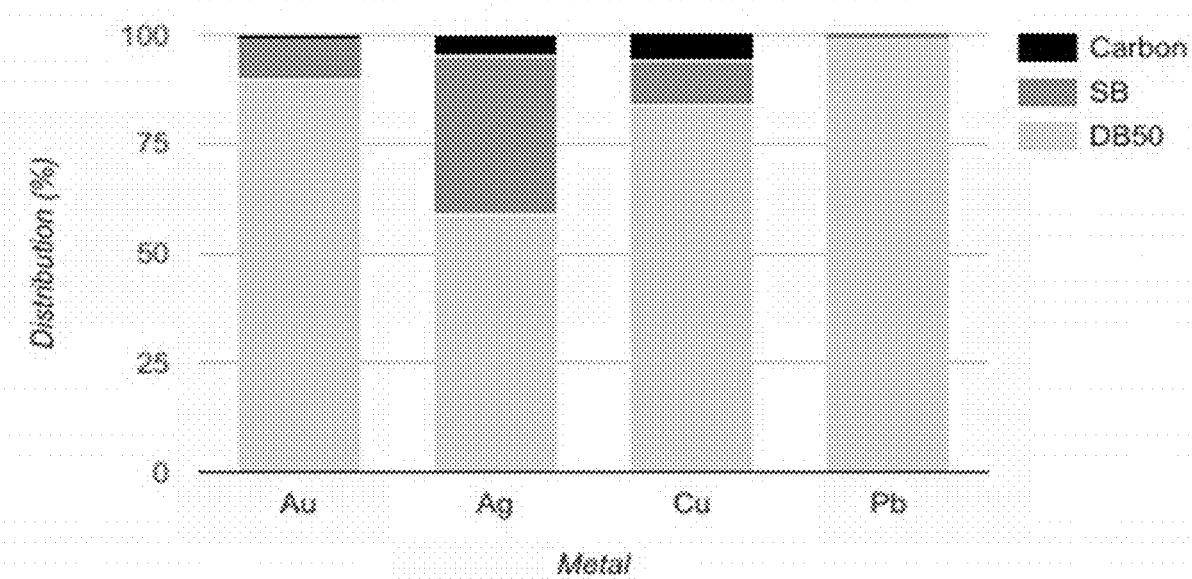
(B)
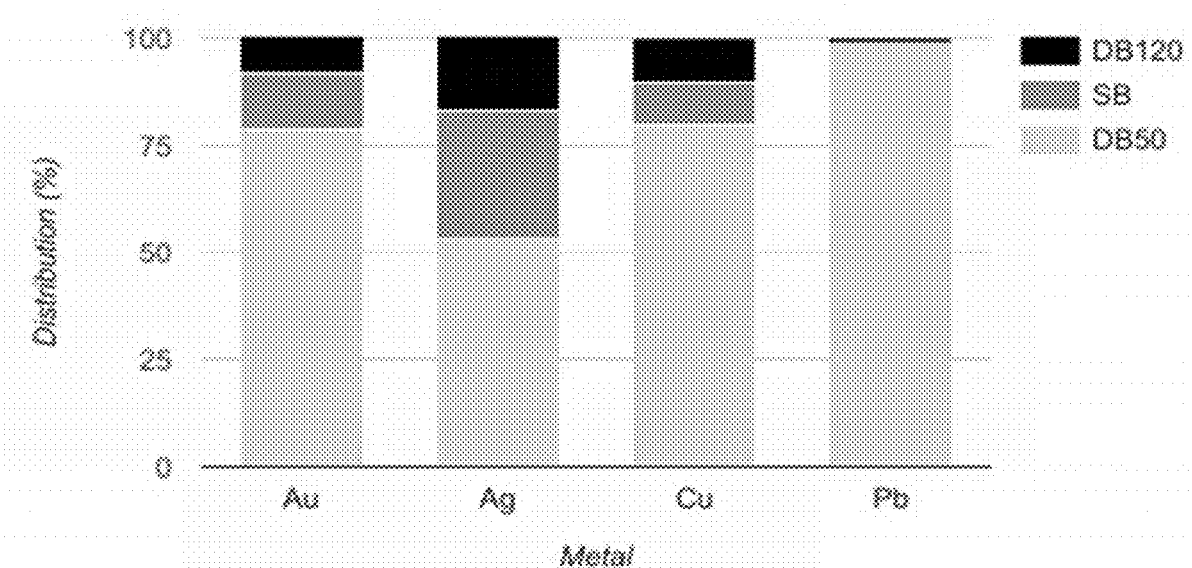

Fig. 12
(A)
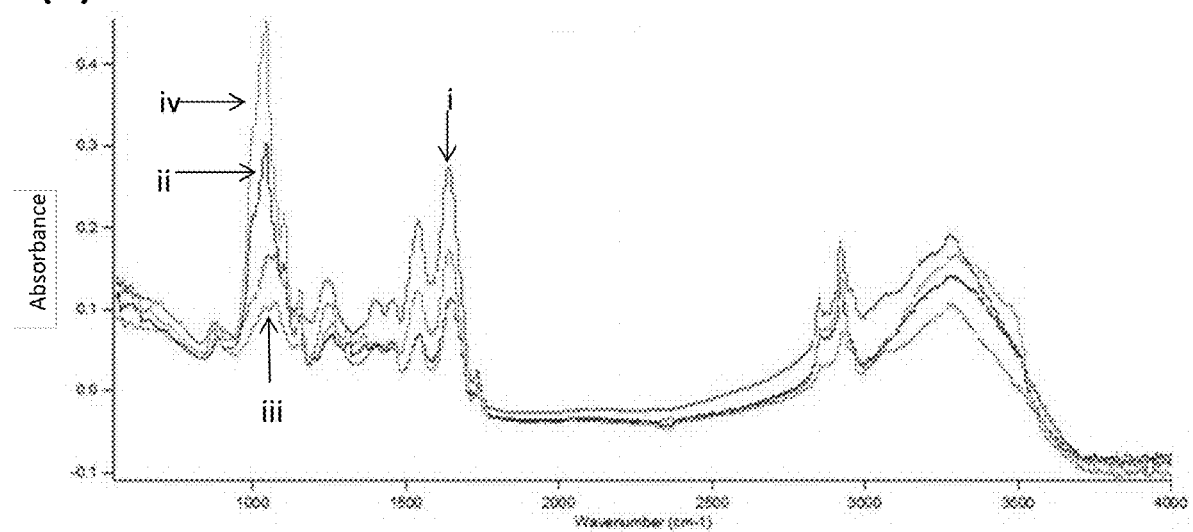
(B)
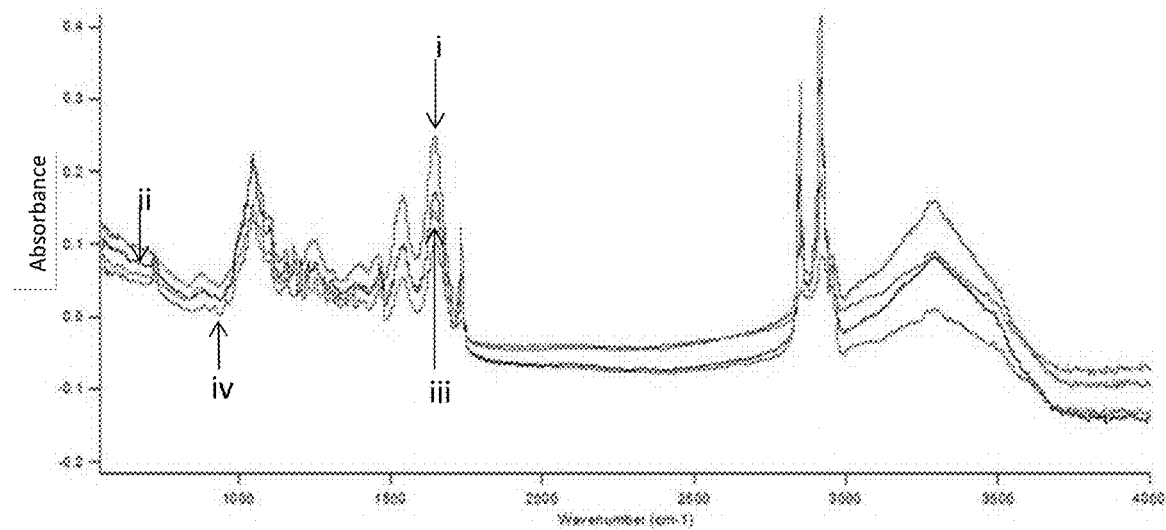

Fig. 13
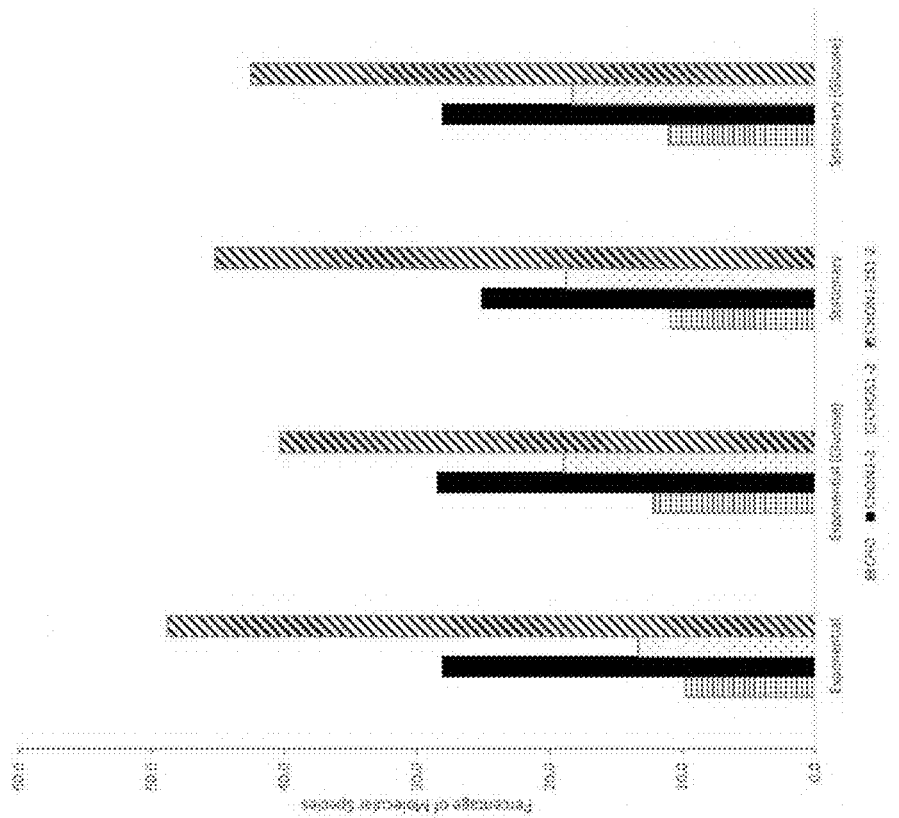
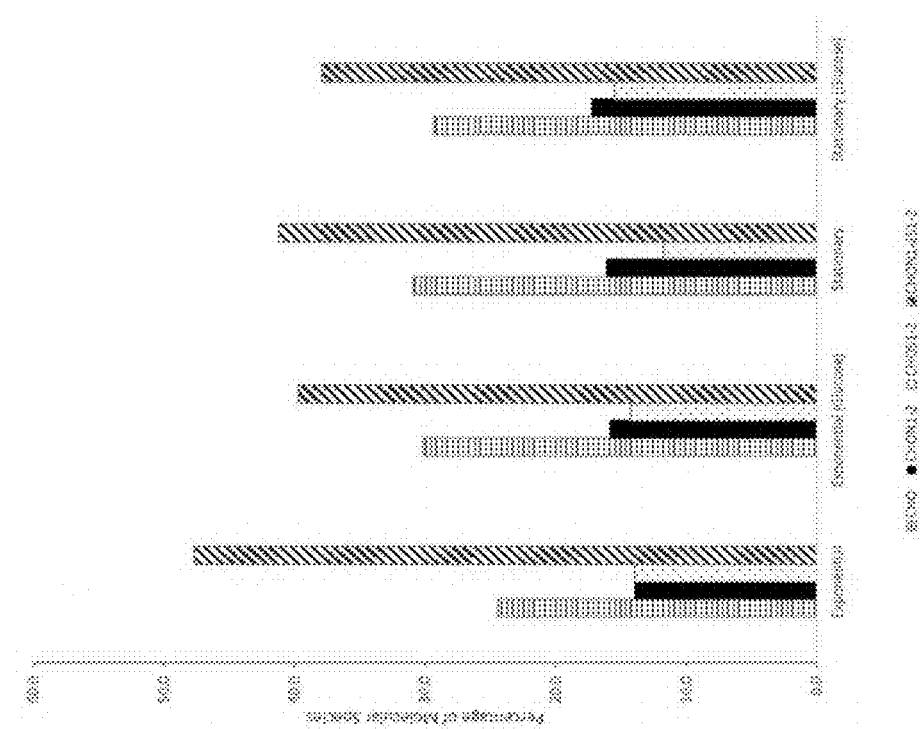

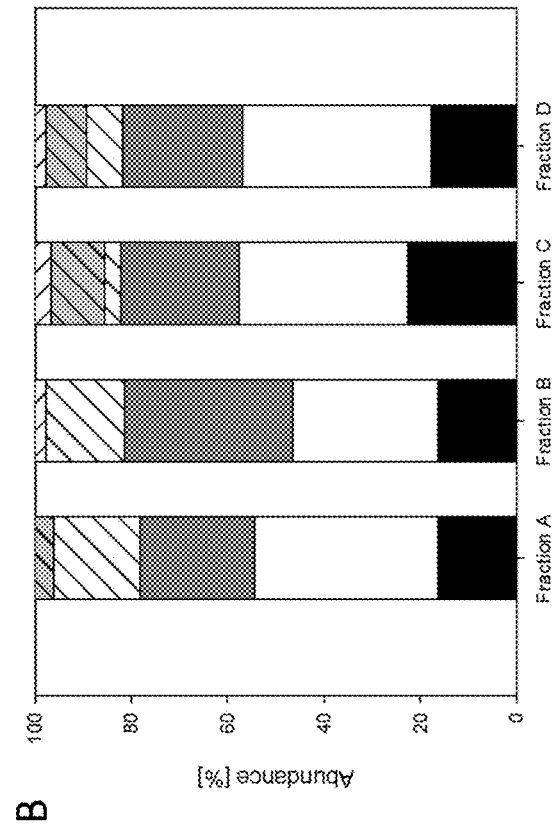
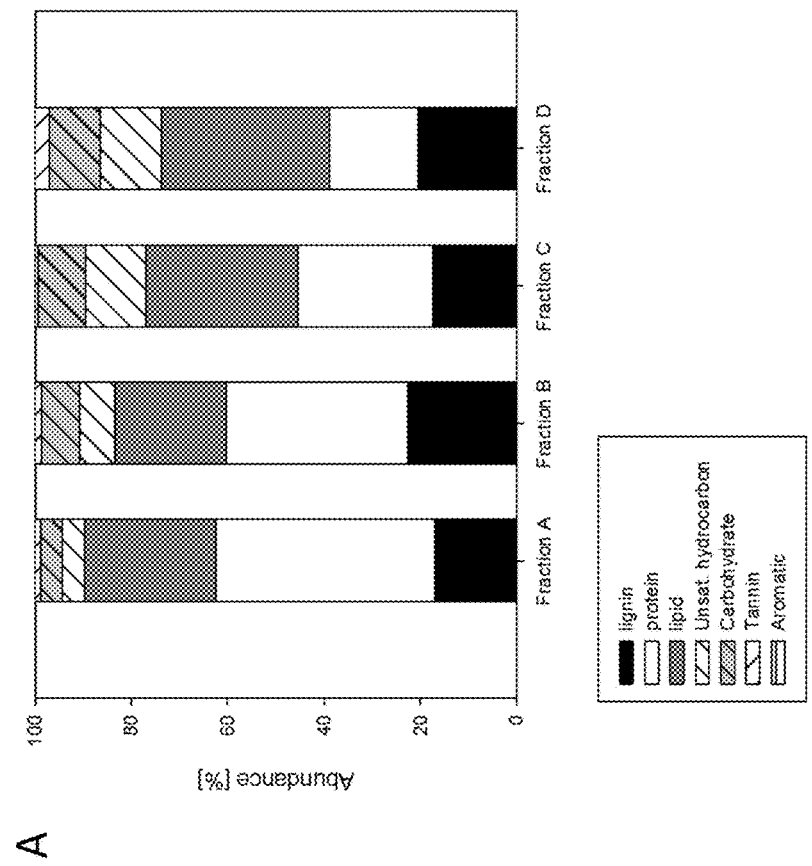
Fig. 22

Fig. 25
(A)
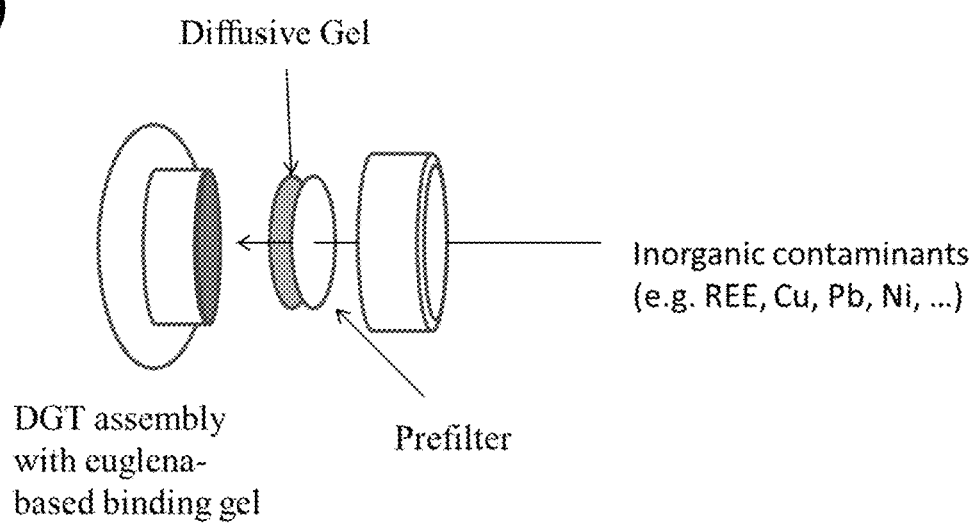
(B)
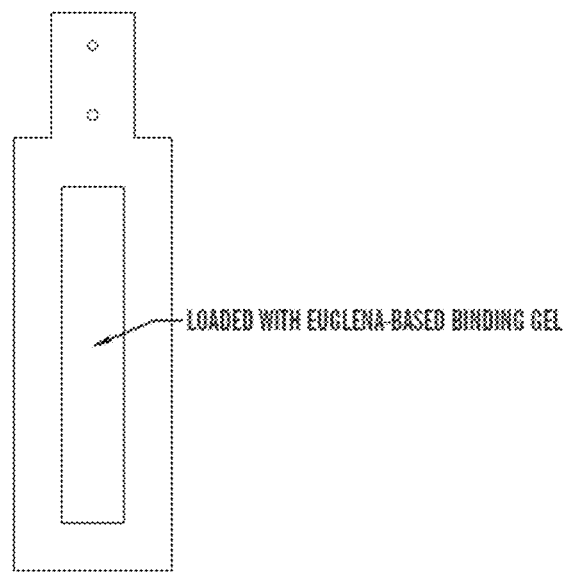

Fig. 27
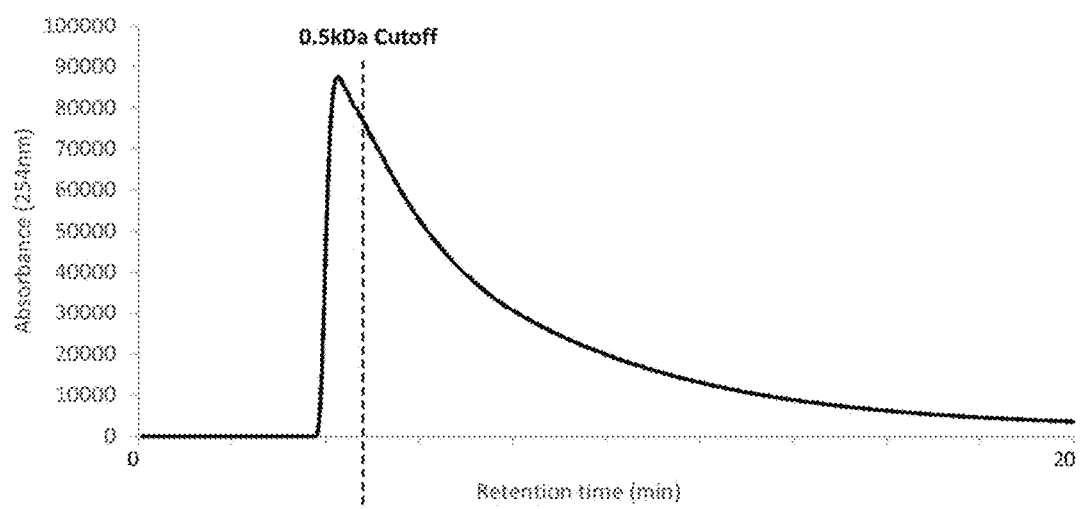
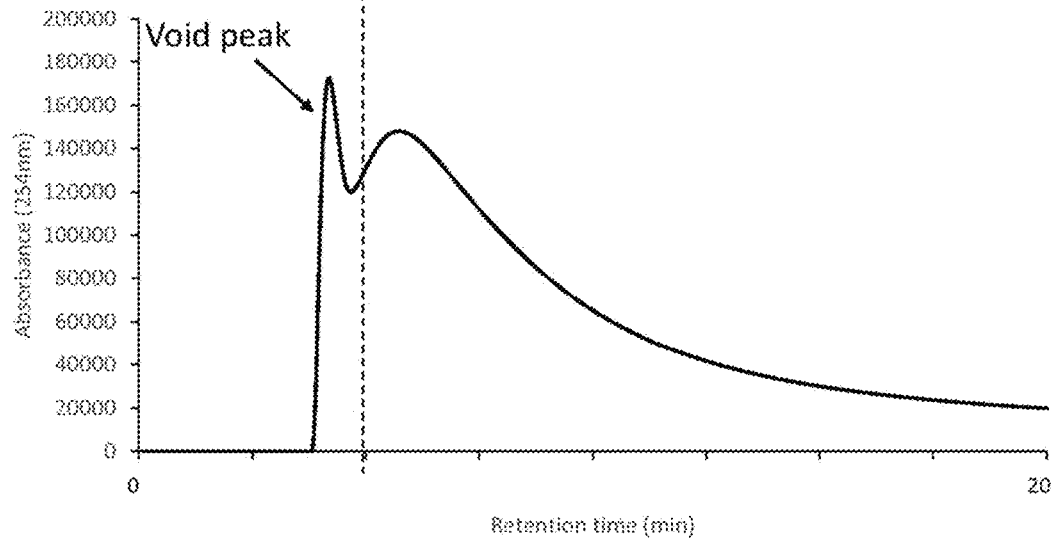

METHODS AND USES OF ENCAPSULATED EXUDATES AND DRIED *EUGLENA* BIOMASS FOR BINDING METAL

CROSS REFERENCE TO RELATED APPLICATION

This application is a national phase entry of PCT/CA2018/050431 filed Apr. 6, 2018 which claims the benefit of U.S. Provisional Application No. 62/482,952, filed Apr. 7, 2017, which is incorporated herein by reference in its entirety.

FIELD

The present disclosure relates to methods of binding metals, a biosorbent element, as well as methods of using the biosorbent element in binding metals and water remediation. For example, the present disclosure relates to methods and uses of an encapsulated exudate of a culture of algal flagellate, or a fraction thereof, or an encapsulated dried *Euglena* biomass, or a fraction thereof, for binding metals in water such as wastewater or mining process water.

BACKGROUND

Industrial wastewaters, generated from metal plating, mining, fertilizer production, tannery operations, battery production, pulp and paper, and pesticide production and application, are sources of heavy metal release into the environment which not only pose an ecological threat, but also may present serious consequences for human health (Fu and Wang, 2011). Consequently, there exists a necessity for the efficient removal of toxic metals from industrial effluent before any potential exposure to surface and ground waters.

Mining operations have historically contributed to elevated levels of metals in the surrounding environment (Keller et al., 2007). Conventional methods of metal removal can include chemical precipitation, resin-based ion exchange, and activated carbons as well as physical methods which utilize filtration, floatation, and coagulation (Fu and Wang, 2011). These methods, however, can tend to generate large capital and operational costs, substantial energy requirements, and large volumes of toxic waste materials (Wang and Chen, 2009). In addition, these procedures also tend to lack effectiveness at lower (<100 mg/L) concentrations and can become prohibitively expensive in terms of the volume of wastewater to be treated (Volesky, 2001).

As an alternative, the use of biological material for remediation of industrial wastewater, commonly referred to as biosorption and/or bioaccumulation, offers several advantages over conventional methods which include: ubiquity, the minimization of chemical and or biological sludge, operation over a broad range of physio-chemical conditions, relatively low capital investment and operational costs, and an increased efficiency in the removal of contaminants from dilute effluent (Abbas et al., 2014; Malik, 2004).

Both living and non-living biomass have been successfully utilized for metal removal and have been studied extensively although the use of non-living biomass is becoming the preferred option in the majority of recent metal removal studies (Fomina and Gadd, 2014; Doshi et al., 2007; Kizilkaya et al., 2012; Kumar et al., 2015; Michalak et al., 2013). The use of non-living biotic material confers several benefits compared to utilizing metabolically active organisms such as eliminating nutritional requirements, toxicity thresholds, allowing for desorption and metal recovery processes, and potentially improving sorption capacity through an increase in the cell surface to area ratio (Donmez et al., 1999; Kadukova and Vircikova, 2005). Live algal cells are also limited in terms of metal recovery as ions are bound intracellularly and/or metabolic exudates may form complexes with metal ions outside the cell which serve to retain metals in the aqueous phase.

Non-living biological material has the potential to effectively remove as much as or greater amounts of metal ions from solution when compared to living algal cells (Burdin and Bird, 1994; Tien et al., 2005). The characteristics of non-living algae mentioned above contribute in large part to the commercial viability of using such materials in remediation applications in potentially remote settings where infrastructure development is constrained by physical and economic limitations. Additionally, using inert algal material as opposed to living stock for metal removal can result in altered surface chemistry that influences cation sorption (Tien et al., 2005). Cell surfaces of algal organisms consist of an assortment of polysaccharides, proteins, and lipids all of which include functional groups (e.g. carboxyl, amino, thiol, sulphate and hydroxyl groups) that are capable of binding metal ions (Crist et al., 1981). Modifications of the cell surface/structure can occur when utilizing inactivation methods such as heat-drying, chemical treatments, and vacuum-drying which may result in increased or decreased sorption capacity and in this sense are dependent on the origin and pre-treatment of the biological material (Gardea-Torresdey et al., 1990; Winter et al., 1994).

*Euglena gracilis* is a free-floating, flagellated unicellular species of protist which has been found to tolerate and accumulate heavy metals (Rodriguez-Zavala et al., 2007). It is a candidate for use in bioremediation of wastewaters (Mendoza-Cozatl et al., 2006; Olaveson and Nalewajko, 2000).

SUMMARY

Accordingly, the present disclosure includes a method, comprising:
A method of binding a target metal, comprising:
contacting a solution containing
i) a target metal with
ii) an encapsulated exudate of a culture of algal flagellate, or a fraction thereof; or
an encapsulated dried *Euglena* biomass or a fraction thereof,
to form a complex between the target metal, and the encapsulated exudate or fraction thereof, or the encapsulated dried *Euglena* biomass or the fraction thereof; and
optionally separating the complex from the solution.

The present disclosure also includes a biosorbent element comprising a substrate carrying dried *Euglena* biomass, or a fraction thereof, or wet *Euglena* biomass, or a fraction thereof, or exudates of a culture of *Euglena*, or a fraction thereof, in sufficient quantity to adsorb metals from water passing therethrough, and methods of uses of the biosorbent element in binding metals in water.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments, but should be given the broadest interpretation consistent with the description as a whole.

BRIEF DESCRIPTION OF THE DRAWINGS

The present disclosure will now be described in greater detail with reference to the drawings, in which:

FIG. 4 shows $Cu^{2+}$ sorption equilibrium on non-living *E. gracilis*. (A) shows Freundlich model and (B) shows Langmuir model.

FIG. 8 shows (A) a single packed column, and (B) packed columns in series, with alginate beads inside.

FIG. 9 shows removal of target metals by bead WBS at (A) site A, and (B) site K.

FIG. 11 shows comparison of metal loading in (A) Series 1, and (B) Series 3, at site A.

FIG. 12 shows FTIR spectra for *E. gracilis* growing in (A) dark and (B) light conditions, with and without glucose supplementation in exponential and stationary phases. Trace (i): *Euglena gracilis* Medium (EGM) in exponential phase. Trace (ii): EGM+glucose in exponential phase. Trace (iii): EGM in stationary phase. Trace (iv) EGM+glucose at the stationary phase.

FIG. 13 shows molecular species seen at different stages of growth when *E. gracilis* grows in (A) light and (B) dark conditions.

FIG. 22 shows the abundances of compound classes found in AF4 fractions isolated from cells grown in (A) light and (B) dark conditions.

FIG. 25 shows the incorporation of non-living *Euglena* cells and/or exudates released by *Euglena* as binding sorbent for the passive concentration and removal of metals in a diffusive gradient in thin films (DGT) assembly.

FIG. 27 shows the *Euglena* exudates dialysate was slightly more enriched compared to SRFA.

DETAILED DESCRIPTION

I. Definitions

Figure 1:
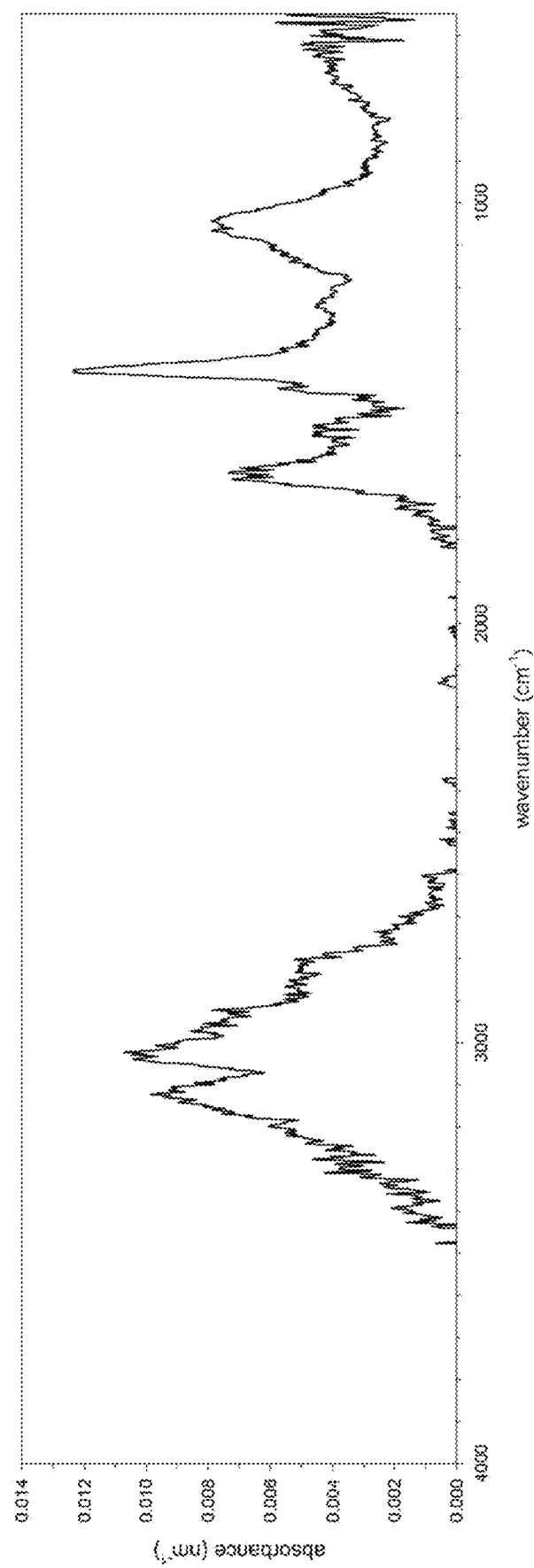
FIG. 1 shows Fourier Transform Infrared Spectroscopy (FTIR) spectra of dried *Euglena* biomass.

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

As used in this disclosure, the singular forms "a", "an" and "the" include plural references unless the content clearly dictates otherwise. In embodiments comprising an "additional" or "second" component, the second component as used herein is different from the other components or first component. A "third" component is different from the other, first, and second components, and further enumerated or "additional" components are similarly different.

As used in this disclosure, the term "algae" and its derivatives, as used herein, include photosynthetic microorganisms that are prokaryotes or eukaryotes. Photosynthetic microorganisms include photosynthetic microorganisms that are also capable of mixotrophic or heterotrophic growth.

As used in this disclosure, the term "algal flagellate" includes an algal microorganism with one or more flagella.

II. System, Methods and Uses

Dried algal flagellate biomass, or a fraction thereof, or an exudate of a culture of algal flagellate, or a fraction thereof, can bind to metals in water. Encapsulation of the dried algal flagellate biomass, or an exudate of a culture of algal flagellate provides a greater and more concentrated surface area for metal binding and also provides a method for the removal of dried algal flagellate biomass or an exudate of a culture of algal flagellate and the bound metals after the incubation period. The present examples demonstrated the usefulness of spherificated dried algal flagellate biomass, wet algal flagellate biomass, or a fraction thereof, or an exudate of a culture of algal flagellate, as well as a biosorbent element containing a substrate carrying a dried *Euglena* biomass, a wet *Euglena* biomass, or exudates of *Euglena*, or a fraction thereof, in binding to metals.

Accordingly, the present disclosure includes a method, comprising:

A method of binding a target metal, comprising:
contacting a solution containing
i) a target metal with
ii) an encapsulated exudate of a culture of algal flagellate, or a fraction thereof; or
an encapsulated dried *Euglena* biomass or a fraction thereof,
to form a complex between the target metal, and the encapsulated exudate or fraction thereof, or the encapsulated dried *Euglena* biomass or the fraction thereof; and
optionally separating the complex from the solution.

The term "solution" as used herein includes a homogeneous mixture composed of two or more substances.

The term "water" as used herein includes water in the form of a solution, suspension or slurry.

The term "non-living" as used herein refers to a microorganism being dead, lifeless, or metabolically inactive, a condition induced optionally by radiation, including electromagnetic radiation and particle radiation, biological treatment, chemical treatment, physical force, high hydrostatic pressure, or deprivation of necessities of life.

The term "exudate" as used herein refers to the secretion and/or excretion from a microorganism into a media or any surrounding liquid where it lives or once lived. An exudate may be obtained by subjecting a culture of microorganism to solid liquid separation using centrifugation, wherein the exudate is recovered from the liquid media phase.

The fraction of algal flagellate biomass or an exudate of a culture of algal flagellate comprises any suitable fraction of algal flagellate biomass or an exudate of a culture of algal flagellate for the binding of metals.

The term "metal" as used herein includes metal ions, anionic metals, cationic metals, metalloids, alloys, rare earth elements, light metals, heavy metals, transition metals, base metals, ferrous metals, noble metals and precious metals.

The metal can be any suitable metal which forms a complex with a dried algal flagellate biomass, or a fraction thereof, a wet algal flagellate biomass, or a fraction thereof, or an exudate of a culture of algal flagellate, or a fraction thereof. The expressions "form a complex" between the algal flagellate, an exudate of a culture of algal flagellate, or a fraction thereof and metal and "metal which forms a complex" with the algal flagellate, an exudate of a culture of algal flagellate, or a fraction thereof, as used herein refers to forming a complex between the metal and at least one compound that is a component of the fraction of the algal flagellate or an exudate of a culture of algal flagellate. The metal can be an anionic or cationic metal such as arsenic, rare earth elements, and radionuclides. It will be appreciated by a person skilled in the art that the non-living algal flagellate or an exudate of a culture of algal flagellate, or a fraction thereof, compounds with heteroatoms such as nitrogen (N), oxygen (O) and sulfur (S) that are capable of binding suitable metal ions. Non-living algal flagellate, an exudate of a culture of algal flagellate, or a fraction thereof is selected for binding a particular metal or class thereof. For example, Type-A metals typically form more stable complexes with O- and N-containing ligands whereas Type-B metals typically form more stable complexes with S-containing ligands and transition metals are known to exhibit behaviour intermediate between Type A and Type B metals. In some embodiments, the metal is a transition metal. For example, in some embodiments, the metal ion is a divalent transition metal (i.e. $M^{2+}$) and optionally is $He^{2+}$ or a divalent transition metal that shows similar binding to heteroatoms (e.g. N, O and S) such as $Zn^{2+}$, $Co^{2+}$, $Ni^{2+}$ or $Pb^{2+}$. In another embodiment, the metal ion is $Hg^{2+}$. In some embodiment, the metal is in a metal-cyano anionic complex.

The term "mining" as used herein includes an operation of extracting rare earth elements, aluminum, cobalt, copper, gold, molybdenum, nickel, palladium, platinum, rhodium, silver, uranium and/or zinc from the earth.

In one embodiment, the exudate may be obtained in a culture of any microorganism. In another embodiment, the exudate may be obtained in a culture of any algae.

In one embodiment, the metals are silver, gold, aluminum, arsenic, barium, beryllium, bismuth, calcium, cadmium, cobalt, chromium, copper, iron, potassium, lithium, magnesium, manganese, molybdenum, sodium, nickel, phosphorus, platinum, palladium, lead, antimony, selenium, tin, strontium, thallium, titanium, uranium, vanadium, tungsten, yttrium, zinc, scandium, lanthanum, rare earth element and divalent transition metals, optionally wherein the method binds a plurality of metals comprising at least two or more of the foregoing.

The methods of binding metal ions in solution are useful for any suitable use wherein it is desired to bind a metal ion in solution. The solution can be water, optionally wastewater, and the method is for remediation of water or wastewater having one or more metal to be removed. For example, the method may be used for the remediation of wastewater or mining process water as well as for other water treatment and water purification applications. In an embodiment, the method is for remediation of wastewater or mining process water having a metal ion to be removed and the water is wastewater or mining process water. The wastewater can be any suitable wastewater. For example, the wastewater can be domestic wastewater, urban wastewater, industrial wastewater or combinations thereof. The mining process water can be any suitable mining process water. For example, the mining process water can be from any mining operation involving the extraction of minerals or other geological materials.

The term "industrial wastewater" includes any suitable water that contains metal ions and is waste from industry. For example, the industrial wastewater can comprise metal processing effluent or wastewater from electroplating processes. For example, wastewater stemming from the grinding of mineral and sediment can include dissolved metals such as divalent metals, for example, mercury which can be bound in the methods of the present disclosure. Accordingly, in an embodiment, the industrial wastewater comprises effluent from a mining operation.

The term "mining process water" or "mining solution" includes any water used to leach metals of interest from rock or ore that contains those metals of interest in some concentration, or water at some point in a mining process that contains metals of interest in some concentration. Mining process water or mining solution includes water from carbon trains, resin columns, ponds such as excess, intermediate, pregnant and tailing ponds, leach pads, electrowinning cells, tanks such as flotation, Merrill Crowe, solid phase extraction and pregnant tanks. The skilled person readily recognizes sources of mining process water. In an embodiment, the methods described herein are for remediation or recovery of metals from mining process water selected from carbon trains, resin columns, ponds such as excess, intermediate, pregnant and tailing ponds, leach pads, electrowinning cells, tanks such as flotation, Merrill Crowe, solid phase extraction and pregnant tanks, using a biosorbent described herein. In another embodiment, the methods described herein are for remediation or recovery of metals from mining process water entering or leaving carbon trains, resin columns, ponds such as excess, intermediate, pregnant and tailing ponds, leach pads, electrowinning cells, tanks such as flotation, Merrill Crowe, solid phase extraction and pregnant tanks, using a biosorbent described herein. In a specific embodiment, the methods described herein are for recovery of precious metals, optionally gold, silver, platinum and palladium, from mining process water selected from carbon trains, resin columns, ponds such as excess, intermediate, pregnant and tailing ponds, leach pads, electrowinning cells, tanks such as flotation, Merrill Crowe, solid phase extraction and pregnant tanks, using a biosorbent described herein. In another specific embodiment, the methods described herein are for recovery of precious metals, optionally gold, silver, platinum and palladium, from mining process water entering or leaving carbon trains, resin columns, ponds such as excess, intermediate, pregnant and tailing ponds, leach pads, electrowinning cells, tanks such as flotation, Merrill Crowe, solid phase extraction and pregnant tanks, using a biosorbent described herein.

The methods of the present disclosure can also be used to capture a metal ion of interest from the water. For example, so that the metal ion can be converted into the metal.

In an embodiment, the mining process water comprises a metal of interest at concentration of 0.1-2000 ppm, 1-1000 ppm, 5-800 ppm, or 10-600 ppm. In another embodiment, the mining process water comprises a metal of interest at concentration equal to or less than 2000, 1500, 1250, 1200, 1000, 900, 800, 700, 600, 500, 400, 300, 200 and 100 ppm.

In an embodiment, the mining process water comprises a pH range of 2-13, or 8-11. In another embodiment, the mining process water comprises a pH of equal to or more than 2, 3, 4, 5, 6, 7, 8, 9 and 10. In another embodiment, the mining process water comprises a pH of equal to or less than 13, 12, 11, 10, 9, 8, 7 and 6.

In an embodiment, the mining process water was depleted of cyanide (CN). In another embodiment, the mining process water was treated with hydrogen peroxide. In another embodiment, the mining process water was treated with hydrogen peroxide to deplete CN.

In an embodiment, the complex is separated from the solution. The method of separation can involve any suitable means of separation and will depend, for example, on the method by which the solution is contacted with the encapsulated dried algal flagellate biomass, or a fraction thereof, or a dried algal flagellate biomass, or a fraction thereof, or an exudate of a culture of algal flagellate, or a fraction thereof. In an embodiment, the separation comprises contacting the complex with a microorganism or microorganism material to sequester the complex. The microorganism is any suitable microorganism that can uptake or sequester the complex. For example, gram-negative bacteria *E. coli* and any other suitable microorganism are useful in this regard. The microorganism material comprises any suitable microorganism material that can uptake or sequester the complex. For example, materials from gram-negative bacteria *E. coli* and any other suitable microorganism are useful in this regard.

In another embodiment, the algal flagellate is a Chlamydomonadaceae, a Cryptophyceae, a Dinoflagellate, an Euglenaceae, a Haptophyta, or mixtures thereof. In another embodiment, the algal flagellate is a *Chlamydomonas* sp., a *Cryptophyta* sp., a Dinophyta sp., an *Euglena* sp, or mixtures thereof. In another embodiment, the algal flagellate is *Chlamydomonas reinhardtii, Euglena gracilis, Euglena mutabilis*, or combinations thereof. In another embodiment, the algal flagellate is *Euglena gracilis*. In another embodiment, the algae flagellate is *Euglena gracilis, Euglena mutabilis* or combinations thereof. In a further embodiment, the algal flagellate comprises, consists essentially of or consists of *Euglena gracilis*.

In another embodiment, the algae is a *Chlorella* sp., a diatom, a cyanobacteria, a protist or mixtures thereof. In a further embodiment, the algae is *Chlorella vulgaris, Chlamydomonas reinhardtii, Euglena gracilis, Euglena mutabilis, Scenedesmus obliquus, Thalassiosira weissflogii* or combinations thereof.

In another embodiment, the exudate of a culture of algal flagellate comprises glutathione, metallothioneins, phytochelatins, polyphosphates, polysaccharides, or combinations thereof. It is an embodiment that the exudate of a culture of algal flagellate, or the encapsulated non-living *Euglena* biomass, is spherificated or gelificated. In another embodiment, the spherification or gelification process comprises using an encapsulating immobilizing matrix to encapsulate the exudates of a culture of algal flagellate, or dried *Euglena* biomass in an immobilizing matrix. In another embodiment, the immobilizing matrix comprises a resin or a polymer plastic. In another embodiment, the immobilizing matrix comprises agar, agarose, alginate, carrageenan, cellulose, chitosan, polystyrene, polyurethane, polyvinyl, or combinations thereof. In another embodiment, the immobilizing matrix comprises sodium alginate. In another embodiment, the exudate of a culture of algal flagellate is housed in a containment element. In another embodiment, the containment element comprises a semi-permeable membrane. In a further embodiment, the semi-permeable membrane comprises integral asymmetric membrane or thin film composite membrane.

The term "activated carbon" and its derivatives as used herein refers to a form of carbon processed to have small, low-volume pores, optionally 0.3-3 $cm^3/g$, that increase the surface area available for metal adsorption and/or chemical reactions. An activated carbon may be obtained from nutshells, coconut husk, peat, wood, coir, lignite, coal, and/or petroleum pitch.

In another embodiment, an exudate of a culture of algal flagellate is spherificated or gelificated and further mixed with activated carbon. In another embodiment, the activated carbon comprises nutshells, coconut husk, peat, wood, coir, lignite, coal, and/or petroleum pitch.

As used in this disclosure, the term "encapsulate" and its derivatives, as used herein, refers to a state where a matter is surrounded by a gelatinous substance(s), such as substantially surrounded or fully surrounded. The process of encapsulation comprises spherification or gelification.

As used in this disclosure, the term "unencapsulated" and its derivatives, as used herein, refers to a state where a matter is not encapsulated.

In an embodiment, an unencapsulated exudate of a culture of algal flagellate, or a fraction thereof, or an unencapsulated dried *Euglena* biomass, or a fraction thereof, or an unencapsulated wet *Euglena* biomass, or a fraction thereof, binds metals described herein in water such as wastewater or mining process water. In another embodiment, an unencapsulated exudate of a culture of algal flagellate, or a fraction thereof, or an unencapsulated dried *Euglena* biomass, or a fraction thereof, or an unencapsulated wet *Euglena* biomass, or a fraction thereof, is for use in remediation of wastewater having the metals described herein to be removed and the water is wastewater or mining process water, optionally before the wastewater or mining process water contacts activated carbon.

As used in this disclosure, the terms "biosorbent" and "biosorbent element" are used interchangeably.

In an embodiment, a biosorbent described herein comprises an encapsulated or unencapsulated microorganism, or an exudate of a culture of microorganism described herein. In another embodiment, a biosorbent described herein comprises an encapsulated or unencapsulated microorganism, aquatic microorganism, algae, algal flagellate, *Chlamydomonas* sp., *Cryptophyta* sp., *Dinophyta* sp., *Euglena* sp, *Chlamydomonas reinhardtii, Euglena mutabilis, Euglena gracilis*, combinations thereof, a fraction thereof, or combinations of fractions thereof, or an exudate of a culture of said microorganism, aquatic microorganism, algae, algal flagellate, *Chlamydomonas* sp., *Cryptophyta* sp., *Dinophyta* sp., *Euglena* sp, *Chlamydomonas reinhardtii, Euglena mutabilis, Euglena gracilis*, combinations thereof, a fraction thereof, or combinations of fractions thereof.

In an embodiment, methods described herein comprise uses of an encapsulated or unencapsulated microorganism, or an exudate of a culture of microorganism described herein. In another embodiment, methods described herein comprise an encapsulated or unencapsulated microorganism, aquatic microorganism, algae, algal flagellate, *Chlamydomonas* sp., *Cryptophyta* sp., *Dinophyta* sp., *Euglena* sp, *Chlamydomonas reinhardtii, Euglena mutabilis, Euglena gracilis*, combinations thereof, a fraction thereof, or combinations of fractions thereof, or an exudate of a culture of said microorganism, aquatic microorganism, algae, algal flagellate, *Chlamydomonas* sp., *Cryptophyta* sp., *Dinophyta* sp., *Euglena* sp, or *Chlamydomonas reinhardtii, Euglena mutabilis, Euglena gracilis*, combinations thereof, a fraction thereof, or combinations of fractions thereof.

As used in this disclosure, the term "gelificate" and its derivatives, as used herein, is defined as the process of turning a substance into a gelatinous form. This process comprises converting liquid substances into solids with the help of a gelling agent. Common gelling agents come from natural sources and include agar-agar, gelatin, carrageenan, gellan gum, pectin and methylcellulose.

As used in this disclosure, the term "bead" and its derivatives, as used herein, refers to encapsulated algal flagellate or exudates of a culture of algal flagellate, or a fraction thereof.

In another embodiment, the pH of the beads is at least 2, 3, 4, 5, 6, or 7. In another embodiment, the pH of the beads is at most 6, 7, 8, 9, 10, 11, 12 or 13. In another embodiment, the pH of the beads is between 2 and 13, optionally between 3 and 10, optionally between 4 and 7.

In another embodiment, the bead size is at least 0.1, 0.2, 0.3, 0.4, 0.5, 1, 1.5, 2, 2.5, 3, 3.5, 4, 4.5 or 5 mm. In another embodiment, the bead size is at most 4, 5, 6, 7, 8, 9, or 10 mm. In another embodiment, the bead size is between 0.1 and 10, optionally between 2 and 6, optionally between 3 and 5.

As used in this disclosure, the term "dried biomass" and its derivatives, as used herein, is defined as a biomass consists of moisture content of at most 25%.

In another embodiment, the moisture content of dried biomass is equal to or less than 25, 24, 23, 22, 21, 20, 19, 18, 17, 16, 15, 14, 13, 12, 11 and 10 and 5%. In another embodiment, the moisture content of dried biomass is between 5 and 25%, or between 10 and 20%. In another embodiment, the moisture content of dried biomass is below 10%, or below 5%.

As used in this disclosure, the term "wet biomass" and its derivatives, as used herein, is defined as a biomass consists of moisture content of more than 25%.

In another embodiment, the moisture content of wet biomass is more than 25, 30, 35, 40, 45, 50, 55, 60, 65, 70, 75, 80, 85 and 90%. In another embodiment, the moisture content of wet biomass is at least 26, 27, 28, 29, 30, 35, 40, 45, 50, 55, 60, 65, 70, 75, 80, 85 and 90%. In another embodiment, the moisture content of wet biomass is between 30 and 90%, between 50 and 85%, or between 70 and 80%.

In another embodiment, the amount or type of metal sequestered per weight of active material of the algal flagellate biomass is modified by post-harvest treatment prior to spherification. In another embodiment, the post-harvest treatment comprises drying the biomass or fraction thereof. In another embodiment, the drying treatment comprises treating the biomass at a temperature of at least 45, 50, or 55° C. In another embodiment, the drying treatment comprises drying the biomass for at least 24, 36, 48, 60, 72, 84 or 96 hours. In another embodiment, the drying treatment comprises drying the biomass for about 72 hours at 50° C.

In another embodiment, the post-harvest treatment comprises heating the biomass or fraction thereof. In another embodiment, the heat treatment comprises treating the biomass at a temperature of at least 56, 57, 58, 59, 60, 65, 70, 75, 80, 85, 90, 95, 100, 105, 110, 120, 125, 130, 140, 145, 150, 155 or 160° C. In another embodiment, the heat treatment comprises heating the biomass for at least 24, 36, 48, 60, 72, 84 or 96 hours. In another embodiment, the heat treatment comprises heating the biomass for about 72 hours at 80 or 120° C. In another embodiment, the heat treatment comprises heating the biomass for about 72 hours at 80 or 120° C.

In another embodiment, the exudates of a culture of algal flagellate, the encapsulated dried *Euglena* biomass, the post-harvest treated encapsulated dried *Euglena* biomass and/or the wet *Euglena* biomass, comprising different metal binding selectivities are housed in a plurality of columns, the columns arranged to produce a column effluent. In another embodiment, the plurality of columns is arranged in a series comprising a first column, a second column and a third column, and the solution flows through the columns sequentially to produce the column effluent. In another embodiment, the first column selectively binds to copper, the second column selectively binds to silver, and the third column selectively binds to gold. In another embodiment, the algal flagellate biomass or exudates of a culture of algal flagellate comprises selectivity for lead, copper, silver and/or gold. In another embodiment, the algal flagellate biomass or exudates of a culture of algal flagellate comprises selectivity for a metal described herein.

In another embodiment, a pre-treatment of the solution is performed by mixing the solution with an appropriate amount of either the spherificated algal flagellate biomass or free algal flagellate, followed by the removal of the spherificated algal flagellate biomass or free algal flagellate. In another embodiment, the pre-treated solution is passed through a column or a series of columns containing spherificated algal flagellate biomass or an exudate of a culture of algal flagellate.

In an embodiment, the biosorbent described herein has the loading capacity of at least 0.01, 0.1, 1, 10, 100, 1000, $1 \times 10^4$, $1 \times 10^5$, $1 \times 10^6$, $2 \times 10^6$, $3 \times 10^6$, $4 \times 10^6$, or $5 \times 10^6$ gram metal described herein per tonne biosorbent.

As used in this disclosure, a "desorbent" is a solution that is used to release a substance (for example, a target metal) from the structure that it is bound to (for example, an encapsulated biomass, exudates, or a fraction thereof).

Desorption is carried out to liberate/reactivate the binding sites of the structure, which allows for the collection of the target metal in solution and the ability for further binding (i.e. adsorption) by the encapsulated exudates/biomass to a target metal in a solution, preferably fresh solution. A successful desorption or desorbent can accomplish the foregoing advantages, while limiting the effect on the stability and/or integrity of the adsorptive structure. Desorbents can optionally include acids (e.g. nitric acid, hydrochloric acid, sulphuric acid, citric acid), bases (e.g. sodium hydroxide, sodium carbonate, sodium bicarbonate), chelating agents (e.g. EDTA), or other compounds (e.g. thiourea, potassium cyanide, sodium citrate, sodium nitrate). Biosorbent described herein can optionally undergo multiple rounds or cycles of desorption and adsorption while retaining stability and/or integrity of the adsorptive structure. The skilled person readily recognizes alternate desorbents suitable for desorption of a target metal from a biosorbent described herein.

In an embodiment, the methods described herein further comprise desorbing the target metal. In another embodiment, the desorbing of the target metal comprises contacting the complex with a desorbent. In another embodiment, the desorbent comprises an acidic or basic solution. In another embodiment, the desorbent comprises potassium cyanide or thiourea. In another embodiment, the acidic solution comprises one or more of hydrochloric acid, nitric acid, sulphuric acid, and citric acid. In another embodiment, the basic solution comprises one or more of sodium hydroxide, sodium carbonate, and sodium bicarbonate. In another embodiment, the target metal is a precious metal, optionally gold, silver, platinum or palladium. In an embodiment, a desorbent described herein desorbs at least 50%, 60%, 70%, 80%, 85%, 90%, 91%, 92%, 93%, 94%, 95%, 96%, 97%, 98%, 99%, or 100% of a target metal described herein from a biosorbent described herein. In another embodiment, biosorbents described herein retain at least 70%, 75%, 80%, 85%, 90%, 91%%, 92%, 93%, 94%, 95%, 96%, 97%, 98%, 99%, or 100% binding capacity to a target metal described herein, after at least 1, 2, 3, 4, 5, 6, 7, 8, 9, 10, 12, 14, 15, 16, 18, 20, 25, 30, 35, 40, 45, or 50 rounds or cycles of desorption and adsorption. In another embodiment, the desorption methods described herein retain at least 70%, 75%, 80%, 85%, 90%, 91%%, 92%, 93%, 94%, 95%, 96%, 97%, 98%, 99%, or 100% binding capacity to a target metal described herein, after at least 1, 2, 3, 4, 5, 6, 7, 8, 9, 10, 12, 14, 15, 16, 18, 20, 25, 30, 35, 40, 45, or 50 rounds or cycles of desorption and adsorption.

As used herein, the term "fresh" refers to a new or different batch of solution and does not necessarily mean that the solution is freshly made, acquired, obtained, or retrieved from a source. In another embodiment, after desorbing the target metal from the complex, the encapsulated exudate of a culture of algal flagellate or a fraction thereof, the encapsulated dried *Euglena* biomass or a fraction thereof, or the encapsulated wet *Euglena* biomass or a fraction thereof, contacts a fresh solution containing a target metal. In an embodiment, a fresh solution comprises mining process water or mining solution.

As used in this disclosure, the term "selective" and its derivatives, as used herein, refers to a preference towards one metal over others.

In an embodiment, the algae is grown in light in the absence or presence of glucose supplement. In an embodiment, the algae is grown in the dark in in absence or presence of glucose supplementation. In another embodiment, the algae is grown in the light for 24, 48 or 72 h until reaching exponential growth phase. In another embodiment, the algae is grown in the dark for 24, 48 or 72 h or until reaching exponential growth phase. In yet another embodiment, the glucose supplementation comprises a range of 0.1 to 20 $g \cdot L^{-1}$ glucose.

In an embodiment, a biosorbent element contains a substrate carrying a dried *Euglena* biomass, or an exudate of a culture of *Euglena*, or a fraction thereof, in sufficient quantity to adsorb metals from water passing therethrough. In another embodiment, the biosorbent element is a biosorbent diffusive gradient across a plurality of thin films. In a further embodiment, the biosorbent element binds metals comprise silver, gold, aluminum, arsenic, barium, beryllium, bismuth, calcium, cadmium, cobalt, chromium, copper, iron, potassium, lithium, magnesium, manganese, molybdenum, sodium, nickel, phosphorus, platinum, palladium, lead, antimony, selenium, tin, strontium, thallium, titanium, uranium, vanadium, tungsten, yttrium, zinc, scandium, lanthanum, rare earth elements and divalent transition metals.

In another embodiment, the biosorbent element is for method or use in remediation of wastewater having the metals to be removed and the water is wastewater. In another embodiment, the biosorbent element is for method or use in remediation of mining process water having the metals to be removed and the water is mining process water. In another embodiment, the wastewater is domestic wastewater, urban wastewater, industrial wastewater or combinations thereof. In a further embodiment, the industrial wastewater comprises effluent from a mining operation.

In another embodiment, the biosorbent element is for method or use in remediation of wastewater having the metals to be removed and the water is wastewater, optionally before the wastewater contacts activated carbon.

In another embodiment, the biosorbent element is for method or use in remediation of mining process water having the metals to be removed and the water is mining process water. In another embodiment, the wastewater is domestic wastewater, urban wastewater, industrial wastewater or combinations thereof. In a further embodiment, the industrial wastewater comprises effluent from a mining operation.

In an embodiment, the biosorbent element contains a dried *Euglena* biomass, or a fraction thereof, a wet *Euglena* biomass, or a fraction thereof, or an exudate of a culture of *Euglena*, or a fraction thereof, that includes glutathione, metallothioneins, phytochelatins, polyphosphates, polysaccharides, or combinations thereof. In another embodiment, the biosorbent element in contained in a dialysis container or dialysis bag. In another embodiment, the biosorbent element is embedded in diffusive gradient in a plurality of thin films, optionally a diffusion gradient technology (DGT). In another embodiment, the dried *Euglena* biomass, or a fraction thereof, a wet *Euglena* biomass, or a fraction thereof, or the exudates of a culture of *Euglena*, or a fraction thereof, is spherical and/or gelatinous. In another embodiment, the biosorbent element includes an immobilizing matrix to encapsulate the dried *Euglena* biomass, or a fraction thereof, a wet *Euglena* biomass, or a fraction thereof, or the exudates of a culture of *Euglena*, or a fraction thereof. In another embodiment, the immobilizing matrix includes a resin, a polymer plastic, or diffusive gradient in thin films. In another embodiment, the immobilizing matrix comprises agar, agarose, alginate, carrageenan, cellulose, chitosan, polystyrene, polyurethane, polyvinyl, or combinations thereof. In a further embodiment, the immobilizing matrix contains sodium alginate.

In another embodiment, the fraction is fraction A, B, C or D from AF4 fractionation, optionally fraction C. In another embodiment, fraction C comprises fraction eluant between 9 and 10 min retention time from AF4 fractionation. The skilled person readily recognizes alternates to AF4 fractionation to obtain a fraction with biochemical characteristics and metal binding properties similar to fraction C.

In another embodiment, the biosorbent element is for method or use in remediation of wastewater, optionally mining process water, to remove Au, Ag, Cu, and/or Pb, optionally the wastewater has been depleted of CN, optionally the biosorbent element comprises unencapsulated *Euglena* biomass, encapsulated *Euglena* biomass beads, or beads comprising exudates of a culture of *Euglena*, optionally the *Euglena* biomass was heat treated at a temperature of at least 40, 45, 50, 51, 52, 53, 54, 55, 56, 57, 58, 59, 60, 65, 70, 75, 80, 85, 90, 95, 100, 105, 110, 120, 125, 130, 140, 145, 150, 155 or 160° C., optionally the heat treatment comprises heating the biomass for at least 12, 24, 36, 48, 60, 72, 84 or 96 hours, optionally the bead comprises bead size of at least 0.1, 0.2, 0.3, 0.4, 0.5, 1, 1.5, 2, 2.5, 3, 3.5, 4, 4.5 or 5 mm, optionally the bead comprises bead size of at most 4, 5, 6, 7, 8, 9, or 10 mm, optionally the pH of the beads is at least 2, 3, 4, 5, 6, or 7, optionally the pH of the beads is at most 6, 7, 8, 9, 10, 11, 12 or 13, optionally the beads are housed in a plurality of columns, optionally the columns arranged to produce a column effluent, optionally the plurality of columns are arranged in a series comprising at least a first column, a second column and a third column, and the solution flows through the columns sequentially to produce the column effluent, optionally the first column selectively binds to Au, Ag, Cu or Pb, the second column selectively binds to Au, Ag, Cu or Pb, and the third column selectively binds to Au, Ag, Cu or Pb, optionally before the wastewater contacts activated carbon.

As used in this disclosure, the term "gelificate" and its derivatives, as used herein, is defined as the process of turning a substance into a gelatinous form. This process comprises converting liquid substances into solids with the help of a gelling agent. Common gelling agents come from natural sources and include agar-agar, gelatin, carrageenan, gellan gum, pectin and methylcellulose.

In an embodiment, the biosorbent element is used in accord to the methods described herein. In another embodiment, the binding of a target metal includes contacting a solution containing a target metal with the biosorbent element described herein, and optionally separating the complex from the solution.

The present disclosure includes a system for binding a target metal comprising a biosorbent element described herein and activated carbon.

The systems, methods, uses and biosorbents disclosed herein can be applied to any microorganism. The systems, methods, uses and biosorbents disclosed herein are scalable at higher capacity.

It will be appreciated by a person skilled in the art that embodiments of the uses of the present disclosure can be varied as described herein for the methods of the present disclosure.

The following non-limiting Examples are illustrative of the present disclosure:

Example 1: Equilibrium and Kinetic Studies of Cu (II) and Ni (II) Biosorption on Non-Living *Euglena gracilis*

I. Introduction

Kinetic and sorption properties of dried *Euglena* cells were assessed in mono (Cu or Ni) and bi-metallic solutions (Cu+Ni) at metal concentrations typical of wastewaters (Gopalapillai et al., 2008; Mandavi et al., 2012). Kinetic modeling of metal sorption aids the design, optimization and commercial application of algal metal removal processes. Kinetic data describes the rate at which metal ions are taken up by the sorbent and therefore determines the residence time required for effective removal.

II. Experimental Procedures

A. Test Organism, Medium and Culture Conditions

*Euglena gracilis* Klebs were obtained from Boreal Laboratory Supplies Ltd (St. Catharines, ON, Canada). Non-axenic cultures were grown in medium consisting of 0.01 g·L$^{-1}$CaCl$_2$ (Bishop Canada Ltd), 1.0 g·L$^{-1}$CH$_3$COONa.3H$_2$O (Caledon Ltd, Canada), 1.0 g·L$^{-1}$ "Lab-Lemco", 2.0 g·L$^{-1}$ tryptone (Oxoid LDD, Basingstoke, Hampshire, England) and 2.0 g·L$^{-1}$ yeast extract (Oxoid LDD, Basingstoke, Hampshire, England). All media were prepared using Milli-Q water. The pH of the medium was adjusted using 1M HCl or NaOH after autoclaving and maintained between pH 3-5 at 20° C. in a Conviron (CMP5090) environmental chamber (Controlled Environments Ltd., Winnipeg, MB, Canada). *E. gracilis* were grown under a photoperiod of 18:6 (light:dark) at an intensity of 210 μmol·s$^{-1}$. To obtain non-living *Euglena*, post-harvest *Euglena* biomass was cooled to −80° C. (Forma Scientific, USA) for at least 24 h and subsequently freeze-dried (Lab-Conco, USA) for at least 48 h and milled. Glassware was immersed in 20% HNO$_3$ prior to use for at least 24 h and triple-rinsed with Milli-Q water to avoid metal contamination. In addition, any glassware used for culture growth was autoclaved to mitigate bacterial contamination.

B. Fourier Transform Infrared Spectroscopy (FTIR) Analysis

Dried biomass was analysed with attenuated total reflectance (ATR) using an ATR-FTIR spectrometer (Nicolet 380, Thermo, USA) in the absorbance mode (range: 4500-500 cm$^{-1}$) with 32 scans at a spatial resolution of 4 cm$^{-1}$.

C. Metal Solutions

Cu (II) and Ni (II) stock solutions (0.01 mol·L$^{-1}$) were prepared with CuSO$_4$.5H$_2$O (Caledon Laboratory Chemicals) and NiSO$_4$.6H$_2$O (BDH Chemicals), respectively. The pH of working metal solutions was adjusted with 0.1 mol·L$^{-1}$ HCl and 0.1 mol·L$^{-1}$ NaOH (Accumet, XL15, USA). Metal concentrations were determined utilizing inductively coupled plasma mass spectrometry (ICP-MS) (X Series II, ThermoScientific, USA). Rhodium was used as an internal standard. The accuracy of the ICP-MS measurements was assessed using SLEW-3, SLR-4, SLR-5, 1-BIS and 5-BIS certified reference material (National Research Council, Canada).

D. $Cu^{2+}$ and $Ni^{2+}$ Biosorption

The amount of $Cu^{2+}$ and $Ni^{2+}$ adsorbed at equilibrium, q (μg·g$^{-1}$) was calculated with the following equation:

$$q = \frac{(C_i - C_{eq})V}{m} \quad \text{(Equation 1)}$$

where $C_i$ is the initial concentration of the metal ion prior to adsorption (μg·L$^{-1}$) and $C_{eq}$ is the equilibrium concentration of metal ions in the aqueous phase. V is the volume (L) of the aqueous phase and m is the dry weight mass of the adsorbent (g). Each experiment was performed in duplicate and the results are presented as averages. All biosorption experiments were performed utilizing the batch technique.

E. Sorption Kinetics

Kinetics experiments were performed in duplicate at a constant temperature (20° C.) in 50 mL centrifuge tubes (Fisher Scientific) containing E. gracilis (1 g·L$^{-1}$) suspended in Milli-Q spiked with metal solutions of either Cu(II) and/or Ni(II). Kinetic studies were conducted at pH 5.0 and agitated at 70 rpm for 240 min. Kinetic studies were carried out for sorption of $Cu^{2+}$ and $Ni^{2+}$ as a function of contact time at four initial concentrations for each metal ($Cu^{2+}$=20 and 50 μg·L$^{-1}$, 1 and 25 mg·L$^{-1}$; $Ni^{2+}$=1, 2, 4, and 20 mg·L$^{-1}$) at pH 5 on non-living *Euglena gracilis*. Aliquots (7 mL) were removed from solution at pre-determined intervals over the time-course of the experiment, 0.7 μm-filtered (GFF, Merck Millipore, Ireland), acidified (ultrapure HNO$_3$ 70%) to pH 2.0 and metal concentrations were measured by ICP-MS. Adsorption kinetics models were used to evaluate the overall rate of Cu (II) or Ni (II) removal from *Euglena*-single metal solutions. Samples were taken at time intervals of 0, 10, 20, 30, 60, 90, 120, and 240 minutes. Two different, non-linear models were employed:

The pseudo-first-order kinetic equation (PFO; Lagergren, 1898):

$$q_t = q_e(1-e^{-kt}) \quad \text{(Equation 2)}$$

where $q_e$ is the amount of metal adsorbed (μg g$^{-1}$ or mg g$^{-1}$) at equilibrium, $q_t$ is the amount of metal adsorbed (μg g$^{-1}$ or mg g$^{-1}$) at time t, $k_1$ is the PFO equilibrium rate constant (min$^{-1}$) and t is contact time (min).

The pseudo-second-order kinetic equation (PSO; Ho et al., 1996):

$$q_t = \frac{q_e^2 k_2 t}{1 + q_e k_2 t} \quad \text{(Equation 3)}$$

where $q_e$ and $q_t$ are metal adsorbed at equilibrium and time t, respectively, $k_2$ is the PSO equilibrium rate constant, and t is contact time.

F. Sorption Equilibria

Sorption of Cu (II) and Ni (II) on living *E. gracilis* (1 g·L$^{-1}$) were examined in batch adsorption-equilibrium experiments in duplicate (120 min) at a constant temperature (20° C.) and agitated at 70 rpm. Blank trials without *Euglena* cells and trials without added metal solution were performed for each tested metal concentration. The pH levels of both mono- and bi-metallic solutions were maintained at 5.0 over the duration of the experiments with additions of 0.1 M HCl and/or 0.1 M NaOH. The effect of metal initial concentration was studied at pH 5.0 in mono-metallic solutions with values ranging from to 1.5 mg·L$^{-1}$ (Cu) and 5 μg·L$^{-1}$ to 1 mg·L$^{-1}$ (Ni). Bi-metallic solutions were prepared with initial $Cu^{2+}$ and $Ni^{2+}$ concentrations ranging from 10 μg·L$^{-1}$ to 6 mg·L$^{-1}$ and from 2 μg·L$^{-1}$ to 200 respectively. Metal concentrations were determined using ICP-MS. The Langmuir and Freundlich isotherm models were used to analyze biosorption data.

G. Statistics: t-Tests

Paired t-test analysis was used to evaluate differences in metal sorption between systems with different initial metal concentrations.

III. Results and Discussion

A. Characterisation of Dried *Euglena* Cells

The FTIR spectrum of dried *Euglena* cells (FIG. 1) showed different functional groups. The intense and strong bands at 3040 and 1640 cm$^{-1}$ were related to C—H and C=C in aromatic hydrocarbons. The stretching vibrations of 0-H (1700 cm$^{-1}$) and C—O (1380 cm$^{-1}$) were attributed to the carboxylic functional group. The C=O in amides was found at 1640-1660 cm$^{-1}$. Overall, dried *Euglena* cells possessed the main functional groups (e.g. carboxylic, amino and thiol) for metal binding.

B. Sorption Kinetics

Figure 2:
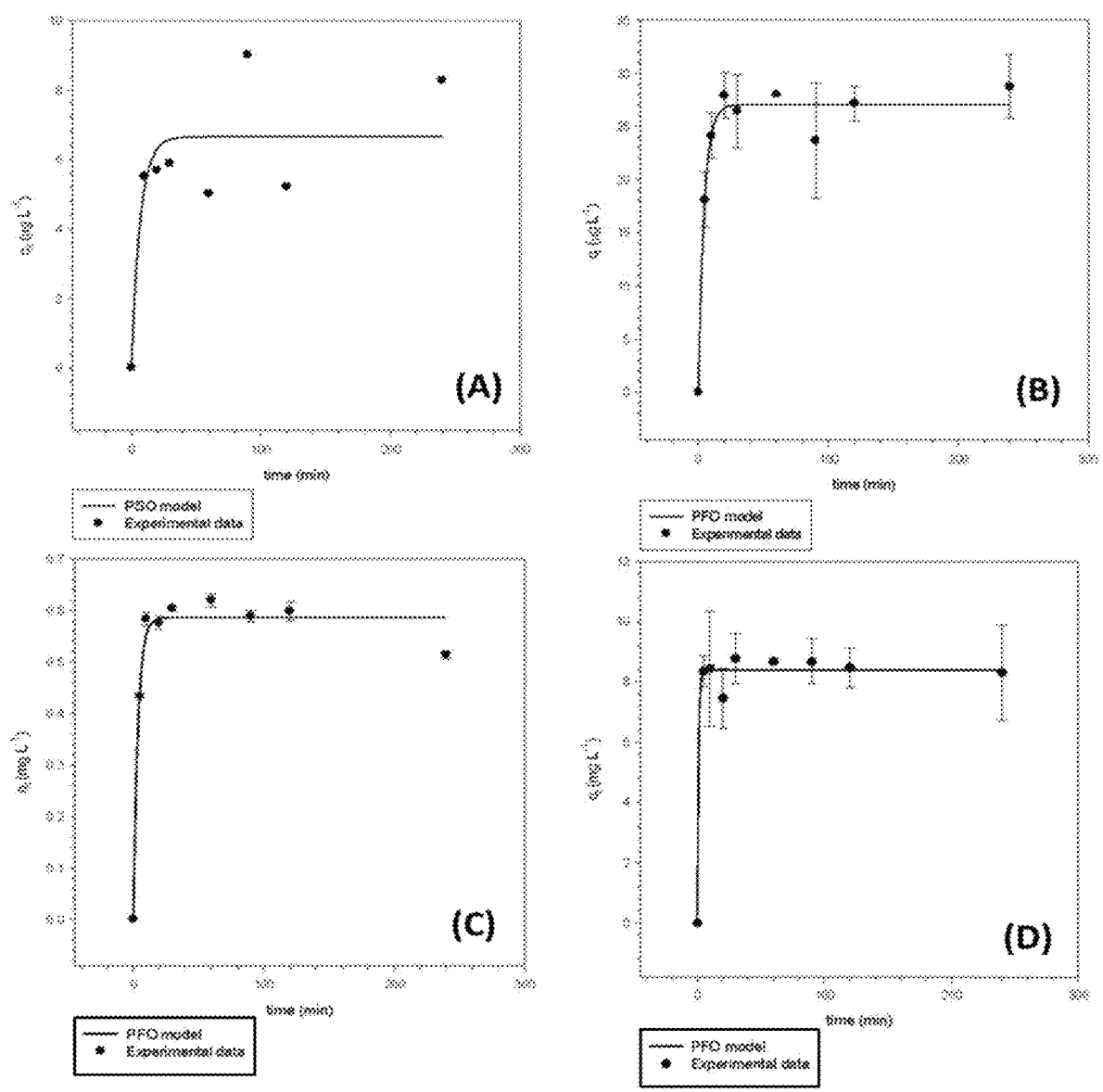
FIG. 2 shows $Cu^{2+}$ sorption kinetics on non-living *E. gracilis* at initial concentrations of (A) 20 ug·$L^{-1}$ and (B) 50 ug·$L^{-1}$ (C) 1 mg·$L^{-1}$ (D) 25 mg·$L^{-1}$. (A) and (C) show pseudo-first-order (PFO) kinetic model. (B) and (D) show pseudo-second-order (PSO) kinetic model.
Figure 3:
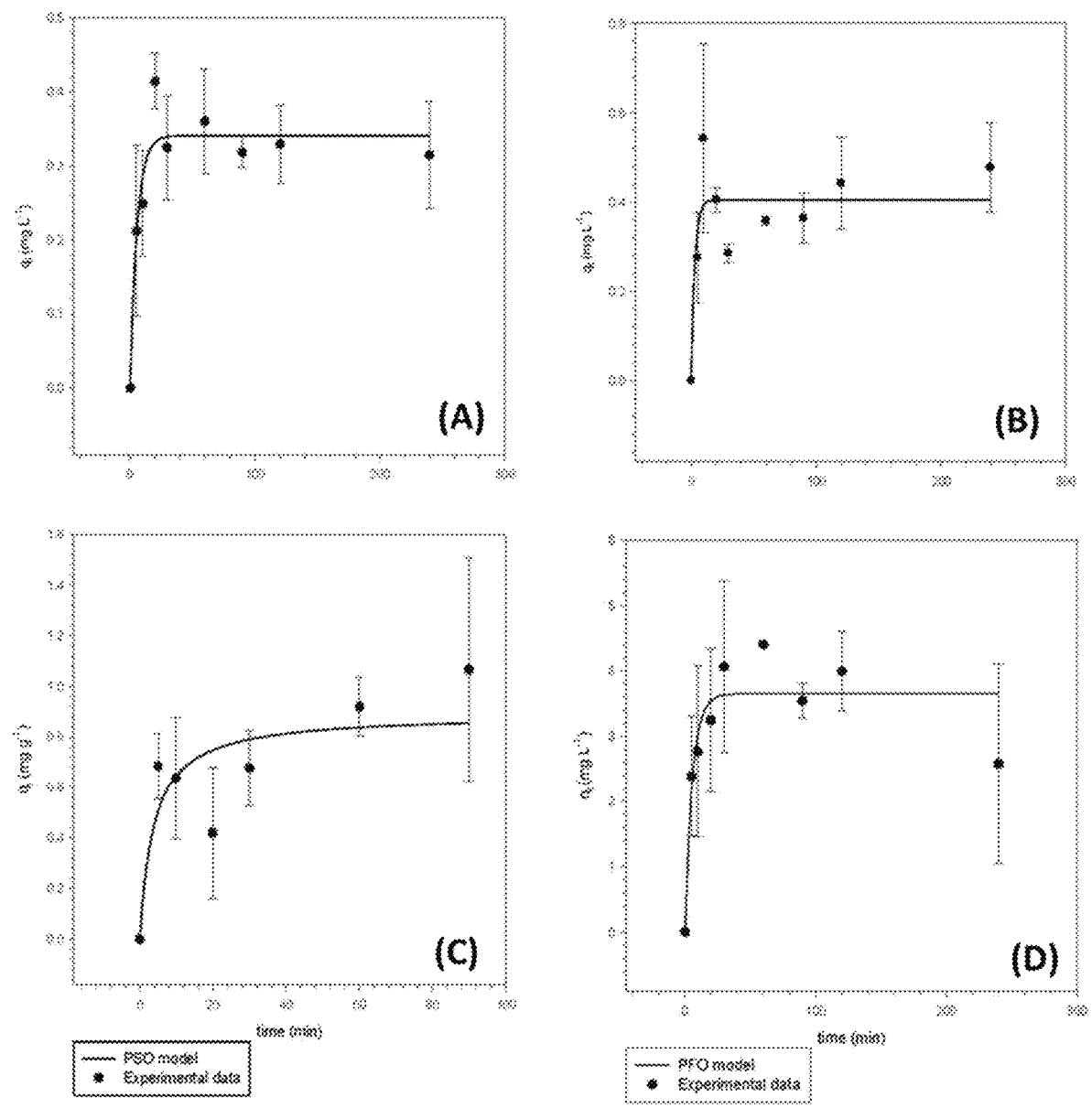
FIG. 3 shows $Ni^{2+}$ sorption kinetics on non-living *E. gracilis* at initial concentrations of (A) 1 mg·$L^{-1}$ and (B) 2 mg·$L^{-1}$ (C) 4 mg·$L^{-1}$ (D) 20 mg·$L^{-1}$. (A) and (C) show pseudo-first-order (PFO) kinetic model. (B) and (D) show pseudo-second-order (PSO) kinetic model.

Both metals (Cu and Ni) were found to adhere more closely to the PFO model (Table 1) congruent with previous non-living biomass studies (Liu et al., 2009; Rao et al., 2005). A strong agreement with the PFO model supported, while not wishing to be limited by theory, that the mechanism of adsorption was controlled by the physical attraction of metal ions onto unoccupied sites on the biomass as opposed to a process of chemisorption (e.g. agreement to the PSO model) in which metal ions share electrons with functional groups on the cell surface (Ho and McKay, 1998; Plazinski, 2013). Sorption of Cu and Ni to *Euglena* occurred relatively quickly within 10 to 30 min (FIG. 2 and FIG. 3) which indicates an attraction between the metals and the biomass. A strong affinity between sorbent and sorbate is an integral component of any application of biosorption to the remediation of metal-bearing effluent (Volesky, 2003). Using biological material to achieve metal removal requires a mass transfer of metal ions to the biomass from solution driven by a mutually attractive force (e.g. electrostatic, ion exchange). This affinity between *Euglena* biomass and metal ions is supported, while not wishing to be limited by theory, by the steep initial rise of the curves (FIG. 2 and FIG. 3). The PFO kinetic rate ($k_1$) generally increased as the initial concentration of metals was increased (Table 1 and Table 2). Previous biosorption studies have reported similar effects on kinetic constants while others have found higher values at lower concentrations (Cordero et al., 2004; Jaikumar and Ramamurthi, 2009). Amounts of metal sorbed in kinetic experiments were found to increase with initial metal concentration for both Cu and Ni (p<0.05). As the initial concentration of Cu increased from 0.02 mg·L$^{-1}$ to 25 mg·L$^{-1}$, metal loading also increased from 0.0066 mg·g$^{-1}$ to 8.40 mg·g$^{-1}$. Similarly, as Ni initial concentrations increased from 1 to 20 mg·L$^{-1}$, loading increased from 0.341 mg·g$^{-1}$ to 3.66 mg·g$^{-1}$ (Table 1 and Table 2). An increase in the initial concentration of Cu (~1250×) resulted in an approximately proportional increase (~1270×) in the amount of Cu sorbed to the biomass. In contrast, the amount of Ni sorbed increased ~12× concurrent with a 20× increase in initial concentration. A potential reason for this result could be that ligands which possess a high affinity for Cu are likely to contain N or S donor atoms (e.g. proteins, amino acids, thiols; FIG. 1) which tend to form stronger bonds with Cu as compared to other groups (Kiefer et al., 1997). Compared to other algal species, *Euglena* possesses higher proportions of protein and thiol structures which could contribute to the preferential sorption of Cu over Ni.

TABLE 1

Kinetic model parameters for the biosorption of Cu on non-living *Euglena gracilis* cells - pseudo-first order model.

| Initial concentration | $q_e$ (±SE) | $k_1$ | $r^2$ | % removal (±SE) |
|---|---|---|---|---|
| 20 µg/L | 6.65 µg/g (n = 1) | 0.147 | 0.725 | 43 |
| 50 µg/L | 27.0 µg/g (±0.647) | 0.224 | 0.974 | 65 (±2) |
| 1 mg/L | 0.587 mg/g (±0.014) | 0.287 | 0.974 | 60 (±1) |
| 25 mg/L | 8.40 mg/g (±0.157) | 1.03 | 0.981 | 34 (±5) |

TABLE 2

Kinetic model parameters for the biosorption of Ni on non-living *Euglena gracilis* cells - pseudo-first order model.

| Initial concentration | $q_e$ (±SE) | $k_1$ | $r^2$ | % removal (±SE) |
|---|---|---|---|---|
| 1 mg/L | 0.341 mg/g (±0.016) | 0.182 | 0.913 | 38 (±7) |
| 2 mg/L | 0.406 mg/g (±0.034) | 0.339 | 0.742 | 22 (±4) |
| 4 mg/L | 0.752 mg/g (±0.106) | 0.410 | 0.648 | 8 (±3) |
| 20 mg/L | 3.66 mg/g (±0.242) | 0.175 | 0.840 | 13 (±8) |

C. Sorption Equilibria

Figure 5:
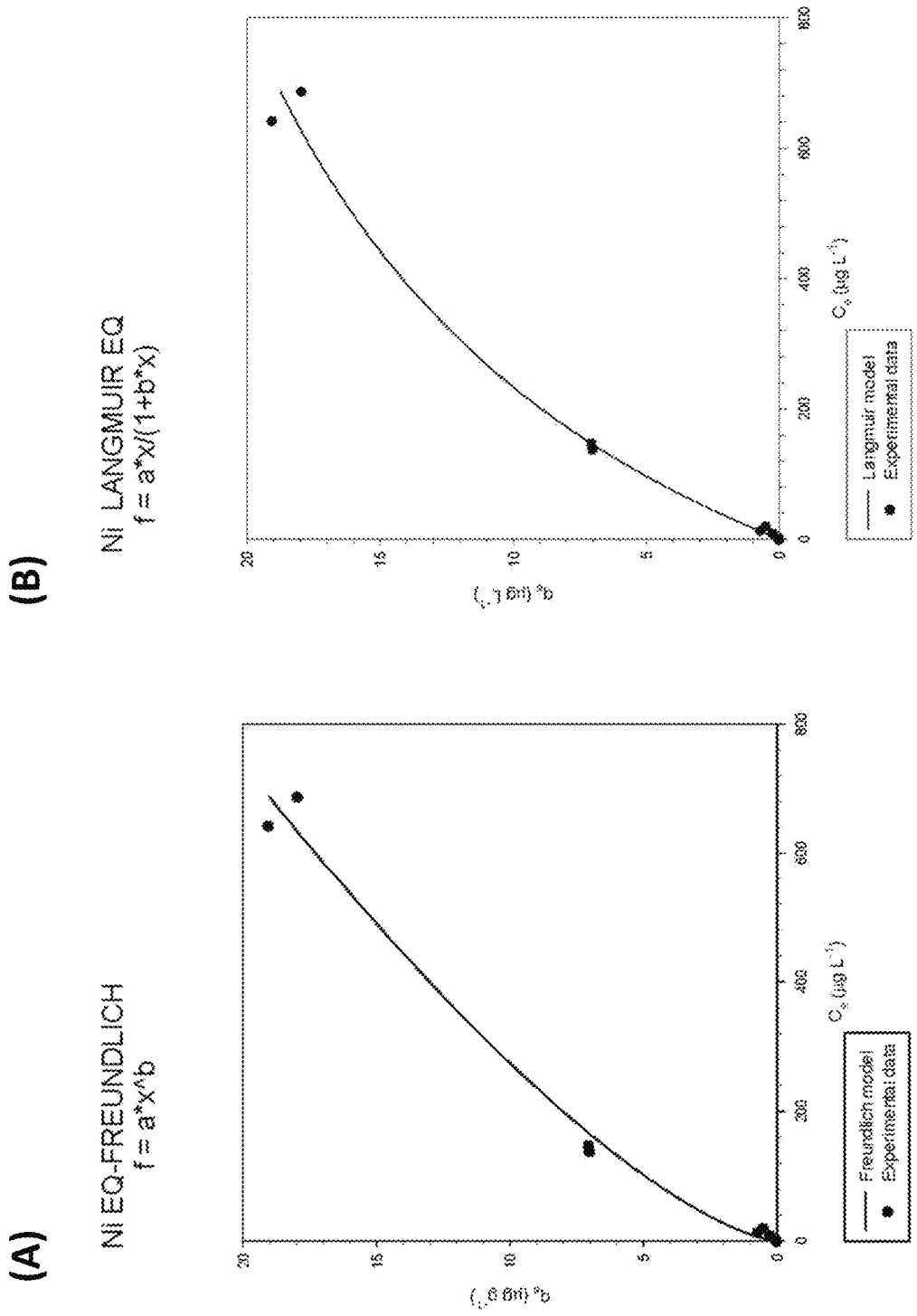
FIG. 5 shows $Ni^{2+}$ sorption equilibrium on non-living *E. gracilis*. (A) shows Freundlich model and (B) shows Langmuir model.

In this disclosure, the biosorption of $Cu^{2+}$ and $Ni^{2+}$ was evaluated at industrially relevant (e.g. wastewater which has undergone primary treatment) concentrations (e.g. ≤25 mg·L$^{-1}$). The biosorption of both $Cu^{2+}$ and $N^{2+}$ in single-metal solutions increased with increasing equilibrium concentration (FIG. 3 and FIG. 4). The degree of fit ($r^2$) to both the Langmuir and Freundlich models indicated that the sorption of Cu (0.995 and 0.985, respectively) and Ni (0.996 and 0.985, respectively) by non-living *Euglena gracilis* can be described appropriately by either model (p<0.001; both metals and models; Table 3, Table 4, FIG. 4 and FIG. 5). However, the higher $r^2$ for the Langmuir model compared to Freundlich indicated that metal ions were being adsorbed in a monolayer with functional groups on the surface of the biomass (Rao et al., 2005). The comparatively high applicability of the Freundlich model supports that sorption also may occur on heterogeneous surfaces on the cell. Comparable Langmuir parameters (k and $q_{max}$) were found for both metals (p>0.05; Table 3). The maximum capacity for biosorption was 89.6 µg/g and 34.1 µg/g for Cu and Ni respectively. Despite differences in metal concentrations, Langmuir parameters (e.g. $q_{max}$ and b) were analogous to previous studies (Chen et al., 2008; Rao et al., 2005). The values of k ranged from 556 to 625 for Ni and Cu, respectively, with no significant differences between metals (p>0.05) (Table 3).

TABLE 3

Langmuir adsorption isotherm parameters for the biosorption of Cu and Ni on non-living *Euglena gracilis* cells at pH 5.

| Metal | k | $q_{max}$ µg g$^{-1}$ | $r^2$ | % Removal |
|---|---|---|---|---|
| Cu | 625 | 89.6 (83.1 · 99.2) | 0.995 | 49 (±12) |
| Ni | 556 | 34 (31.3 · 37.1) | 0.996 | 32 (±7) |

TABLE 4

Freundlich adsorption isotherm parameters for the biosorption of Cu and Ni on non-living *Euglena gracilis* cells at pH 5.

| Metal | $K_f$ | 1/n | $r^2$ | % Removal |
|---|---|---|---|---|
| Cu | 0.502 | 0.697 | 0.985 | 49 (±12) |
| Ni | 0.196 | 0.700 | 0.989 | 32 (±7) |

Figure 6:
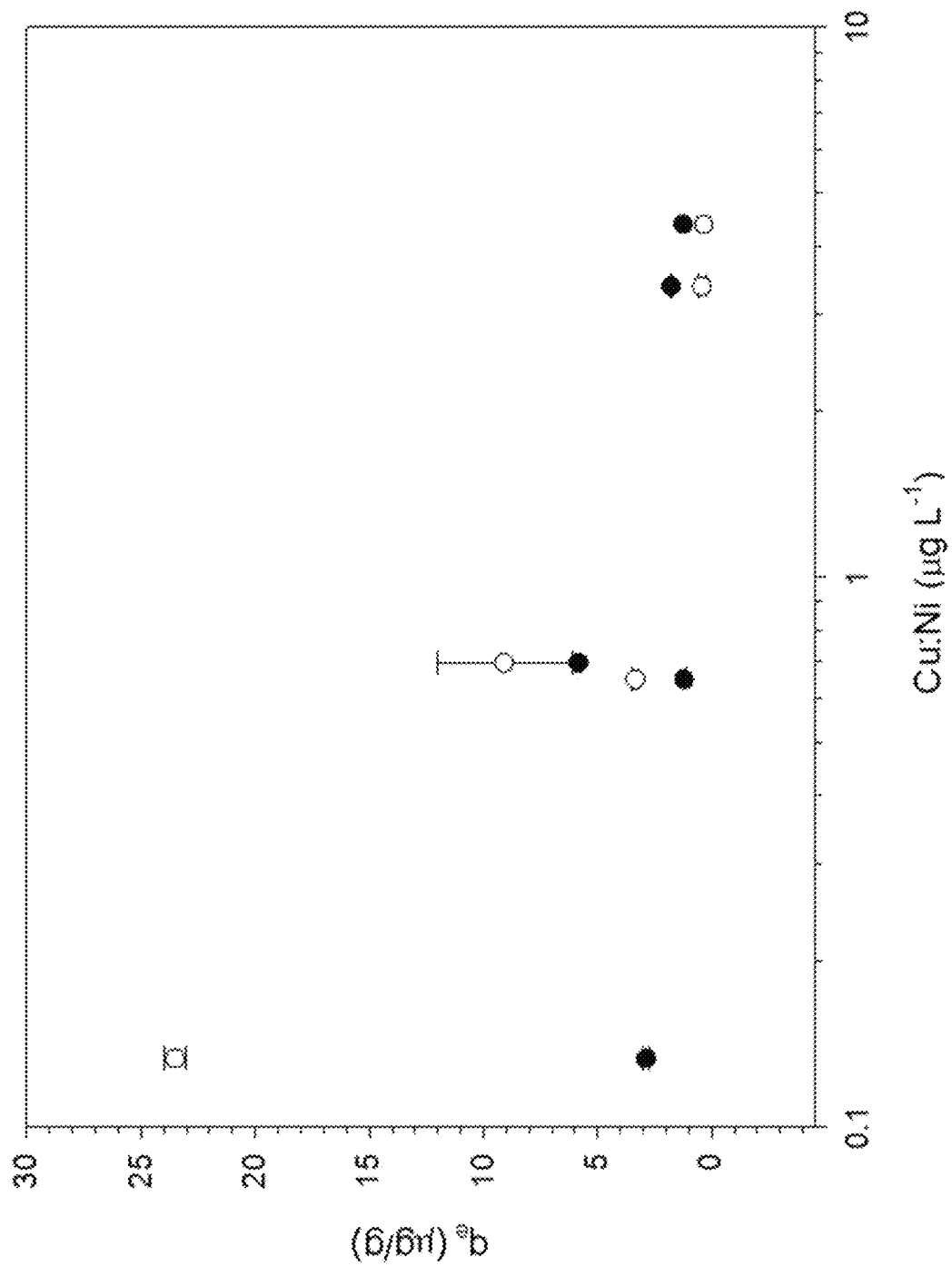
FIG. 6 shows $Cu^{2+}$ and $Ni^{2+}$ sorption equilibrium from binary-metal solution on living *E. gracilis*. Error bars represent SE. $Cu^{2+}$ in closed circle and $Ni^{2+}$ in open circle.

The biosorption of Cu and Ni was also examined in binary metal solutions to better emulate the mixed composition of industrial wastewaters (FIG. 6). Sorption was assessed as a function of the ratio of the initial concentrations of Cu to Ni. When compared to single-metal solutions, Cu and Ni total metal uptake did not differ significantly in terms of sorption capacity as a function of initial metal concentrations (p>0.05). At Cu:Ni<1, Ni sorption was greater than Cu (p<0.05; FIG. 6) whereas at Cu:Ni>1Cu sorption was higher (p<0.05). This contrasts with live *Euglena* cells wherein Cu and Ni uptake was similar between Cu:Ni ratios (p>0.05) (Winters et al., 2016). Ni sorption was suppressed at high concentrations of Cu (Cu:Ni>1) whereas the opposite occurred at relatively higher Ni levels, which supports, while not wishing to be limited by theory, an antagonistic biosorption competition between Cu and Ni ions for commonly shared binding sites. The equilibrium uptake ($q_e$) of Ni decreased with the increasing quantity of Cu ions. The antagonistic effect of Cu ions on the equilibrium Ni uptake was dominant at higher initial Cu concentrations.

IV. Conclusions

This Example assessed metal sorption at typical concentrations (<100 mg·L$^{-1}$) found in industrial wastewaters after a primary form of treatment. To our knowledge, this is the first instance in which *Euglena* has been studied for this purpose. Non-living *Euglena gracilis* has been shown to demonstrate comparable biosorption capacities (34-89 µg g$^{-1}$) as other eukaryotic organisms in the removal of Cu and Ni from aqueous solutions. FTIR analysis indicated the presence of functional groups (e.g. carboxyl, amide) which have been previously identified as important metal binding sites for metal biosorption. Sorption kinetics followed the PFO model supporting, while not wishing to be limited by theory, a physically-based form of biosorption. Both the kinetic rate ($k_1$) and the amount of metal sorbed were found to rise with increasing initial concentration. Although sorption occurred rapidly (10-30 min), Cu was more efficiently taken out of solution than Ni. In single-metal solutions both Cu and Ni were found to exhibit a greater degree of fit to the Langmuir model which supports, while not wishing to be limited by theory, that metal ions bind to uniform sites on the cell surface in a monolayer. Similarly to kinetic results, Cu sorption was found to be greater in single-metal solutions than Ni although *Euglena* exhibited a similar affinity for both metals. Langmuir parameters were found to be comparable to sorption of Cu and Ni by similar organisms. In binary-metal systems, sorption of Cu was suppressed at relatively high concentrations of Ni and conversely, Ni sorption was inhibited at higher (e.g. >10) Cu:Ni ratios. As to be shown next in Example 2, the removal potential of non-living *Euglena*, whether dried or wet, was conducted using actual multiple metals-containing water from a mining operation.

Example 2A: Multiple Metals Bind to Spherificated Wet *Euglena* Biomass, Dried *Euglena* Biomass and *Euglena* Exudates I. Introduction The recovery of gold from water in mining operation is of significant interest to the mining industry. Mining operation often utilizes a carbon filtration system to recover gold in their process. An issue with this method is the reduced efficiency of the carbon filter by the presence of copper, which is preferentially bound by the filter, thereby reducing the recovery of gold from the water. The strategy employed by in this study was to use the *Euglena*-based platform to remove the copper from the water prior to carbon filtration, thereby improving the yield of gold via carbon filtration.

Several different forms of the *Euglena* platform were tested for their ability to bind heavy metals from mining process water samples. The mining process is an open pit CN leaching operation. The mining process water and in this Example is between pH of 9-11, and contains between 100-800 ppm total CN. *Euglena gracilis* has the ability to secrete dissolved organic materials in response to heavy metal stress. These dissolved organic materials are constituents of the exudates that can potentially bind and de-toxify the heavy metals in solution. Spherification of *Euglena* or exudates of *Euglena* provides a greater and more concentrated surface area for metal binding and also provides a method for the removal of the *Euglena* and the bound metals after the incubation period. In this Example, both live and non-living *Euglena* were tested for their ability to remove metals by incubating the cells within the mining process water. Further, spherificated *Euglena*-based platform including spherificated exudates of *Euglena* were also tested for their ability to bind metals.

II. Experimental Procedures

A. Preparation of Wet *Euglena* Biomass, Dried *Euglena* Biomass and Exudates of a Culture of *Euglena*

*Euglena gracilis* was grown in media and harvested by solid liquid separation using centrifugation, where the wet solid biomass was retained, and the media discarded. Dried *Euglena* cells were obtained by drying the biomass.

For the collection of exudates, instead of discarding the media as above, the exudates were recovered from media taken from the *Euglena* culture. 5 mL of media was used to obtain 50 mg of dry weight of media containing the exudates.

B. Spherification Process

The spherification process involves using a sodium alginate solution to encapsulate the *Euglena* biomass and the exudates of *Euglena*. This provides a greater and more concentrated surface area for metal binding and also provides a method for the removal of the *Euglena* and the bound metals after the incubation period. The "Sphered" wet *Euglena* biomass, dried *Euglena* biomass, as well as exudates, i.e. spent media that *Euglena* grew in, were spherificated in this study. The "Free" wet *Euglena* biomass, dried *Euglena* biomass, and *Euglena* exudates are materials that have not been spherificated.

The spherification process involves mixing media containing wet *Euglena* biomass, dried *Euglena* biomass, or exudates of a culture of *Euglena* with an equal volume of 4 $g \cdot L^{-1}$ sodium alginate solution. This mixture is dripped into a gently stirring solution of chilled 2 $g \cdot L^{-1}$ $CaCl_2$. Upon contact with the $CaCl_2$ solution, the droplets form spheres. Once the mixture being encapsulated has been exhausted and the spheres have formed, the spherificated materials are poured through a strainer and stored in a closed vessel until used.

C. Metals Binding

The "Free" *Euglena* treatments were prepared by using 1.5 g (dry weight) sample of either wet *Euglena* biomass, dried *Euglena* biomass, or exudates of a culture of *Euglena*. This quantity was then mixed with the mining process water sample for 24 hours after which the sample was poured through a 5 μm filter and submitted for inductively-coupled plasma optical emission spectrometry (ICP-OES) analysis.

The "Sphered" *Euglena* treatments were prepared by using 1.5 g (dry weight) sample of either wet *Euglena* biomass or dried *Euglena* biomass, which was spherificated as described above. For the Sphered exudates, 50 mg of media containing the exudates (dry weight) in which the *Euglena* had been growing in was spherificated using sodium alginate via the standard procedure for spherification as described above. The spheres produced were mixed with the processing mining water sample for 24 hours, after which the sample was poured through a 5 μm filter and submitted for ICP-OES analysis.

D. Preparation and Determination of Metals Complexed by *Euglena* and *Euglena* Exudates Preparation and determination of multiple metals in samples treated with the *Euglena* platform were carried out at the Lakefield Laboratory of SGS Minerals Services Geochemistry (SGS). Samples in aqueous CN process solutions were acidified with HCL, $HNO_3$ and $H_2O_2$, and then diluted into 20% hydrochloric acid. Diluted acidified solutions were analyzed by the Varian Vista ICP-OES system. Quality controls included one method blank, one sample replicate and two calibration check solutions analyzed with every batch of 24 samples or less.

E. Preparation and Determination of Au Complexed by *Euglena* and *Euglena* Exudates Preparation and determination of gold in samples treated with the *Euglena* platform were carried out at the Lakefield Laboratory of SGS Minerals Services Geochemistry. Gold present in a solution sample of CN or acid based matrix, plus an inquart of silver nitrate are fire assayed using Pb flux and cupelled to produce a doré bead. The bead was dissolved using HCl and $HNO_3$ and the resulting solution was submitted for analysis. Gold content was analyzed by flame atomic absorption spectrometry (AAS) using acid matrix matched calibration materials. Quality controls included one method blank per 7 samples; 1 duplicate per 7 samples; 1 sample spike taken through the digestion per batch; and calibration materials that cover the linear range.

III. Results and Discussion

A. Binding of Multiple Metals by Spherificated *Euglena* Exudates

The results in Table 5 show amounts of various metals in samples treated with different forms of the *Euglena* platform compared to the untreated water (Control 1 & 2). Values are showing the amount of metals remain in solution after treatment. On average the level of gold in the control samples was 0.136 mg·L$^{-1}$. A promising result with this platform was that the gold concentration was reduced by only 6% across all variants of the *Euglena* platform (Avg. 0.128 mg·L$^{-1}$). In contrast, the levels of copper are markedly reduced compared to the controls, regardless of the platform variant used. On average the *Euglena* treatments removed ~82% of the copper from the water samples. The high copper binding capacity of various forms of the *Euglena* platform in process water obtained from an actual mining operation which contains multiple metals shows a practical application of the *Euglena* platform described herein.

TABLE 5

Multiple metals binding to spherificated wet *Euglena* biomass, dried *Euglena* biomass, and exudates of a culture of *Euglena gracilis*.

| | | | Sample | | | | |
|---|---|---|---|---|---|---|---|
| Element (ppm) | Control (1) | Control (2) | Sphered *Euglena* (Wet) | Free *Euglena* (Wet) | Sphered *Euglena* (Dried) | Free *Euglena* (Dried) | Sphered Exudates |
| Au | 0.134 | 0.138 | 0.127 | 0.129 | 0.13 | 0.13 | 0.129 |
| Ag | 0.0527 | 0.0501 | 0.073 | 0.124 | 0.0499 | 0.0609 | 0.184 |
| Al | 3.53 | 3.35 | 0.08 | 0.004 | 0.024 | 0.025 | 0.034 |
| As | 0.0158 | 0.0154 | 0.0031 | 0.0031 | 0.0025 | 0.003 | 0.0038 |
| Ba | 0.0312 | 0.0296 | 0.00862 | 0.0137 | 0.112 | 0.0739 | 0.00781 |
| Be | 0.000115 | 0.000107 | <0.000007 | <0.000007 | <0.000007 | <0.000007 | <0.000007 |
| B | 0.333 | 0.345 | 0.341 | 0.349 | 0.376 | 0.369 | 0.552 |
| Cd | 0.0167 | 0.0151 | 0.000879 | 0.000668 | 0.000448 | 0.000506 | 0.000812 |
| Cr | 0.00525 | 0.00533 | 0.00195 | 0.00103 | 0.00096 | 0.00099 | 0.00181 |
| Cu | 223 | 208 | 37.7 | 39.2 | 35.1 | 40.8 | 31.5 |
| Fe | 4.74 | 4.68 | 0.126 | 0.01 | 0.008 | 0.014 | 0.055 |
| Mg | 37.6 | 38.2 | 35.6 | 49.9 | 36.1 | 38.2 | 61.9 |
| Mn | 0.33 | 0.306 | 0.0135 | 0.00679 | 0.00161 | 0.00462 | 0.0192 |
| Mo | 1.83 | 1.86 | 1.77 | 1.83 | 1.71 | 1.77 | 1.68 |
| Na | 2060 | 2040 | 1970 | 2060 | 1980 | 2040 | 2010 |
| Ni | 0.155 | 0.16 | 0.161 | 0.167 | 0.16 | 0.148 | 0.143 |
| Pb | 0.0442 | 0.0384 | 0.00112 | 0.00005 | 0.00021 | 0.00016 | 0.00074 |
| Se | 1.31 | 1.27 | 0.833 | 0.86 | 0.818 | 0.823 | 0.821 |
| Sr | 0.665 | 0.667 | 1.62 | 0.631 | 0.864 | 0.598 | 11.4 |

A key performance metric of the different treatments is to compare the Ratio of the Weight of the Active Material to Weight of Copper Removed (Table 6). Both "Free" wet *Euglena* biomass or dried *Euglena* biomass, as well as the "Sphered" wet *Euglena* biomass or dried *Euglena* biomass showed similar relationships, with ratios in the range of 53.2:1 to 54.9:1.

TABLE 6

Weights of Active Materials and Effectiveness in Removing Metals by Free and Sphered wet *Euglena* biomass, dried *Euglena* biomass and exudates (media) of a culture of *Euglena gracilis*.

| Treatment | Weight of Active Material (mg) | Initial Weight of Copper in 150 mL of Solution (mg) | Final Weight of Copper (mg) | Weight of Removed Copper (mg) | Ratio of Weight of Active Material to Weight of Copper Removed | Copper Removed From Solution (%) |
|---|---|---|---|---|---|---|
| Free *Euglena* (Wet) | 1500 | 33.5 | 5.9 | 27.6 | 54.4:1 | 82% |
| Free *Euglena* (Dry) | 1500 | 33.5 | 6.1 | 27.3 | 54.9:1 | 82% |
| Sphered *Euglena* (Wet) | 1500 | 33.5 | 5.7 | 27.8 | 54.0:1 | 83% |
| Sphered *Euglena* (Dry) | 1500 | 33.5 | 5.3 | 28.2 | 53.2:1 | 84% |
| Sphered Media | 50 | 33.5 | 4.7 | 28.7 | 1.7:1 | 86% |

The most successful treatment with respect to this ratio was the Sphered exudates (labeled as "Sphered Media" in Table 6), which showed a ratio of 1.7:1. This result demonstrated that the Sphered exudates performed ~31× better than Free wet or dried *Euglena* biomass, as well as Sphered wet or dried *Euglena* biomass.

All of the treatments (Table 6) showed removal rates of 82% to 84% (of copper), which supports, while not wishing to be limited by theory, the spherification process has a minimal impact on the removal of the copper (and other metals according to Table 5).

Other metals and metalloids of note that have been removed are aluminum (~98%), arsenic (~0.80%), cadmium (~95%), chromium (~75%), iron (>99%), manganese (~96%), lead (>99%) and selenium (~35%).

IV. Conclusions

Using "Free" wet or dried *Euglena* biomass or "Sphered" wet or dried *Euglena* biomass to capture copper from process water sample gives an 82-84% removal of copper. The ratio of the Weight of Active Material to the Weight of Copper Removed is between 53.2:1 and 54.9:1.

Sphered exudates removes 86% of the copper in the process water sample, and is useful in a 1.7:1 ratio of Weight of Active Material to Weight of Copper Removed; this is ~31× better than when compared to either the Free *Euglena* biomass or the Sphered *Euglena* biomass ratios.

Metal binding capacities of free and sphered *Euglena* exudates are comparable. The main benefit of using the sphered *Euglena* exudates is the ease of removal of complexes after metals have bound to the materials. To recover the metal-bound complexes, handlers are not required to centrifuge the samples post-treatment. This saves time, energy and reduces the risk for the accidental release of the captured metals during sample handling.

Example 2B: Selective Metals Binding to *Euglena* Exudates and *Euglena* Biomass Subjected to Different Post-Harvest Treatments Prior to Spherification I. Introduction As shown above in Example 2A, spherification of *Euglena* provides certain advantages in metals recovery. Next, the functionality of differently generated beads as a binding agent for Au, Ag, Pb and Cu in three scenarios is disclosed. In the first scenario, tests determined if columns containing *Euglena*-beads could operate downstream of carbon column or in the excess pond in order to capture the Au that passed through the carbon column. The second scenario tested whether the columns containing *Euglena*-beads could improve the selective Au binding properties of the carbon columns by functioning upstream to remove Cu and Pb. Finally, tests explored whether the columns containing *Euglena*-beads could function as the primary Au recovery method and completely replace the carbon column. Ten variations of beads were prepared at various drying, heating and pH levels, loaded into columns, and tested. In total, over fifty trials were conducted at different sites.

Post-harvest treatments prior to spherification optionally affect binding capacity of *Euglena* biomass or exudates of a culture of *Euglena*. In the present disclosure, different post-harvest treatments of *Euglena* biomass are found to affect the capacity of active materials in binding to different metals and the degrees of removal of different metals.

II. Experimental Procedures

A. Site Selection and Sample Collection

Figure 7:
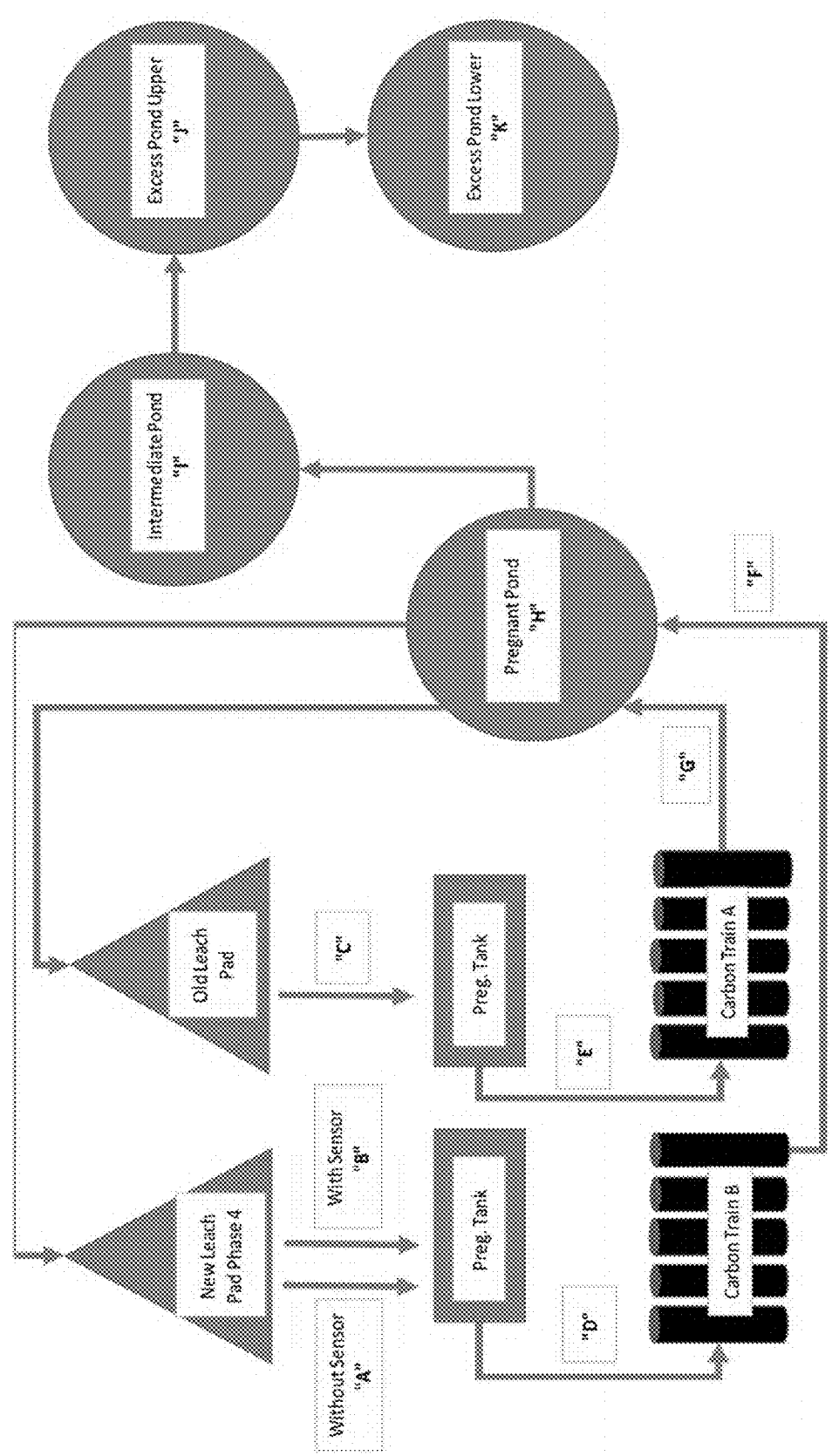
FIG. 7 shows sample sites.

Eleven different sites (A to K) throughout a mining operation were selected to represent all possible water chemistries existing on the mining operation (FIG. 7). The variety of samples were chosen to determine how various water chemistries affected bead performance.

B. Bead Preparation

The biochemicals used in this study were derived from *Euglena gracilis* based on standard fermentation and utilizes sugar as a carbon source. To allow for ultimate flexibility and co-production with other materials at scale-up, no "directed expression" techniques were used to achieve biochemical selectivity. Instead, treatment of the biochemical after extraction was attempted.

Biochemicals were derived either from the insoluble fraction of the biomass or from their soluble secreted materials (i.e. exudates). These materials were isolated and then processed with various techniques, to attempt to create material with preferential binding to a specific metal. Sodium alginate was selected to create a matrix that would hold the biochemicals when binding metals.

For beads made with harvested *Euglena* cells, an equivalent weight of 100 g (dried material) of the *Euglena* biomass, 100 g of heated material is brought to 1 L with deionized water (DI) water. This mixture is blended thoroughly to which 6 g of sodium alginate is added. This mixture is once again blended thoroughly for a period of 5 minutes or more.

The resulting mixture is then dripped into 2 L of a 4 g·L$^{-1}$ chilled $CaCl_2$ solution with stirring. Upon contact with the $CaCl_2$ solution, the beads are formed. Once all of the slurry has been dripped into the $CaCl_2$ mixture, the resulting beads are strained of excess solution and then stored in a sealed container.

For beads made with exudates of a culture of *Euglena* cells, an equivalent weight of 2.4 g dried material contained in 1 L of liquid is blended thoroughly with 6 g of sodium alginate for 5 minutes or more. This mixture is then dripped into a $CaCl_2$ solution as described above to form beads. To concentrate the exudates of *Euglena*, liquid containing the exudates is evaporated off in a rotovap at 70° C. until the volume has been reduced by 2.5×. For beads made with this concentrated exudates, an equivalent weight of 6 g dried material contained in 1 L of liquid is blended thoroughly with 6 g of sodium alginate for 5 minutes or more. This mixture is then dripped into a $CaCl_2$ solution as described above to form beads.

Alternatively, either of the mixtures from above is envisioned to be spherificated, gelificated, encapsulated or immobilized with material that will allow the diffusion of metal barring solutions through them while retaining the material to be encapsulated. The desired form of the encapsulated material is spherical to maximize surface area of the said beads.

In total, ten bead variations were tested to determine efficacy and if preferential selectivity to any of the metals was exhibited (Table 7). *Euglena* biomass (EE) was not encapsulated and was used as a control. Bead size (3 mm and 5 mm) was also varied to see if surface area had an effect on binding chemistry. Exudates of a culture of *Euglena* cells were encapsulated to examine concentration and the effect of increased surface area on the performance of the technology. Biomass derived biochemicals were then dried (50° C.) and heat-treated (80° C., 120° C.) to explore if this influenced the binding preference to Au (similar to activated carbon). Biomass derived biochemicals were also prepared at varying pH (4, 6, 7) to explore the effect of pH on binding chemistry.

TABLE 7

Trial conditions and variables.

| Bead Name | Description of Material | Bead Size | pH | Temperature Treatment |
|---|---|---|---|---|
| WBS | Wet Biomass Biochemicals | 3 mm | 6 | — |
| WB4 | Wet Biomass Biochemicals | 5 mm | 4 | — |
| WB6 | Wet Biomass Biochemicals | 5 mm | 6 | — |
| WB7 | Wet Biomass Biochemicals | 5 mm | 7 | — |
| DB50 | Dry Biomass Biochemicals | 3 mm | 6 | 50° C. |
| DB80 | Dry Biomass Biochemicals | 3 mm | 6 | 80° C. |
| DB120 | Dry Biomass Biochemicals | 3 mm | 6 | 120° C. |
| SB | Secreted Biochemicals | 5 mm | 6 | — |
| CSBS | Concentrated Secreted Biochemicals (Exudates) | 3 mm | 6 | — |
| CSBL | Concentrated Secreted Biochemicals (Exudates) | 5 mm | 6 | — |
| EE | *Euglena* not Encapsulated | — | — | — |

C. Standard Column Operation

The standard single column operation was performed by loading approximately 50 mL of the bead material into a column (FIG. 8A). Deionized water was pumped through the column to wash the bead material. The column was positioned so that the sample traveled up from the bottom of the column and out through the top. The sample was pumped through the column at a rate of 1 bed volume (BV) per 5 minutes. At each 5-minute interval, a sample was taken to compare how the composition of the water changed from the beginning of the process. The column was run for 3 BV to test total percentage removal.

The single column operation was performed with bead type WBS at all sites to test how the water chemistry affected bead performance; all bead types were also tested at site K. Selected beads (WBS, WB6, DB50, DB120, SB) were tested at sites A and F to explore the effect of bead type on performance. These sites were upstream and downstream of the carbon columns and had diverse metal and CN concentrations. Activated carbon was tested at site A and site K, with and without un-encapsulated *Euglena* as a pretreatment.

D. CN Destruction and pH Adjustment

A sample of process water was treated with an excess of hydrogen peroxide ($H_2O_2$) to facilitate the destruction of CN in the sample. Since metal ions might precipitate from the solution, a small amount of acid was added to keep the pH above 4.

The process water was initially tested in its unaltered state, and then secondly with the addition of $H_2O_2$, and finally with a constant pH of 4. These tests were done to determine how to maximize column performance. By maintaining a pH of 4, it could be determined whether the pH had a positive effect on the column.

E. Column Series Operation

A column series operation works in the same manner as a single column operation, however, two or more columns are connected in a series, with each column containing a different type of bead, or in another variation, a column of activated carbon is included in the series (FIG. 8B). The system is operated in the same way as the standard column operation, except that the first BV is taken after multiplying the number of columns being used by 5 (5 minutes for each column to process a BV). For instance, if 3 columns are connected in a series, the system must run for 15 minutes to collect a sample that has passed through the whole system.

Multiple series were tested with different bead and/or carbon combinations for sites A and K. The beads were collected to examine the distribution of metal in the series. The objective was to determine if the series could either increase the performance of the carbon column, or replace it.

F. Water Analysis

The process water sample was tested with an Atomic Absorption Spectrophotometer (AAS) before it was introduced to the column(s) to determine the concentrations of the metals of interest. After each bed volume of pond sample was passed through the column, a sample was collected and again tested using the AAS. The difference between the initial concentration and the concentration after processing each bed volume of each sample was calculated and expressed as a percentage removal. When multiple bed volumes of sample were processed, the average percentage removal was reported.

G. Assaying of Metal on Beads

The bead material from the experiments was collected and sent to SGS for analysis. SGS dried the beads and then dissolved them in aqua regia (a very strong acid). The resulting solution was analyzed on the AAS that gave the concentration of metal per kg of dry bead. This was done to test the loading and selectivity of the bead columns and carbon columns.

III. Results and Discussion

A. Site Selection and Analysis

Samples were taken from eleven different sites throughout the mining operation to determine how various water chemistries impacted the bead performance (FIG. 7). As expected, each site possessed varying concentrations of Au, Ag, Cu and Pb, as well as varying pH and CN levels (Table 8).

TABLE 8

Chemical compositions of samples.

| | Concentration (ppm) | | | | | | |
|---|---|---|---|---|---|---|---|
| Site | Au | Ag | Cu | Pb | Free CN | Total CN | pH |
| A | 1.03 | 0.53 | 374 | 15.6 | 90 | 334 | 11.9 |
| B | 0.48 | 1.19 | 500 | 8.95 | 170 | 552 | 11.9 |
| C | 0.59 | 0.89 | 432 | 0.28 | 130 | 462 | 11.0 |
| D | 0.71 | 0.94 | 459 | 12.7 | 500 | 711 | 11.9 |
| E | 0.34 | 0.82 | 431 | 0.55 | 620 | 717 | 11.1 |
| F | 0.16 | 0.54 | 440 | 7.68 | 570 | 674 | 11.9 |
| G | 0.15 | 0.55 | 428 | 0.36 | 530 | 717 | 11.1 |
| H | 0.35 | 0.72 | 360 | 0.91 | 250 | 472 | 10.1 |
| I | 0.27 | 0.39 | 323 | 0.42 | 140 | 361 | 9.8 |
| J | 0.27 | 0.54 | 244 | 0.18 | 0 | 109 | 9.1 |
| K | 0.25 | 0.49 | 242 | 0.14 | 0 | 133 | 9.1 |

The highest concentrations of Au and Ag were observed directly off the leach pads (A, B, C) and prior to the column trains (D, E), while the lowest concentrations were observed after the carbon trains (F, G). There was a slight increase in concentration at the pregnant pond (H), but again lower amounts by the excess ponds (I, J, K).

The concentration of both Cu and Pb significantly decreased from the first stages (A, B, C) to the end (J, K) of the process. The same phenomenon was observed with pH levels, as they tended to decrease from beginning to end (starting as high as 11.9 pH and dropping to a low of 9.1).

The amount of total CN and free CN behaved differently. Both were observed to be at mid-range at the beginning of the process, but significantly increased in concentration at the pregnant pond (after additional CN was added to the process). The amount of total and free CN gradually decreased to the lowest levels at sites J and K.

Site K had low levels of both CN and metals to allow testing of bead performance in a potentially more challenging environment. Samples from site K was selected in particular as the testing ground to determine whether the surface area, biochemical content/type, heat treatment and pH of the bead would have an effect on the performance of the beads.

B. Column Operation: Bead Optimization

In total, 23 trials were conducted to examine how the various beads reacted at the different sites (Table 9).

TABLE 9

Bead type optimization for selected sites.

| Bead Type | Removal (%) | | | |
|---|---|---|---|---|
| | Au | Ag | Cu | Pb† |
| Site K | | | | |
| WBS | 28% | 70% | 35% | — |
| WB4 | 16% | 27% | 22% | — |
| WB6 | 18% | 21% | 14% | — |
| WB7 | 22% | 23% | 22% | — |
| DB50 | 22% | 11% | 29% | — |
| DB80 | 18% | 37% | 25% | — |
| DB120 | 24% | 19% | 29% | — |
| SB | 22% | 34% | 23% | — |
| CSBS | 28% | 29% | 39% | — |
| CSBL | 14% | 5% | 23% | — |
| EE | 24% | 35% | 8% | 14% |
| Site A | | | | |
| WBS | 36% | 77% | 26% | 95% |
| WB6 | 37% | 47% | 27% | 96% |
| DB50 | 23% | 18% | 16% | 94% |
| DB120 | 45% | 47% | 46% | 75% |
| SB | 36% | 45% | 26% | 96% |
| EE | 17% | 30% | 3% | 97% |
| Site F | | | | |
| WBS | 31% | 39% | 19% | 85% |
| WB6 | 19% | 9% | 7% | 71% |
| DB50 | 22% | 19% | 19% | 95% |
| DB120 | 16% | 19% | 10% | 56% |
| SB | 25% | 19% | 11% | 69% |
| EE | 31% | 9% | 7% | 86% |

†Some values not reported due to problems with low initial values and assay precision.

When all beads were tested at site K, results showed that bead WBS (3 mm) demonstrated higher Au, Ag and Cu removal percentages when compared to bead WB6 (5 mm), demonstrating that a greater surface area provided higher binding capabilities. This disparity was even greater when small (CSBS) and large (CSBL) concentrated secreted biochemical (i.e. exudates) beads were compared.

When secreted and biomass derived biochemical beads were contrasted, no significant trends were observed. Furthermore, when the secreted biochemicals (exudates) were concentrated in the bead (SB vs. CSBL) metal removal did not increase as predicted.

Another variable analyzed was the heat-treating technique of biomass-derived biochemicals. For this variable, beads WBS (wet), DB50 (50° C.), DB80 (80° C.) and DB120 (120° C.) were compared. Bead WBS showed an overall greater percentage removal of all metals. Bead DB120 did show a higher affinity for Au when compared to bead DB80, which could be due to the heat treatment method that was similar to activated carbon. Ag removal also decreased with further heat treatment of the beads.

Lastly, it was investigated if beads prepared at different pH levels during the encapsulation process had an effect on their metal binding ability. Beads WB4, WB6 and WB7, with respective pH levels of 4, 6 and 7, with a control pH of 6 were compared. The results demonstrate that overall, bead WB7 had the best overall metal removal in comparison to beads WB4 and WB6; with the exception of Ag removal, which was higher with bead WB4.

Additional studies were carried out at sites A and F to further explore the effect of surface area, biochemical type and heat treatment method on the performance of the beads. Site A, which was located directly off the Leach Pad process, had the highest concentration of metals and one of the lowest levels of CN. While without wishing to be limited by theory, these conditions are favourable to achieve the optimal performance for the beads. Conversely, site F, possessed both lower metal concentrations and higher levels of CN. These conditions were expected to unfavourably affect the performance of the beads.

When the surface area of the beads was compared at sites A and F, the same positive effect of smaller sized beads demonstrated at site K was observed. When comparing secreted and biomass derived biochemical beads at sites A, K and F, the beads had similar performances for each metal except Ag; which was consistently removed at a higher percentage by biomass bead WBS.

When comparing heat treatment techniques at different sites the trends were very different based on bead type and site. At site A, bead DB120 had the highest removal of Au and Cu; while at site K there were no significant differences. The Au loading of bead DB120 at site A exhibited a significant increase compared to all other beads at any other site. This increase in loading could be due to either the higher Au concentration or the lower CN levels. At site F, the WBS bead had the best removal of Au. This could demonstrate the importance of the binding preference of the bead type and water chemistry of the site. At all sites, the WBS bead had the highest Ag removal.

This series of trials demonstrated the significance that bead type and preparation method had on performance and selectivity. Bead DB120 was selected as the candidate for Au binding when used at the beginning of the process (site A). There was also a high removal of Cu and Pb with this bead so pretreatment to remove these metals would be required to achieve selectivity. Bead DB50 was selected as the candidate for Cu removal and bead SB as the candidate for Pb removal because of relatively low removal ratios of Au compared to target metals. These promising results were used for optimizing the setup of the remaining trials.

C. Column Operation: Site Optimization

Site optimization was carried out using bead WBS (Table 10). This bead was selected for further testing at each sites within the process to look for trends in performance or selectivity based on site. Bead WBS had the best general performance when tested at sites A, F and K in the bead optimization studies and was the first optimized bead that was extensively tested in the lab during initial trials. The lab work focused on optimizing total percentage removal for all metals so this is potentially why it generally performed better than other beads with respect to metal removal. WBS was next tested on how it would perform at different sites.

TABLE 10

Performance optimization for all sites for bead WBS.

| Site | Removal (%) | | | |
|---|---|---|---|---|
| | Au | Ag | Cu | Pb† |
| A | 36% | 77% | 26% | 95% |
| B | 46% | 66% | 29% | 93% |
| C | 28% | — | 20% | — |
| D | 42% | 40% | 21% | 89% |

TABLE 10-continued

Performance optimization for all sites for bead WBS.

| | Removal (%) | | | |
|---|---|---|---|---|
| Site | Au | Ag | Cu | Pb† |
| E | 53% | 44% | 22% | 34% |
| F | 31% | 39% | 19% | 85% |
| G | 33% | 38% | 16% | — |
| H | 41% | 48% | 19% | 25% |
| I | 22% | 54% | 18% | 3% |
| J | 52% | 84% | 35% | — |
| K | 28% | 70% | 35% | — |

†Some values not reported due to problems with low initial values and assay precision.

The highest removal of Au was at site E (53%), site J for Ag (84%), sites J and K for Cu (35%) and site A for Pb (95%). It was observed that there was higher removal percentages for Cu and Ag for samples with the lowest level of free CN (sites J and K). Additionally, it was observed that sites with high total CN levels exhibited poor Cu and Ag removal (site G).

Overall, there were significant bead performance differences based on site location. These differences could be linked to water chemistry or metal concentration, or a combination of other factors. The results of site optimization demonstrate the importance of not only optimizing bead type, but also the specific sites within the process. In order to limit the factors affecting bead performance, an attempt to isolate the effect of CN and pH was made with water chemistry optimization trials.

D. Optimizing Water Chemistry

In both the bead and site optimization trials, general trends linked to lower performance when higher CN levels are present and conversely, higher performance in lower pH conditions. This series of trials had the goal of isolating the effect of these parameters on bead performance.

To isolate the effect of CN and pH on the performance of the beads, CN was destroyed and the pH was adjusted in samples from sites A and K. Hydrogen peroxide ($H_2O_2$) was used to reduce CN levels for sites A and K to almost 0 ppm from 334 and 133 ppm (total) and 0 and 90 ppm (free), respectively. The pH was also adjusted from 11.9 and 9.1 to 4 for sites A and K. The performance of the beads was then compared for untreated water. CN reduced water and pH lowered, CN reduced water.

TABLE 11

Comparison of unencapsulated *Euglena* to activated carbon on their own and in series.

| | Loading of Metal (g/t) | | | |
|---|---|---|---|---|
| Material Used | Au | Ag | Cu | Pb |
| Site A | | | | |
| Carbon | 0.22 | 1.8 | 800 | 48 |
| EE* | 1.08 | 0.96 | 60 | 90.3 |
| EE + Carbon | 3.1 | 1.4 | 750 | 11 |
| Site K | | | | |
| Carbon | 0.02 | 1.4 | 850 | 0.17 |
| EE* | 0.36 | 1.02 | 120 | 0.02 |
| EE + Carbon | 0.64 | 0.98 | 840 | 0.33 |

*Calculated metal loading based on percent removal.

At both sites, there were a significant positive correlation to destroying the CN and bead performance (FIG. 9). At site A, combining CN destruction and pH adjustment significantly improved Ag and Cu removal. Au removal improved slightly when combining CN destruction and pH adjustment. At site K, CN destruction alone had the best effect on Au, Cu and Pb removal; while Ag removal benefited from both CN destruction with and without pH adjustment. Overall, the reduction of CN (either with or without pH adjustment) improved removal of all metals. This is another example of how significantly the CN speciation at each site can affect performance.

The process water being treated is a CN containing solution; the metal ions of interest are most likely in a metal CN anionic complex. While not wishing to be limited by theory, it is thought that the bead mechanism of action involves the interaction of metal cations with the bead's material. Having the metal in an anionic complex state could potentially impede the performance of the bead material. These trials were able to demonstrate that destroying CN had a positive effect on the performance of the beads. Most gold mines around the world are required by law to destroy CN and metal CN complexes in their tailings prior to discharge so there is a possibility of locating the beads after this treatment. The more cost effective method would be to select sites within the process with the lowest CN level for optimal performance.

E. Carbon Column Pretreatment

A part of the mining operation involves carbon columns which are present in the process to selectively adsorb Au/Ag from process solutions. Since carbon also has a high affinity for other metals such as Cu, testing how a pretreatment step can increase the selectivity and loading of the carbon column was crucial. For these experiments, columns were filled with activated carbon and loading capabilities were compared with pretreated and non-pretreated process solutions.

Figure 10:
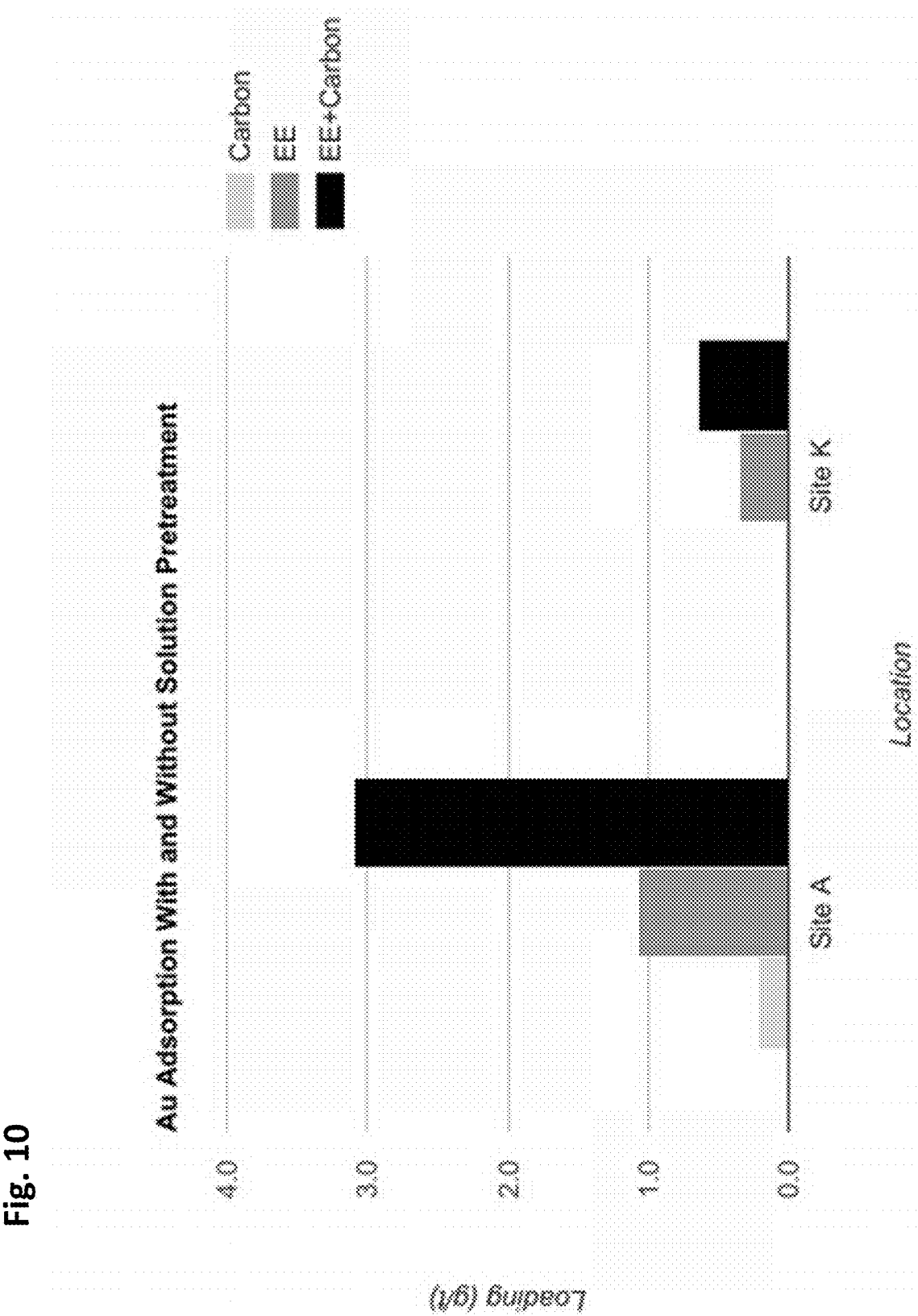
FIG. 10 shows improved adsorption of Au after pretreatment.

This technique used unencapsulated *Euglena* (EE) as a pretreatment prior to the carbon column. Promising results were found with this approach and were demonstrated at sites A and K (Table 11). The loading of Au increased dramatically, at site A the loading increased by 15 times and at site K it increased over 30 times (FIG. 10). At sites A and K there was a negligible difference in Cu loading showing a higher selectivity for Au. At both sites the loading of Ag also decreased, as did Pb loading at site A. Overall, pretreatment with EE increased the Au selectivity of carbon while loading of the other metals either decreased or remained unchanged (with the exception of Pb at site K).

F. Column Series: Carbon Optimization

Preliminary results indicate that some beads have a higher affinity for certain metals, supporting that rather than only processing samples through a column containing one bead, it would be beneficial to pass solution through columns in series to selectively remove target metals. The goal of this study was to explore the use of these beads upstream of a carbon filter to remove metals that were decreasing Au selectivity and enhance carbon columns.

Beads DB50 and SB were selected for these trials based on the results of the bead optimization work. Bead DB50 was selected based on its lower affinity for Au compared to bead WBS and its relatively similar removal of Cu, this bead would have a target of removing Cu in the series. Bead SB was selected because it had the highest preference for Pb removal, therefore this bead would have the target of removing Pb in the series. For both sites A and K, two combinations of beads were used, beads DB50 then SB followed by carbon (Column Series 1), or bead SB followed by carbon (Column Series 2) (Table 12).

TABLE 12

Comparison of Column Series 1 and 2 at site A.

Site A

|  | Bead | Au g/t | Au % dist. | Ag g/t | Ag % dist. | Cu g/t | Cu % dist. | Pb g/t | Pb % dist. |
|---|---|---|---|---|---|---|---|---|---|
|  | Carbon | 0.22 | — | 1.8 | — | 800 | — | 48 | — |
| Column | DB50 | 16 | 90 | 3.9 | 59 | 7300 | 84 | 980 | 99.24 |
| Series 1 | SB | 1.7 | 9 | 2.4 | 36 | 830 | 10 | 5.9 | 0.59 |
|  | Carbon | 0.15 | 1 | 0.36 | 5 | 600 | 7 | 1.6 | 0.16 |
| Column | SB | 1.7 | 38 | 3.8 | 80 | 1200 | 63 | 110 | 92 |
| Series 2 | Carbon | 2.8 | 62 | 0.94 | 20 | 700 | 37 | 10 | 8 |

At site A, the Column Series 1 pre-carbon beads had very significant removals of their target metals: Cu and Pb, and resulted in lower amounts of Cu and Pb on the carbon column when in series than alone. Though not specifically chosen for, this was also the case with Ag binding, increased removal by the beads resulted in lower amounts on the carbon. However, it also demonstrated a higher than anticipated removal of Au. While without wishing to be limited by theory, because these tests used a set volume of process solution, the capacity of the beads was not met. This could mean that there is an initial higher affinity for Au in bead DB50 than for carbon. One of skill in the art can readily recognize that, once saturated, most of the Au would end up on the carbon column.

Column Series 2 at site A had very promising results. The first column with bead SB significantly removed Ag, Cu and Pb and decreased the level of these metals on the carbon. This resulted in higher Au loading on the carbon compared to carbon on its own (over 10 times). When comparing the two Series, bead SB produced very similar Au loading results. This potentially demonstrates that bead SB has a relatively low threshold for Au loading. A low Au threshold coupled with its demonstrated ability to remove Cu and Pb supports that bead SB may be suitable as a means for pre-carbon treatment of process solution.

Site K Column Series 1 had a similar overall effect as it did at site A (Table 13). There was significant removal of all metals by the first column which resulted in decreased binding of Ag and Cu and low amounts of Pb on the carbon. A majority of the Au and Ag was removed by the first column but it still resulted in an increase in total Au loading on the carbon (over 10 times).

TABLE 13

Comparison of Column Series 1 and 2 at site K.

Site K

|  | Bead | Au g/t | Au % dist. | Ag g/t | Ag % dist. | Cu g/t | Cu % dist. | Pb g/t | Pb % dist. |
|---|---|---|---|---|---|---|---|---|---|
|  | Carbon | 0.02 | — | 1.4 | — | 850 | — | 0.17 | — |
| Column | DB50 | 5.5 | 91 | 10 | 77 | 7600 | 88 | 44 | 92 |
| Series 1 | SB | 0.28 | 5 | 2.5 | 19 | 660 | 8 | 3.5 | 7 |
|  | Carbon | 0.26 | 4 | 0.50 | 4 | 350 | 4 | 0.49 | 1 |
| Column | SB | 0.74 | 50 | 6.7 | 90 | 1400 | 62 | 5.8 | 78 |
| Series 2 | Carbon | 0.74 | 50 | 0.76 | 10 | 856 | 38 | 1.6 | 22 |

For Column Series 2 there was a significant level of Ag, Cu and Pb removed by the first column but it did not lead to decreased loading of these metals on the carbon. Though Ag levels did decrease, similar Cu and higher Pb amounts were observed on the carbon. However, there was still a significant increase in Au loading on the carbon (over 30 times) compared to carbon alone.

Although improved carbon Au loading was observed in Column Series 2 at both sites, a discrepancy between the total amount of loaded Au was established between Column Series 1 and 2. This emphasizes the need to perform further tests that do not limit the amount of process solution through the columns. This would lead to conditions closer in line to those on site, and in turn, a better understanding of how these series of columns will perform. Overall though, using beads in series with carbon can significantly increase the carbon loading of Au and decrease the loading of Cu and Pb. One of skill in the art could readily modify the upstream bead columns to decrease the Au removal, to increase the amount of Au available to be bound by the carbon.

G. Column Series: Bead Optimization

As noted above, it was observed that bead DB120 was able to remove significant amounts of Au from sites A and K. Similar to carbon, DB120 also binds Cu in high amounts. Therefore, a bead was added prior to solutions passing through the columns to remove Cu and potentially increase Au selectivity. Based on the prior column results, it was decided to again test beads DB50 and SB, this time with DB120. For both sites A and K, Column Series 3 (bead DB50 then SB upstream of bead DB120) and Column Series 4 (bead SB upstream of bead DB120) were tested to potentially replace carbon (Table 14 and Table 15).

TABLE 14

Comparison of Column Series 3 and 4 at site A.

Site A

| | | Au | | Ag | | Cu | | Pb | |
|---|---|---|---|---|---|---|---|---|---|
| | Bead | g/t | % dist. | g/t | % dist. | g/t | % dist. | g/t | % dist. |
| | DB120* | 8.34 | — | 4.44 | — | 3090 | — | 211 | — |
| Column | DB50 | 15 | 79 | 4.8 | 53 | 7700 | 80 | 1100 | 98.9 |
| Series 3 | SB | 2.4 | 13 | 2.7 | 30 | 920 | 9.6 | 2.5 | 0.2 |
| | DB120 | 1.7 | 9 | 1.6 | 18 | 1000 | 10.4 | 9.1 | 0.8 |
| Column | SB | 2.3 | 39 | 3.3 | 57 | 870 | 37 | 77 | 68 |
| Series 4 | DB120 | 3.6 | 61 | 2.5 | 43 | 1500 | 63 | 37 | 32 |

*Calculated metal loading based on percent removal.

TABLE 15

Comparison of Column Series 3 and 4 at site K.

Site K

| | | Au | | Ag | | Cu | | Pb | |
|---|---|---|---|---|---|---|---|---|---|
| | Bead | g/t | % dist. | g/t | % dist. | g/t | % dist. | g/t | % dist. |
| | DB120* | 0.72 | — | 1.14 | — | 828 | — | n/a | — |
| Column | DB50 | 3.5 | 80 | 9.4 | 70 | 6200 | 79 | 19 | 60 |
| Series 3 | SB | 0.56 | 13 | 2.9 | 21 | 660 | 8 | 1.9 | 6 |
| | DB120 | 0.34 | 8 | 1.2 | 9 | 950 | 12 | 11 | 34 |
| Column | SB | 0.82 | 56 | 4.2 | 72 | 1000 | 50 | 5.6 | 32 |
| Series 4 | DB120 | 0.65 | 44 | 1.6 | 28 | 990 | 50 | 12 | 68 |

*Calculated metal loading based on percent removal.

When observing site A, Column Series 3 had a similar overall effect as Column Series 1. There was significant removal of Cu and Pb by the first and second columns, which decreased both metals dramatically on bead DB120. The upstream beads were responsible for significant Au loading which resulted in relatively low Au loading on bead DB120. However, compared to carbon at this site with the same beads upstream, there was over 10 times more Au captured on bead DB120 (FIG. 11). Similar trends were observed when comparing Column Series 4 and Column Series 2 at the same site. Again, bead DB120 captured more Au than carbon in the same series. Upstream, bead SB bound a high amount of Ag, Cu and Pb which decreased the amount of these metals on bead DB120, compared to DB120 alone. Although a decrease is identified, DB120 still bound these metals in a relatively high amount. One of skill in the art can readily improve the selectivity of these beads.

Results of Column Series 3 at site K were similar in trend to those observed at site A. Beads DB50 and SB removed large amounts of all metals, however, at this site it did not result in lowered amounts of metals on bead DB120. In the end though, higher Au loading was observed on bead DB120 than carbon alone and slightly higher than carbon in the same series. For Column Series 4, there was an increase in Au loading on bead DB120 compared to Column Series, but not to carbon in the same series. Throughout the series, bead DB50 consistently showed significant binding of Cu (~7 g/kg). The inventors predict that increase solution volumes will increase capacity for Cu binding by bead DB50.

These results show that bead DB120 could potentially be used as a replacement for a carbon-based process for capturing Au. Although these Column Series established that bead DB120 exhibited higher binding of non-target metals than carbon in the same series, it still possessed a higher Au loading ability. Furthermore, extremely large differences were observed when comparing the loading capabilities of carbon and bead DB120 not in series (0.22 vs. 8.34, 0.02 vs. 0.72, g/t at sites A and K, respectively). This higher Au loading compared to carbon was also observed with bead DB50 when it was used as the first column in Column Series 1 and 3. Bead DB50 did not show a specific selectivity to Au as it also continuously loaded more Cu and Pb than carbon. One of skill in the art could readily modify the column series to increase Au capacity and selectivity.

IV. Conclusions

Results obtained from testing at the mining operation were able to meet and exceed anticipated results based on prior laboratory testing. The presently disclosed innovative bead technology demonstrated a significant ability to reduce non-target metal concentrations in process solutions. This combined with the capability of the beads to also capture Au, has the potential for various possibilities. Numerous tests were performed to determine the performance, selectivity and loading of the beads.

Metal and CN concentrations were evaluated at various sites throughout the complex. As expected, metal concentrations varied throughout the process and a wide range of CN concentrations and pH levels were observed. From these results, it was determined that site K provided a good environment to test all beads to determine performance differences.

When testing all variation of beads, it was observed that smaller beads (3 mm) had higher removal percentages than larger beads (5 mm); supporting that increased surface area produced better results. Differences were detected when comparing heat treatment techniques for bead preparation as well as comparing beads prepared at varying pH levels.

Based on these results, select beads were further tested at two additional sites. Sites A and F possessed differing concentrations of metals and CN to each other and site K, and offered three sites with varying conditions to further determine the differences in performance of the beads. Similar trends in results were observed. Higher amounts of Au removal occurred at site A. The increase was attributed to higher concentrations of Au and lower concentrations of CN, allowing for increased removal. Through these tests, it was determined that bead WBS exhibited the best overall performance and was tested at all sites to determine if there were trends in performance or selectivity based on site location.

When comparing all sites, bead WBS demonstrated a wide range of removal for all metals. Predominantly, a higher removal of metal occurred when CN concentrations were low and conversely, a lower removal when concentrations were high. While without wishing to be bound by theory, through testing of bead WBS at all sites, water chemistry and CN concentration had just as significant an impact on performance as bead type. Therefore, attempts were made to control the impact on CN concentration and pH levels had on bead performance.

At sites A and K, it was demonstrated that by destroying the CN in solution removal percentages were improved, especially with Ag and Cu. All metals saw increased removal at both sites with CN destruction (with and/or without pH adjustment). These water optimization tests show that placement of beads is the most effective if located at sites where low CN levels are present.

As an alternative to beads, unencapsulated *Euglena* was tested as a solution pretreatment technique to attempt to enhance the Au and Ag loading capabilities of carbon. Contact of the solution with *Euglena* prior to carbon demonstrated increased Au loading on the carbon. This was similarly attempted with beads to try and eliminate non-target metals prior to carbon contact and ultimately improve Au adsorption, In Column Series 1, beads DB50 and SB were used in series at sites A and K prior to carbon contact and removed significant amounts of Cu and Pb. This resulted in lowered amounts on the carbon. At site K carbon loading increased (0.02 vs. 0.26, g/t). Similar results were shown for Column Series 2, when bead SB was used by itself prior to carbon contact. Au loading on the carbon improved significantly at both sites A (0.22 vs. 2.8, g/t) and K (0.02 vs. 0.74, g/t) over carbon alone. Bead DB50 demonstrated a higher than desired affinity for Au, affecting the amount available to be bound by carbon. However, it did consistently bind significant amounts of Cu (~7 g/kg), which approaches industry standards. One of skill in the art can readily decrease the affinity for Au while increase the affinity for non-target metals of upstream beads, which is predicted to significantly improve carbon binding abilities.

Example 2C: Batch Tests with Artificial Solutions

Batch tests were performed with artificial metal solutions to assess metal removal capabilities of beads WBS and SB. 1.5% sodium alginate and 1.5% calcium chloride solutions were used for encapsulation. For WBS beads, a ~4:1 mixture of 1.5% sodium alginate solution:wet biomass mixture was used. In addition, for SB beads, a 1:1 mixture of 1.5% sodium alginate solution:spent media solution was used. Single metal and multi-metal solutions were tested. Results for single metal solutions are the average of three tests and for multi-metal solutions, four tests. Tests were run in flasks for 24 hours while being agitated on shaker tables. Solutions and solids were assayed by ICP-MS. Artificial metal solutions were prepared as follows (Table 16A):

TABLE 16A

Artificial metal solutions

| Testing For | Solution Conc. (mg/L) | pH | Reagent Used |
|---|---|---|---|
| Cooper (Cu) | ~750 | 4.5 | $CuSO_4 \cdot 5H_2O$ |
| Lead (Pb) | ~250 | 5.5 | $Pb(CH_3CO_2)_2 \cdot 3H_2O$ |
| Gold (Au) | ~5 | 2.6 | Au stock (in 0.5 M HCl) |
| Silver (Ag) | ~11 | 5.9 | $AgNO_3$ |
| All | Cu:573, Pb:8.91, Au:0.428, Ag0.984 | 4.8 | As above, except $AuCl_3$ |

In general, WBS and SB beads were, responsible for a similar percent removal except when it came to single metal solutions of copper and gold, where WBS beads removed a slightly higher percentage (Table 16B and C). However, SB beads consistently loaded a larger amount of metal on a per dry bead mass basis.

TABLE 16B

Results from single metal solutions.

| Bead Type | Removal (%) | Loading (g/t) |
|---|---|---|
| Copper Removal | | |
| WBS | 23.1 | 41133 |
| SB | 13.6 | 110000 |
| Lead Removal | | |
| WBS | 91.5 | 48100 |
| SB | 92.6 | 596667 |
| Gold Removal | | |
| WBS | 99.1 | 1009 |
| SB | 71.3 | 3329 |
| Silver Removal | | |
| WBS | 47.7 | 210 |
| SB | 45.2 | 317 |

TABLE 16C

Results from multi-metal solution (Removal, %)

| Bead Type | Cu | Pb | Au | Ag |
|---|---|---|---|---|
| WBS | 32.1 | 80.8 | 89.7 | 48.3 |
| SB | 31.8 | 83.8 | 87.4 | 49.0 |

Example 2D: Desorption, Reuse and Carbon Pretreatment Desorption

To help assess the capability of encapsulated *Euglena* and/or *Euglena* exudates being used for commercial metal removal applications, metal desorption tests were performed to determine the potential to remove metal bound to the beads; which would then allow the beads to be used to remove more metal. The beads were prepared as in Example 2C. Tests were first performed on beads after contact with artificial multi-metal solutions with four different desorbents of the same molar concentration: 0.2 M hydrochloric acid (HCl), 0.2 M sodium hydroxide (NaOH), 0.2 M nitric acid ($HNO_3$), and 0.2 M sulphuric acid ($H_2SO_4$). These desorbents, at two different concentrations (except for NaOH, only at 0.1 M), were then tested on beads after contact with mine solution. Two other desorbents, potassium cyanide (KCN) and thiourea, were tested for selective removal of gold from beads. Successive rounds of testing, with desorption of metals in between, were then conducted to demonstrate that the ability to remove metals can be just as effective after desorption as using fresh beads. For these reuse tests, $HNO_3$ was used as the desorbent between rounds of mine solution contact.

For desorption of metals after contact with multi-metal solution, the three acids (HCl, $HNO_3$, $H_2SO_4$) were more effective overall than NaOH (Table 16D). However, NaOH was significantly better than the three acids at desorption of Au. All three acids had similar success at desorption of Cu and Pb from both WBS and SB beads, while HCl had an increased ability to desorb Ag from the beads. While for the most part both beads released metals similarly, desorption of Ag from SB beads compared to WBS after contact with any of the acids was considerably increased. NaOH was slightly better at desorbing all metals from bead WBS than bead SB.

TABLE 16D

Desorption - multi-metal solution (desorption, %)

| Desorbent/Bead Type | Cu | Pb | Au | Ag |
|---|---|---|---|---|
| 0.2M HCl/WBE | 77.3 | 100 | 1.7 | 56.3 |
| 0.2M HCl/SB | 78.0 | 96.1 | 13.5 | 100 |
| 0.2M NaOH/WBS | 77.3 | 100 | 1.7 | 56.3 |
| 0.2M HCl/SB | 78.0 | 96.1 | 13.5 | 100 |
| 0.2M NaOH/WBS | 25.0 | 74.3 | 100 | 50.0 |
| 0.2M NaOH/SB | 14.3 | 67.6 | 70.4 | 39.0 |
| 0.2M $HNO_3$/WBS | 77.2 | 93.1 | 9.0 | 11.9 |
| 0.2M $HNO_3$/SB | 73.8 | 73.2 | 9.9 | 39.3 |
| 0.2M $H_2SO_4$/WBS | 74.1 | 97.3 | 12.2 | 11.5 |
| 0.2M $H_2SO$/SB | 79.4 | 90.2 | 9.6 | 46.1 |

For desorption of metal from beads WBS and SB after contact with mine solution, an increase in desorbent concentration from 0.1 M to 0.25 M was able to desorb increased amounts of metals in almost all cases (Table 16E). Similar to the multi-metal solution, NaOH was less effective at desorbing metal compared to the acid desorbents, except when it came to Au. The three acids were more effective at desorbing Cu and Pb than Au and Ag. When comparing the two beads, all desorbents were more successful at desorbing metals from bead SB than WBS. Overall, 0.25 M $HNO_3$ shows to be the preferred desorbent for bead SB and 0.25 M HCl and 0.25 M $HNO_3$ are the preferred desorbent for bead WBS. These results show metal desorbed from encapsulated *Euglena* and *Euglena* exudates after they have removed metals from effluent solutions.

TABLE 16E

Desorption - mine solution (desorption, %)

| Desorbent/Bead Type | Cu | Pb | Au | Ag |
|---|---|---|---|---|
| HCl | | | | |
| 0.1M/WBS | 7.3 | 77.2 | 3.3 | 3.4 |
| 0.25M/WBS | 81.9 | 97.0 | 18.3 | n/a |
| 0.1M/SB | 38.9 | 92.0 | 48.2 | 64.0 |
| 0.25M/SB | 100 | 100 | 46.7 | n/a |
| NaOH | | | | |
| 0.1M/WBS | 20.2 | 8.8 | 23.7 | 2.1 |
| 0.1M/SB | 26.0 | 4.3 | 26.0 | 12.9 |

TABLE 16E-continued

Desorption - mine solution (desorption, %)

| Desorbent/Bead Type | Cu | Pb | Au | Ag |
|---|---|---|---|---|
| HNO$_3$ | | | | |
| 0.1M/WBS | 21.3 | 67.8 | 9.0 | 2.3 |
| 0.25M/WBS | 93.4 | 59.2 | 30.4 | n/a |
| 0.1M/SB | 17.3 | 90.5 | 8.8 | 19.1 |
| 0.25M/SB | 100 | 100 | 99.4 | n/a |
| H$_2$SO$_4$ | | | | |
| 0.1M/WBS | 16.7 | 69.8 | 11.6 | 1.6 |
| 0.25M/WBS | 88.3 | 54.6 | 21.5 | n/a |
| 0.1M/SB | 62.6 | 47.8 | 46.3 | 65.4 |
| 0.25M/SB | 100 | 83.0 | 65.1 | n/a |

Selective Au Desorption

As shown in Table 16F, at contact time of 18 h, increasing the concentration of KCN results in increased desorption of Au from the bead. Other metals were also desorbed, but desorption of Cu and Pb decreased slightly as the concentration of KCN was increased. Ag desorption remained essentially the same as the concentration of KCN changed. Increasing the concentration of thiourea also increased the desorption of Au. A shorter contact time with the same concentration of thiourea was less effective at desorption of Au, while also desorbing more Cu and Ag.

TABLE 16F

Selective Au desorption - mine solution with WBS beads (desorption, %)

| Desorbent | Cu | Pb | Au | Ag |
|---|---|---|---|---|
| 0.0077M KCN | 63.7 | 30.5 | 32.9 | 51.4 |
| 0.1M KCN | n/a | 31.8 | 52.7 | 56.3 |
| 0.2M KCN (1 h) | 42.3 | 18.5 | 66.7 | 43.6 |
| 0.3M KCN (1 h) | n/a | 17.8 | 70.9 | 51.9 |
| 0.1M Thiourea + 0.1 M HCl | 32.3 | 83.2 | 20.9 | 47.7 |
| 0.1M Thiourea (1 h) | 100 | 39.8 | 54.0 | 12.5 |
| 0.2M Thiourea (1 h) | 100 | 2.7 | 71.7 | 28.0 |
| 0.2M Thiourea | 72.7 | 4.4 | 84.8 | 14.4 |

Reuse

The metal removal ability of WBS beads was not affected after desorption of metals (Table 16G). This demonstrates that a desorbent, such as NHO3, can effectively remove bound metals and free up binding locations on the beads for subsequent metal removal without affecting the beads efficacy for at least 3 consecutive contacts with solution.

TABLE 16G

Reuse - mine solution (% removal; average of three tests)

| WBS beads | Cu | Pb | Au | Ag |
|---|---|---|---|---|
| 1$^{st}$ round | 36.6 | n/a | 7.2 | 78.4 |
| 2$^{nd}$ round | 45.0 | 50.0 | 7.8 | 83.2 |
| 3$^{rd}$ round | 34.6 | 66.7 | 2.6 | 81.0 |

Pretreatment Carbon Tests

Tests were performed to determine the benefit of using beads WBS and SB as a solution pretreatment prior to contact with carbon, for example, with train solution that is taken just before mining process water entering carbon trains. Without wishing to be bound by theory, beads would remove the non-target metals (Cu and Pb), decreasing the loading of these metals on the carbon which would result in higher loading of target metals (Ag, and especially Au) on the carbon. Tests were run concurrently with no bead pretreatment and carbon contact alone in order to assess the benefit of bead pretreatment. Bead contact was for 6 hours, while carbon contact was for 16 hours. Results are shown as gram per tonne loading of metals on the carbon by solution type and bead pretreatment (Table 16H).

TABLE 16H

Carbon Tests - Loading (g/t).

| Train Solution | Au | Ag | Cu | Pb |
|---|---|---|---|---|
| Bead WBS pretreatment | 56 | 31 | 8400 | 104 |
| Bead SB pretreatment | 53 | 40 | 8200 | 62 |
| No bead pretreatment | 56 | 43 | 8150 | 420 |
| Pond Solution | | | | |
| Bead WBS pretreatment | 51 | 93 | 9400 | 1 |
| Bead SB pretreatment | 51 | 113 | 9400 | 0 |
| No bead pretreatment | 47 | 129 | 12000 | 3 |

Pretreatment with either bead results in less Pb from train solution (similar to site A solution) being loaded onto carbon, demonstrating that they have the properties to be used in a filter-like capacity to eliminate non-precious metal binding on the carbon without affecting Au loading. This is especially the case with bead SB, which when used as a pretreatment significantly decreases the amount of Pb loaded onto the carbon without significantly affecting the Au and Ag loading. Contacting train solution with WBS or SB beads prior to carbon contact had no effect on carbon loading of Au or Cu. As for pretreatment of pond solution (similar to site K solution) with bead WBS and SB, this resulted in a decrease in binding of Cu and Pb onto carbon while slightly increasing gold loading. This shows that the encapsulated *Euglena* or *Euglena* exudates possess the properties to function as a pretreatment filter to eliminate non-target metals to improve the Au purity on carbon.

Collectively these results demonstrated that the disclosed bead technology are useful. In particular, the methods, uses and biosorbents disclosed herein are useful for remediation or recovery of metals from mining process water such as from carbon trains, resin columns, ponds such as excess, intermediate, pregnant and tailing ponds, leach pads, electrowinning cells, tanks such as flotation, Merrill Crowe, solid phase extraction and pregnant tanks, as well as mining process water leaving or entering carbon trains, resin columns, ponds such as excess, intermediate, pregnant and tailing ponds, leach pads, electrowinning cells, tanks such as flotation, Merrill Crowe, solid phase extraction and pregnant tanks. The ability to capture both target and non-target metals is significant. These beads possess the ability to be an alternative to the current technologies available for metal recoveries and are believed to be more efficient, more flexible and more cost-effective to work complementary to current techniques, such as carbon columns or even replace them. One of the skill in the art can readily modify the disclosed bead technology to increase metal selectivity and loading capacities.

Example 3: Structural and Molecular Characterization of Lyophilized *Euglena* Gracilis Cells I. Introduction As shown in Examples 1 and 2, the algal flagellate *Euglena gracilis* is an efficient biosorbent that warrants further investigation on a structural and molecular level. *E.*

*gracilis* can grow in the presence and absence of light, and also in aerobic and anaerobic conditions. *E. gracilis* can grow in a broad range of pH values 2.5-8, and is naturally found in freshwater, seawater and brackish waters. *E. gracilis* has the potential to be a viable biosorbent for the biosorption of metals, metalloids and REE.

In the present disclosure, molecular structural analysis of freeze-dried (i.e. lyophilized) *E. gracilis* has been conducted by electrospray ionization high-resolution Fourier transform orbitrap mass spectrometry (Q-Exactive ESI Orbitrap). The present study discloses structurally and on a molecular level the presence of key compound classes and functional groups within *E. gracilis*, using a combination of spectroscopic (FTIR) and mass spectrometry techniques (HR-MS) and the growth phase and conditions that are best for the enhancement of compound classes for biosorption potentiality.

II. Experimental Procedures

A. Algal Cultures

*Euglena gracilis* Z, was axenically cultured at 29° C. under a 12 h light (54,000 lx) and 12 h dark cycle, and also cultured in 24 h darkness at 29° C. in a dark chamber (ThermoScientific). *E. gracilis* was grown in *Euglena gracilis* medium (or EGM; Winters et al., 2016) with and without glucose supplementation (20 g·L$^{-1}$) in 1 L Erlenmeyer flasks, with 500 mL of culture medium. *E. gracilis* was collected in the exponential and stationary phases of growth. Cells were centrifuged at 4000 rpm for 6 min and washed thoroughly with Milli-Q water to remove any culture medium from the cells. The lyophilized cells were homogenized using marble mortar and pestle prior to structural and molecular characterization.

B. FTIR Analysis

FTIR spectra of lyophilized *E. gracilis* were obtained by using a ThermoNicolet 380 ATR FTIR spectrophotometer equipped with the EZ Omnic Spectra software (ThermoScientific). The FTIR spectrum was recorded over a range of 4000 cm$^{-1}$ to 400 cm$^{-1}$. Thirty-two scans were acquired at a resolution of 4.000, aperture of 100.00, and mirror velocity of 0.6329.

C. AF4 Analysis

Figure 17:
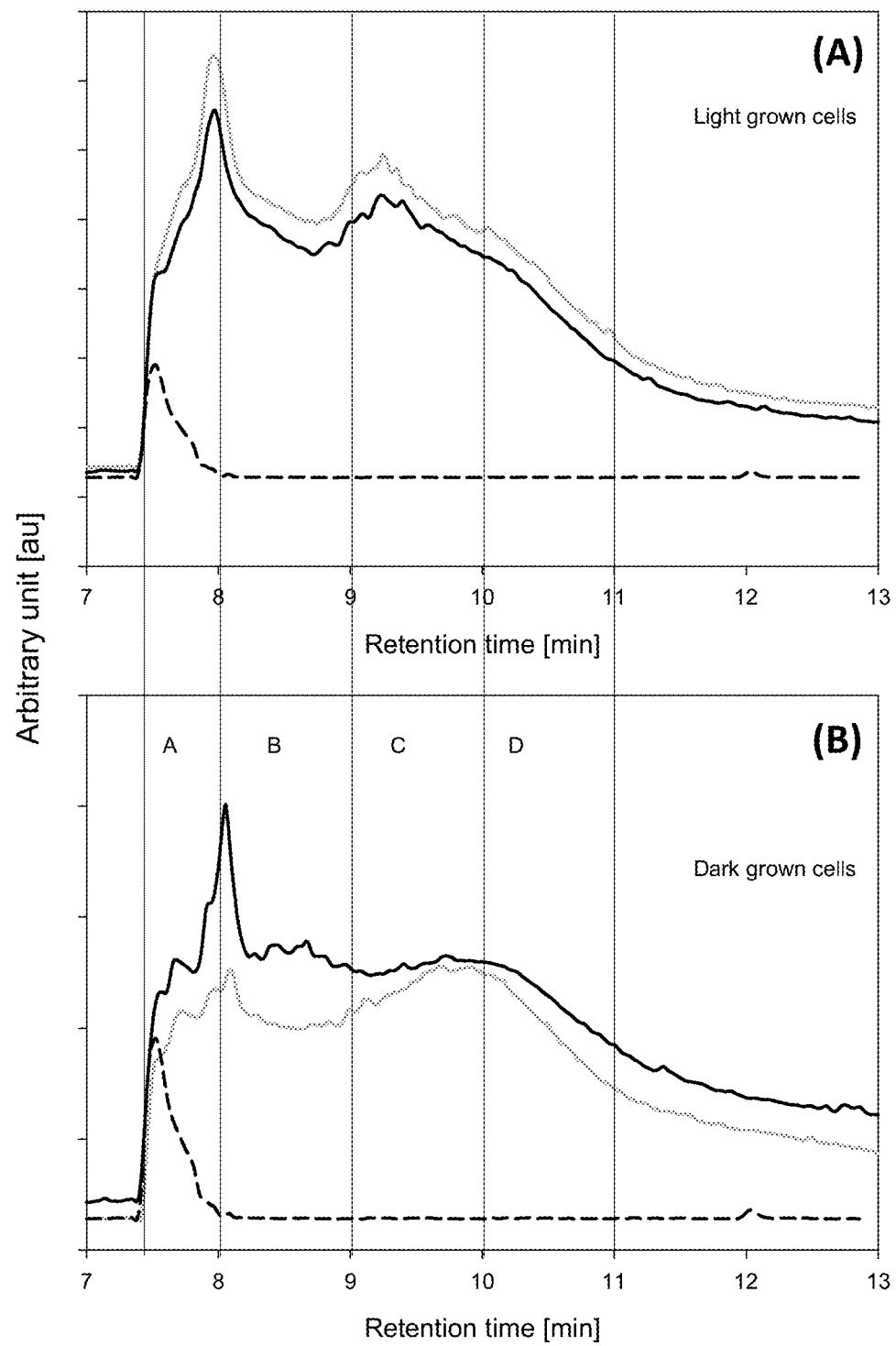
FIG. 17 shows representative fractograms for (A) light and (B) dark grown cells. Replicates 1 and 2 are denoted by the red and blue lines respectively. Blank runs are denoted by the black lines.

The AF4 system was a Postnova Analytics AF2000 Focus (Salt Lake City, Utah, USA) equipped with an online Shimadzu UV-Vis detector (SPD-M30A) operated at 254 nm. A 1 kilodalton (kDa) regenerated cellulose and a 350 μm spacer were used. The eluent (10.1 mM NaCl) was prepared daily. A blank sample of carrier fluid was run before each sample to ensure the absence of memory effects. 200 μl samples were injected via a manual injector valve. Fractions A-D (FIG. 17) were collected at the retention times of 7.5-8, 8-9, 9-10, 10-11 min, respectively, whereas the combined fraction was collected between 7.5-11 min. The unfractionated supernatant was also compared with the combined fraction. The fractions collected, and unfractionated samples were refrigerated at 4° C. and analyzed within 4 days. The replicates of AF4 fractionation were done within 2 days (1 replicate per day).

D. Q-Exactive Orbitrap Analysis

All high-resolution mass spectrometry analyzes were conducted on a Q-Exactive Orbitrap (ThermoFisher) housed at the Trent Water Quality Centre (Peterborough, Ontario, Canada). The lyophilized *E. gracilis* (1 mg·L$^{-1}$) samples were diluted with Milli-Q water and LC-MS grade methanol to give a final concentration of 50:50 methanol:water. The acquisition parameters in positive ion mode were similar to that of Mangal et al. (2016) except that the flowrate was set at 25 μl/min. All samples were spiked with sodium trifluoroacetate (NaTFA) as a calibration standard with a lock mass of 158.96403 in positive ion electrospray mode. The scan range was from 150 to 2000 m/z.

The van Krevelen analysis was completed using an in house Matlab scripts. The different compound classes were defined as lipids ($0.01 \leq O/C \leq 0.1$; $1.5 \leq H/C \leq 2.0$), unsaturated hydrocarbons ($0.01 \leq O/C \leq 0.1$; $0.75 \leq H/C \leq 1.5$), condensed aromatic structures ($0.01 \leq O/C \leq 0.65$; $0.25 \leq H/C \leq 0.75$), protein ($0.1 \leq O/C \leq 0.65$; $1.5 \leq H/C \leq 2.3$; $N \geq 1$), lignin ($0.1 \leq O/C \leq 0.65$; $0.75 \leq H/C \leq 1.5$), tannins ($0.65 \leq O/C \leq 0.85$; $0.75 \leq H/C \leq 1.5$), and carbohydrates ($0.65 \leq O/C \leq 1.0$; $1.5 \leq H/C \leq 2.5$) (Ohno and Ohno, 2013; Mangal et al., 2016). Lignin and protein compound classes were comparable in positive ion electrospray mode rather than negative ion electrospray mode, which is advantageous to this study.

III. Results and Discussion

A. Growth Curves

The growth rates varied in both exponential and stationary phases under different growth and media conditions (Table 17). Light grown cells with the supplementation of glucose surpassed the other media conditions in growth rate, at both exponential and stationary phases of growth. The growth rates seen in light grown cells with glucose supplementation were as expected, as glucose would be metabolized quicker than the other EGM constituents.

TABLE 17

Varying *Euglena gracilis* growth rates in both exponential and stationary phases under different growth and media conditions.

| | Growth conditions | | | |
|---|---|---|---|---|
| Day | Light [μ] | Light (Glucose) [μ] | Dark [μ] | Dark (Glucose) [μ] |
| 0 | | | | |
| 2 | 0.32 | 0.90 | −0.27 | 0.24 |
| 4 | 0.47 | 0.78 | 0.25 | 0.35 |
| 6 | 0.35 | 0.62 | 0.24 | 0.30 |
| 8 | 0.30 | 0.56 | 0.15 | 0.28 |
| 10 | 0.18 | 0.47 | 0.18 | 0.20 |
| 14 | 0.17 | 0.30 | 0.08 | 0.11 |

B. Functional Groups

FTIR spectra of the *Euglena* cells showed five distinct absorption bands with the wavenumbers ranging from ~950 to 1700 cm$^{-1}$ (FIG. 12). These bands were assigned to specific functional groups (carboxylic, phenolic, and amide groups). The carboxylic group (—COOH) was characterized by the C=O stretching at 1710±15 cm$^{-1}$ and with C—O stretching in the 1265±55 cm$^{-1}$ region. Amide 1 (C=O stretching) was found in *Euglena* cells in the ~1650 cm$^{-1}$ region. Amide II and III were found in the 1550 and 1260±40 cm$^{-1}$ regions, respectively. Lignin denoted by the phenolic groups with asymmetrical stretching of the C—O bond was also found at 1230 cm$^{-1}$. Similar peaks were found in both light and dark conditions, with and without glucose supplementation (FIG. 12). While not wishing to be limited by theory, this finding provides that regardless of the growth conditions and phases, similar functional groups were present within the cells grown in dark and light conditions.

C. Structural Analysis

Influence of Photoperiod Duration (Light Vs Dark Grown Cells)

The average abundances of CHO and CHON compounds in exponentially grown light grown cells EGM medium were 9.8 and 28.1% (FIG. 13), respectively, which was comparable to that found in *E. gracilis* dissolved exudates (14 and 21% respectively; Mangal et al., 2016). The abundance of sulfur containing compounds varied significantly between cellular and exudate metabolites. The CHONS species were 48% more abundant in cells than in exudates (Mangal et al., 2016). Higher percentages of the CHO molecular species were seen in dark grown cells (24.4-30.9%) than in light grown cells (9.8-12.2%), regardless of growth phase and media conditions (FIG. 13). The light grown cells were enriched in CHOS and CHON. Together these results showed heteroatom-rich metabolites were preferentially found in light grown cells. It is likely that organelles that are highly specialized to function in light conditions, such as paramylon and chloroplast, would not be active or absent in dark conditions.

The $CHON_{1-2}$ molecular species were more prominent in light grown samples (25.1-28.5%) than dark grown samples (14.0-17.2%) in all media conditions (FIG. 13). The $CHOS_{1-2}$ molecular species were present in all samples with dark grown cells possessing more of these species (11.8-15.5% vs 13.3-18.9% in light and dark grown samples, respectively; FIG. 13). The $CHON_{1-2}S_{1-2}$ molecular species were present in all the samples analyzed (40.3-48.8 vs 37.9-47.7% in light and dark grown samples, respectively; FIG. 13). Light grown cells showed lower H/C and higher double bonded structures (DBE) values than dark grown cells ($p<0.05$; Table 18), showing the presence of more aromatic functional groups in light grown cells. Dark grown cells showed higher O/C and S/C ratios ($p<0.05$), indicating that these cells were more oxygenated and sulfur-rich. No significant difference in aromaticity index (AI) was found between dark grown and light grown cells ($p>0.05$). This marked difference provides, while not wishing to be limited by theory, that light promotes the formation of more $CHON_{1-2}$ molecular species, regardless of media conditions or growth phase.

aromatics. Lower percentages of lignin and aromatics in light grown cells are likely due to the phototransformation of lignin and aromatic compounds (Lu et al., 2016; Medeiros et al., 2015). Higher carbohydrate compound class in dark grown conditions was likely due to more paramylon formation (Matsuda et al., 2011). Lipid compound classes percentages in dark grown and light grown cells of *E. gracilis* (4.8-16.4%, and 12.8-15.3%, respectively) were similar.

Influence of Growth Phase

Figure 14:
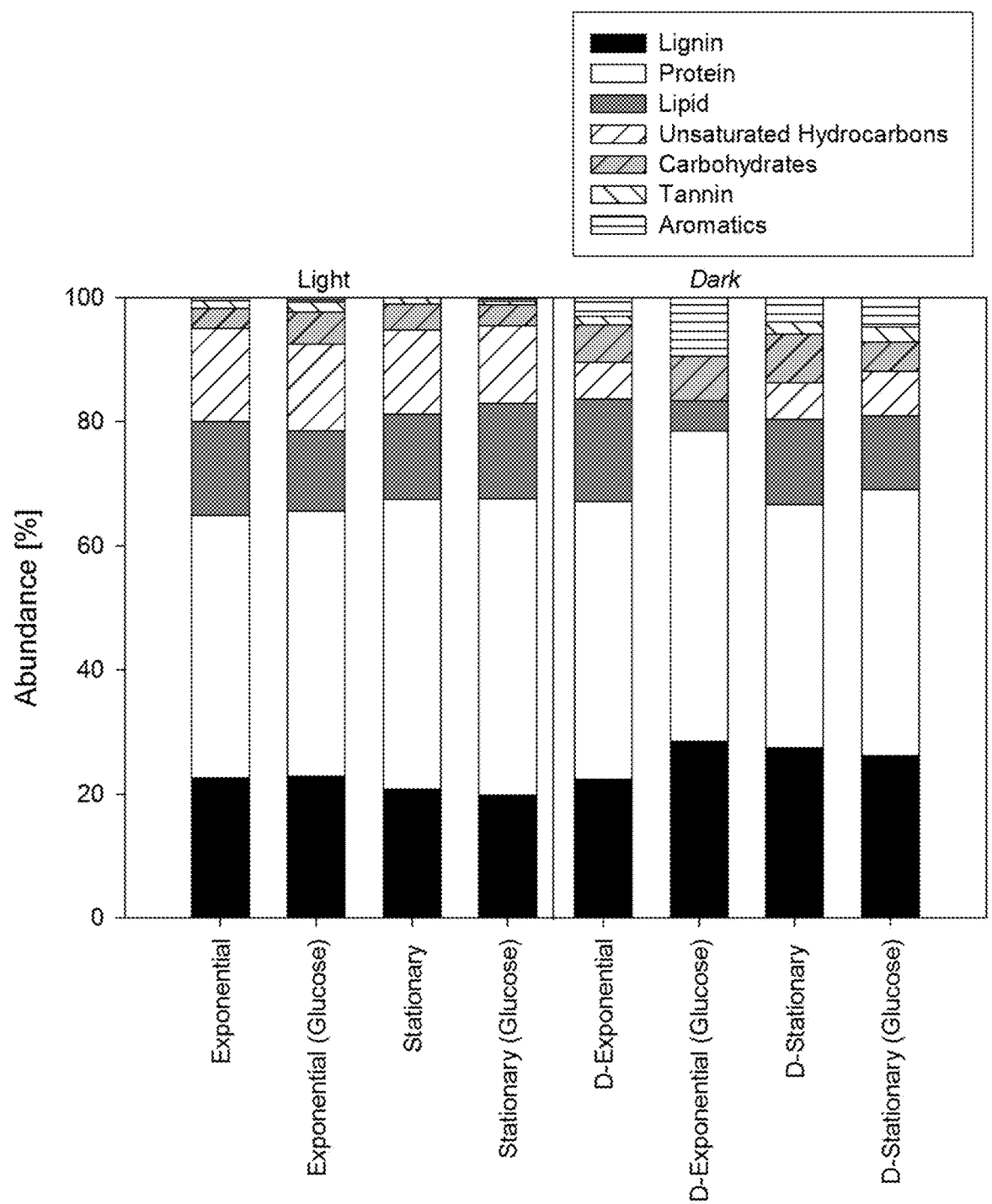
FIG. 14 shows the abundances of compound classes of *E. gracilis* grown in different culture conditions.
Figure 15:
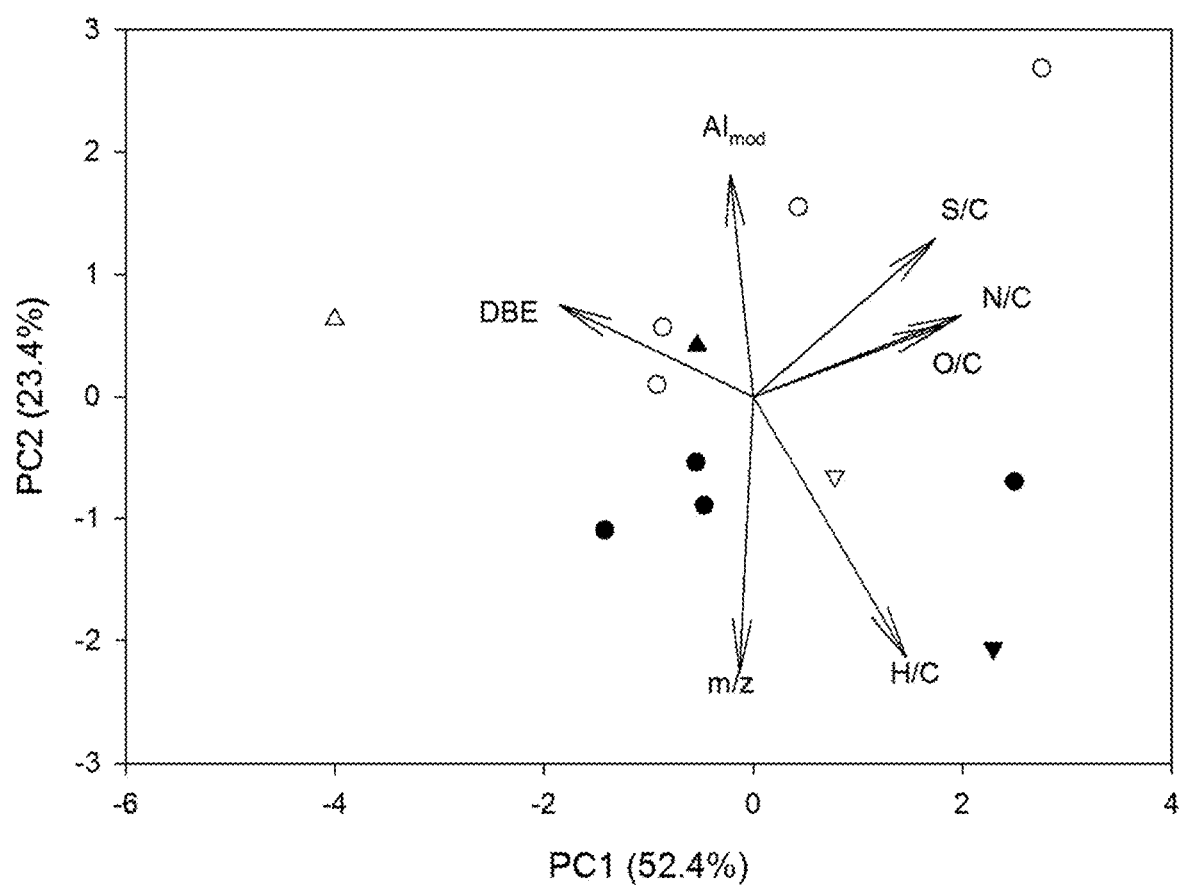
FIG. 15 shows the multivariate variation among cellular composition in terms of elemental ratios. Vectors indicate the direction and strength of each variable to the overall distribution.

The composition of cellular metabolites was growth phase dependent (Table 18; FIG. 14). Principal component analysis (PCA) based on elemental ratios and AI (FIG. 15) showed that exponentially grown dark grown cells in normal media influenced by O/C ratio, indicating that these cells were more oxygenated. Dark grown conditions produced more oxygenated and sulfonated groups (higher O/C and S/C ratios), while light grown conditions favored aromatic and unsaturated structures (FIG. 15). The dark grown cells in exponential phase contained 20% more proteins than the light grown cells. This contrasted with the stationary phase where more proteins were associated with light grown cells than with the dark grown cells (46.6-47.7% vs 39-42.9%, respectively; FIG. 15). Without wishing to be bound by theory, this could be due to the differentiation of proplastids to photosynthetic plastids when exposed to light (Schwartzbach and Shigeoka, 2017). Cell lysis is one explanation for the presence of more proteins and higher % N in the stationary phase (Table 18). Protein percentages was highest in dark grown *Euglena* cells with glucose at the exponential phase (50%), congruent with higher % N in supplemented medium (Table 18). Dark grown cells were less enriched in protein at the stationary phase whereas the reverse was seen for light grown cells. Without wishing to be bound by theory,

TABLE 18

Elemental ratios and abundances, AI and DBE of cells grown in different culture conditions (light vs dark, normal vs supplemented medium).

| Positive Ion Mode | O/C | H/C | N/C | S/C | AI | DBE | Error (ppm) | % C | % H | % O | % N | % S |
|---|---|---|---|---|---|---|---|---|---|---|---|---|
| Light Conditions | | | | | | | | | | | | |
| Exponential (Normal Media) | 0.206 | 1.417 | 0.045 | 0.023 | 0.183 | 12.854 | 0.358 | 59.662 | 7.465 | 2.339 | 25.100 | 5.457 |
| Exponential (Supplemented Media) | 0.212 | 1.375 | 0.045 | 0.024 | 0.191 | 11.516 | 0.343 | 58.469 | 6.891 | 1.831 | 27.675 | 4.959 |
| Stationary (Normal Media) | 0.225 | 1.401 | 0.048 | 0.032 | 0.077 | 10.948 | 0.139 | 60.053 | 7.295 | 2.181 | 25.792 | 4.700 |
| Stationary (Supplemented Media) | 0.199 | 1.394 | 0.045 | 0.027 | 0.126 | 11.201 | 0.296 | 61.376 | 7.136 | 1.856 | 24.772 | 4.883 |
| Dark Conditions | | | | | | | | | | | | |
| Exponential (Normal Media) | 0.269 | 1.544 | 0.038 | 0.066 | 0.071 | 6.900 | 1.009 | 64.645 | 8.390 | 3.591 | 18.413 | 4.974 |
| Exponential (Supplemented Media) | 0.246 | 1.490 | 0.037 | 0.068 | 0.131 | 7.518 | 0.947 | 63.687 | 8.251 | 3.274 | 20.101 | 4.707 |
| Stationary (Normal Media) | 0.248 | 1.489 | 0.037 | 0.069 | 0.131 | 7.607 | 1.030 | 64.671 | 8.648 | 3.178 | 18.815 | 4.707 |
| Stationary (Supplemented Media) | 0.245 | 1.480 | 0.036 | 0.067 | 0.139 | 7.751 | 1.011 | 64.975 | 8.714 | 3.274 | 18.399 | 4.657 |

A marked difference in compound class abundances within dark grown and light grown samples was found (FIG. 14). Protein and lignin compound classes were predominant in *E. gracilis* cells. The protein compound class accounted for 39 to 50% of the total assigned peaks in *E. gracilis* cells. Lignin was more abundant in dark grown cells than in light grown cells. Without wishing to be bound by theory, the 1.43-fold difference in lignin abundance was likely due to the photobleaching of lignin structures in the light grown cultures (Opsahl and Benner, 1998; Helms et al., 2008; Herres et al., 2009; Spencer et al., 2009). Dark grown cells had a higher overall percentage of lignin, carbohydrates, and Fogg (1957) stated that in the exponential phase, light grown algae had a high photosynthetic rate and the products of photosynthesis were used mainly for the protein synthesis. By the end of the exponential phase, the photosynthetic rate would significantly be reduced, and photosynthetic products would become increasingly diverted along pathways other than that of protein synthesis to form "reserves" of lipid or carbohydrate (Fogg 1957). This process was congruent with the reduction in protein abundances in the stationary phase compared to the exponential phase for light grown cells. Differentiation of proplastids into functional photosynthetic apparatus may have a role to play in this as well.

When comparing percentage abundances of compound classes of *Euglena* exudates, the cells showed similar abundance of carbohydrate, protein and lignin but much higher abundances of lipids, condensed aromatic structures and unsaturated hydrocarbons. Without wishing to be bound by theory, higher abundances of carbohydrates, protein and lignin molecules in cells were likely due to their role in cellular processes and/or as nutrient sources (i.e. lipid as storage, or for membrane function; proteins for structural integrity and involved in enzymatic reactions; carbohydrates for paramylon storage in *E. gracilis*) (Matsuda et al., 2011; antek et al., 2012).

Figure 16:
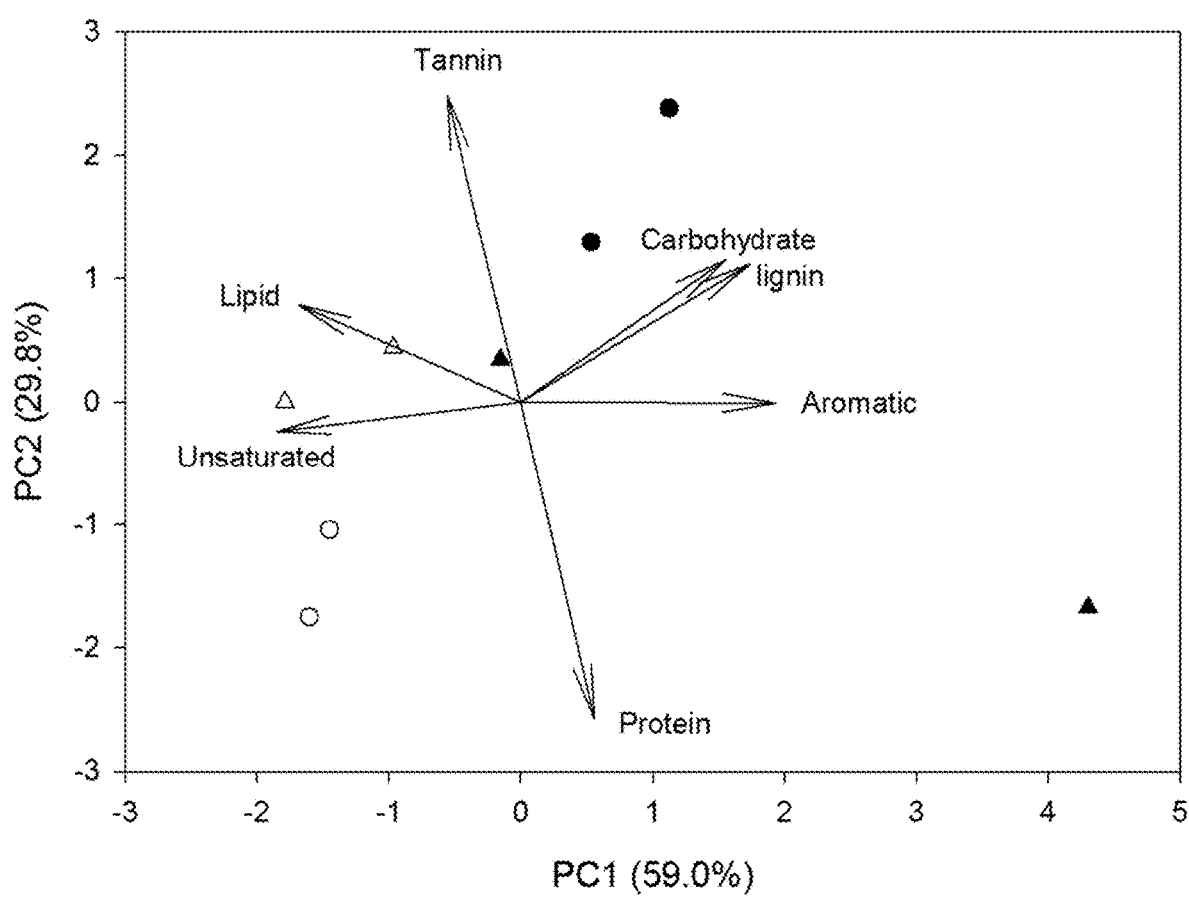
FIG. 16 shows the multivariate variation among cellular composition in terms of compound class abundances associated with *E. gracilis* grown in light (open) and dark (black) conditions at (●) exponential and (■) stationary phases. Vectors indicate the direction and strength of each variable to the overall distribution.

Principal component analysis revealed significant differences in compound class composition of cells grown in different conditions (FIG. 16). First and second principal components (PC1 and PC2) represented 59 and 30% of the total variance explained. Positive PC1 indicated saturated compounds (lignin, aromatics) whereas negative PC2 showed proteinaceous material. The light grown and dark grown samples were clustered separately with the dark and light grown samples displaying positive and negative PC1 values, respectively. The light grown cells were more aromatic in character, congruent with lower H/C and lower % H ($p<0.05$; Table 18). The increase in PC2 from the exponential to stationary phase in the dark grown cells indicated a decrease in protein material and an increase in lipid compounds. This contrasts with the light grown cells where an enrichment in proteinaceous material was found in stationary phase relative to the exponential phase. Physiological modes could affect differences seen. This drastic change is likely due to the difference in energy storage. The autotrophic organisms can store energy as lipid whereas the dark grown organisms favored protein storage (Schwartzbach and Shigeoka, 2017). Together these results highlighted that growth conditions influenced structural composition of cellular organic compounds.

D. Comparison of Unique Compound Classes and Molecular Species with Light and Dark Grown Cells conditions. Dark grown samples showed higher percentages of unique peaks of carbohydrate than light grown samples when the exponential and stationary phases in glucose-supplemented media were compared. Unique condensed aromatic compounds still were more prominent in dark than light grown cultures in all media conditions. Tannins were prominent in dark grown samples than light grown samples, but only when these conditions were compared: exponential phase versus exponential phase with glucose, and stationary phase versus stationary phase with glucose.

E. AF4 Separations of Cellular Fractions

The AF4 fractograms were relatively consistent between replicate cultures (FIG. 17), suggesting comparable size distribution within growth condition. Significant differences in the AF4 fractograms were found between light and dark grown cells, indicating differences in metabolomics processes. The light grown cells have a more sophisticated machinery due to differentiation (Schwartzbach and Shigeoka, 2017). Light grown cellular fractograms (FIG. 17; top graph) showed a characteristic peak at 7.8 min (fraction A) followed by a broad peak at 9.3 min (fraction C). On the other hand, the dark grown cellular fractograms (FIG. 17; bottom graph) showed a sharp peak at 8.3 min (fraction B) and a very broad peak at 9.5-10.5 min (fraction C). The higher retention times suggested higher molecular weight in metabolites isolated from dark cells, congruent with higher weighted average m/z in dark cells.

Figure 18:
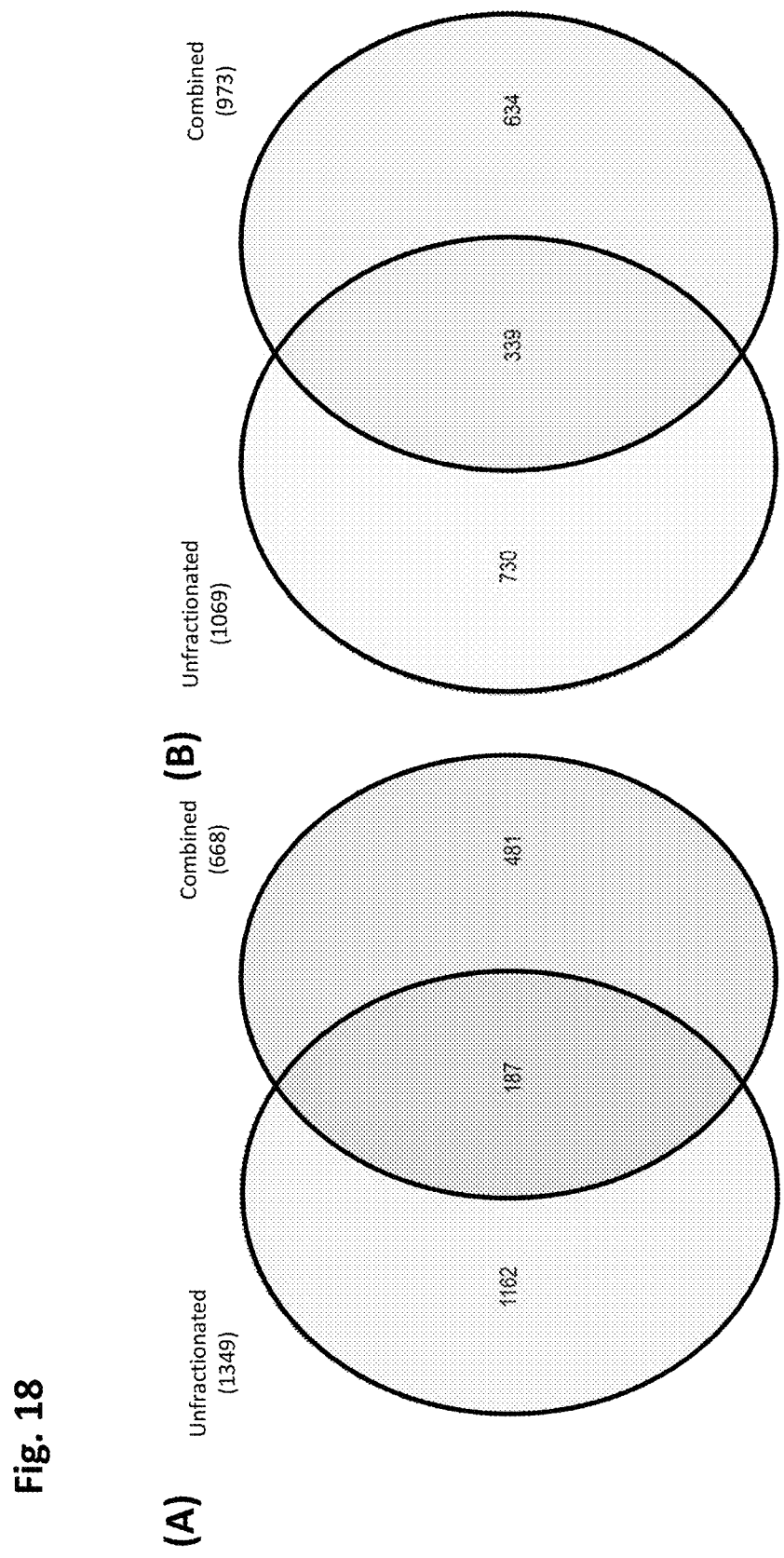
FIG. 18 shows the Venn diagrams of combined fractions and unfractionated supernatant grown in (A) light and (B) dark.
Figure 19:
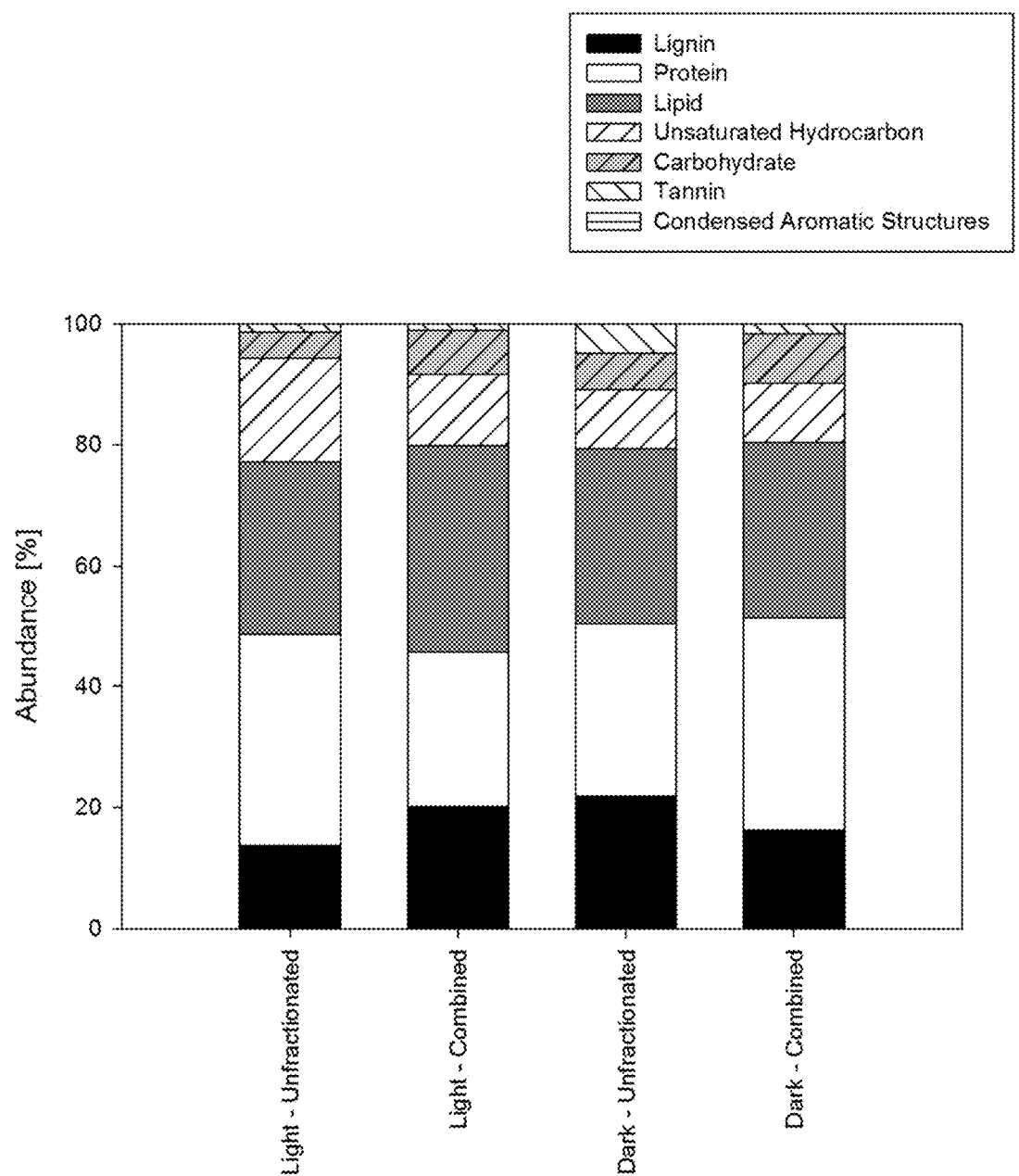
FIG. 19 shows the abundances of compound classes from cells grown in light and dark conditions.

Comparable number of m/z assigned features were found in unfractionated and AF4 combined fractions (i.e. fraction A+ fraction B+ fraction C+ fraction D) in dark cells whereas a reduction of 50% of the total m/z features was found in AF4 combined light cell samples compared to the unfractionated samples (FIG. 18). Unfractionated and AF4 combined samples shared 187 and 339 common features in light and dark samples, respectively, representing 14-28% and 32-35% of the total assigned features. The composition of light grown cells was more significantly altered by AF4 fractionation than the dark grown cells (FIG. 19). For

TABLE 19

Compound classes of unique (m/z) peaks

| | Compound Classes of unique (m/z) peaks in Percentages | | | | | | |
|---|---|---|---|---|---|---|---|
| | Lignin | Protein | Lipid | Unsaturated Hydrocarbons | Carbohydrates | Tannins | Aromatics |
| Light Grown Cells (Unique Peaks) | | | | | | | |
| Exponential Phase vs Stationary Phase (in normal media) | 23.26 | 40.97 | 15.63 | 16.32 | 2.43 | 0.69 | 0.69 |
| Exponential Phase vs Stationary Phase (both with Glucose) | 29.00 | 41.00 | 9.50 | 13.00 | 6.00 | 1.00 | 0.50 |
| Exponential Phase vs Exponents Phase (Glucose) | 22.69 | 42.02 | 15.13 | 15.41 | 3.08 | 1.12 | 0.56 |
| Stationary Phase vs Stationary Phase (Glucose) | 23.75 | 45.00 | 12.50 | 12.92 | 4.58 | 1.25 | 0.00 |
| Dark Grown Cells (Unique Peaks) | | | | | | | |
| Exponential Phase vs Stationary Phase (in normal media) | 23.33 | 46.67 | 20.00 | 6.67 | 3.33 | 0.00 | 0.00 |
| Exponential Phase vs Stationery Phase (both with Glucose) | 42.86 | 42.86 | 0.00 | 0.00 | 7.14 | 0.00 | 7.14 |
| Exponential Phase vs Exponential Phase (Glucose) | 27.50 | 37.50 | 17.50 | 7.50 | 5.00 | 2.50 | 2.50 |
| Stationary Phase vs Stationary Phase (Glucose) | 30.77 | 30.77 | 15.38 | 3.85 | 11.54 | 3.85 | 3.85 |

The compound classes unique to all compared growth phases and media conditions were dominated by the lignin and protein compound classes, comprise of the majority of the unique peaks, which were not significantly different, except in dark grown samples when the exponential and stationary phases (with glucose) were compared for lignin (Table 19). Light grown samples have higher percentages of unique peaks for the unsaturated hydrocarbons compound class than dark grown samples, in all compared media example, the lipid abundance increased from 26 to 35% after AF4 fractionation of light grown cells whereas it remained unchanged in dark grown cells. Although its abundance decreased slightly after AF4 fractionation, the number of lignin formula remained relatively constant in dark grown cells. AF4 procedure includes a focusing step in which the analytes of interest (i.e. cellular material) are concentrated on the AF4 membrane whereas the solvent and smaller analytes are eliminated. Without wishing to be bound by theory, causes of this includes lignin formula preferentially associating with higher m/z peaks in dark grown cells which were less likely to be lost during focusing through the 1 kDa AF4 membrane. The mean m/z average of protein formulae increased after AF4 fractionation (473 to 918 m/z), a result of a preferential loss of low molecular weight compounds during fractionation. Approximately 40% and 71% of protein formulae were lost in dark and light conditions, respectively.

Figure 20:
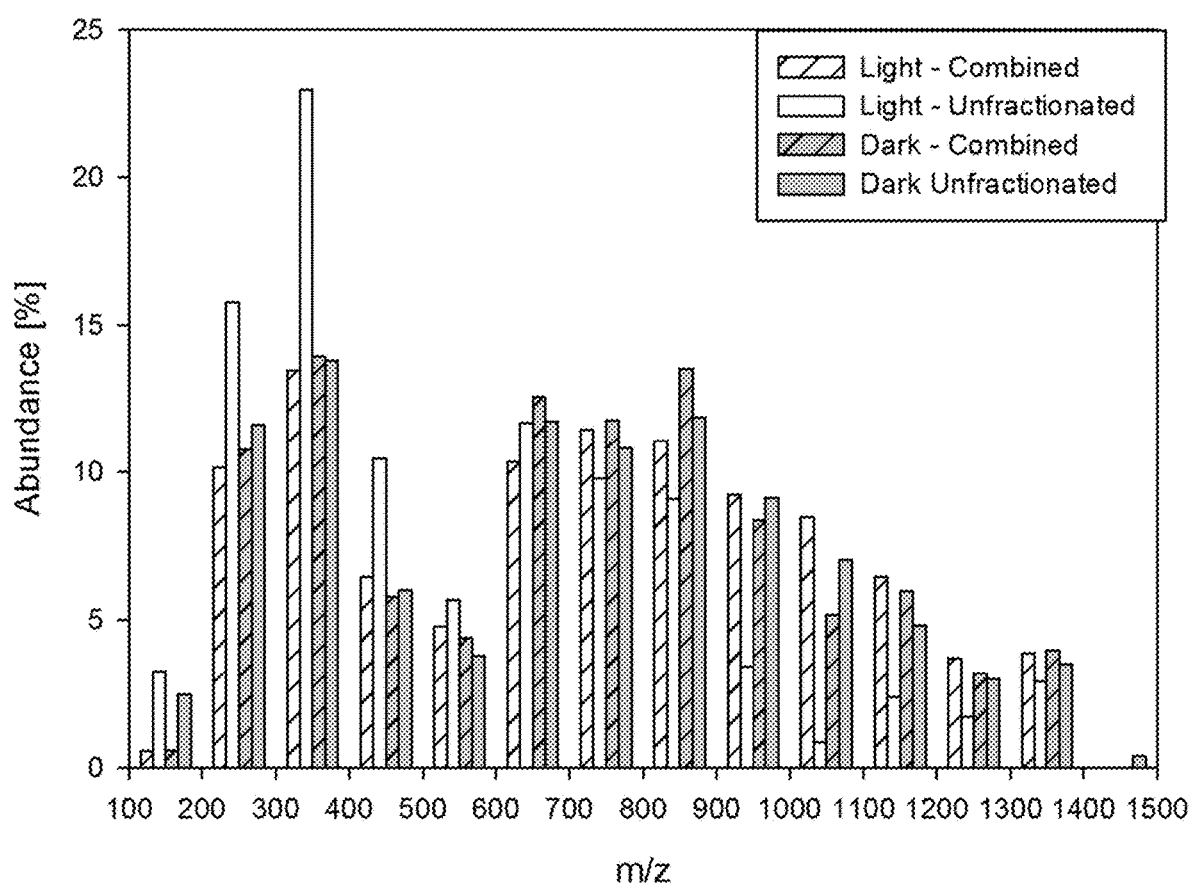
FIG. 20 shows the m/z distributions of light and dark combined fractions and unfractionated portions of *E. gracilis*.

Although most m/z values were found at 100-1000 m/z (77.4-92.1% of total assigned formulae), the abundance of features in the combined fraction of light cells decreased in the 100-700 m/z range but increased at higher m/z (800-1400 m/z) compared to the unfractionated light cells (FIG. 20). This contrasts with the dark conditions where the m/z distribution did not change drastically after AF4 fractionation. The loss of lower m/z metabolites in light conditions were likely not retained on the 1 kDa membrane during the AF4 focusing step.

934 to 2648 features (shown as "assigned peaks" in Table 20) were detected in cell fractions ranging from 150 to 1500 m/z. 349-767 features (27.5-72.7%) were commonly found in the biological duplicates. The replicates of the AF4 fractions shared 27-73% (327-715 features) and 46-56% (501-701 features) of the features associated with light and dark conditions, respectively. Comparable common features were found in a microbial study (Becker et al., 2014). The greater variability in shared features was found in the light cells fractions, likely due to uncontrollable differences in growth conditions and/or small variations in growth stage at the time of processing heterogeneity (Becker et al, 2014). The genetic machinery catered for light cells is suggested to be more sophisticated (O'Neill et al., 2015) and thus more heterogeneous in light than dark.

TABLE 20

Abundances of unique and common m/z peaks (i.e. features), and number of assigned peaks in light and dark grown biological replicates.

| | Unique features of Replicate 1 | Unique features of Replicate 2 | Common features of Replicates | Assigned Peaks |
|---|---|---|---|---|
| Light Fractions | | | | |
| A | 28.7 | 39.5 | 48.7 | 1054 |
| B | 72.8 | 33.5 | 231 | 1366 |
| C | 50.9 | 16.9 | 44.7 | 1601 |
| D | 14.9 | 16.7 | 72.7 | 934 |
| Combined | 59.0 | 47.7 | 29.9 | 1169 |
| Unfractionated | 70.4 | 59.5 | 20.6 | 2648 |
| Dark Fractions | | | | |
| A | 31.3 | 28.7 | 53.8 | 1037 |
| B | 13.3 | 38.0 | 56.6 | 1238 |
| C | 35.1 | 19.2 | 56.2 | 1153 |
| D | 21.5 | 38.9 | 52.4 | 1033 |
| Combined | 19.7 | 48.2 | 46.0 | 1090 |
| Unfractionated | 27.4 | 28.0 | 56.6 | 1355 |

Figure 21:
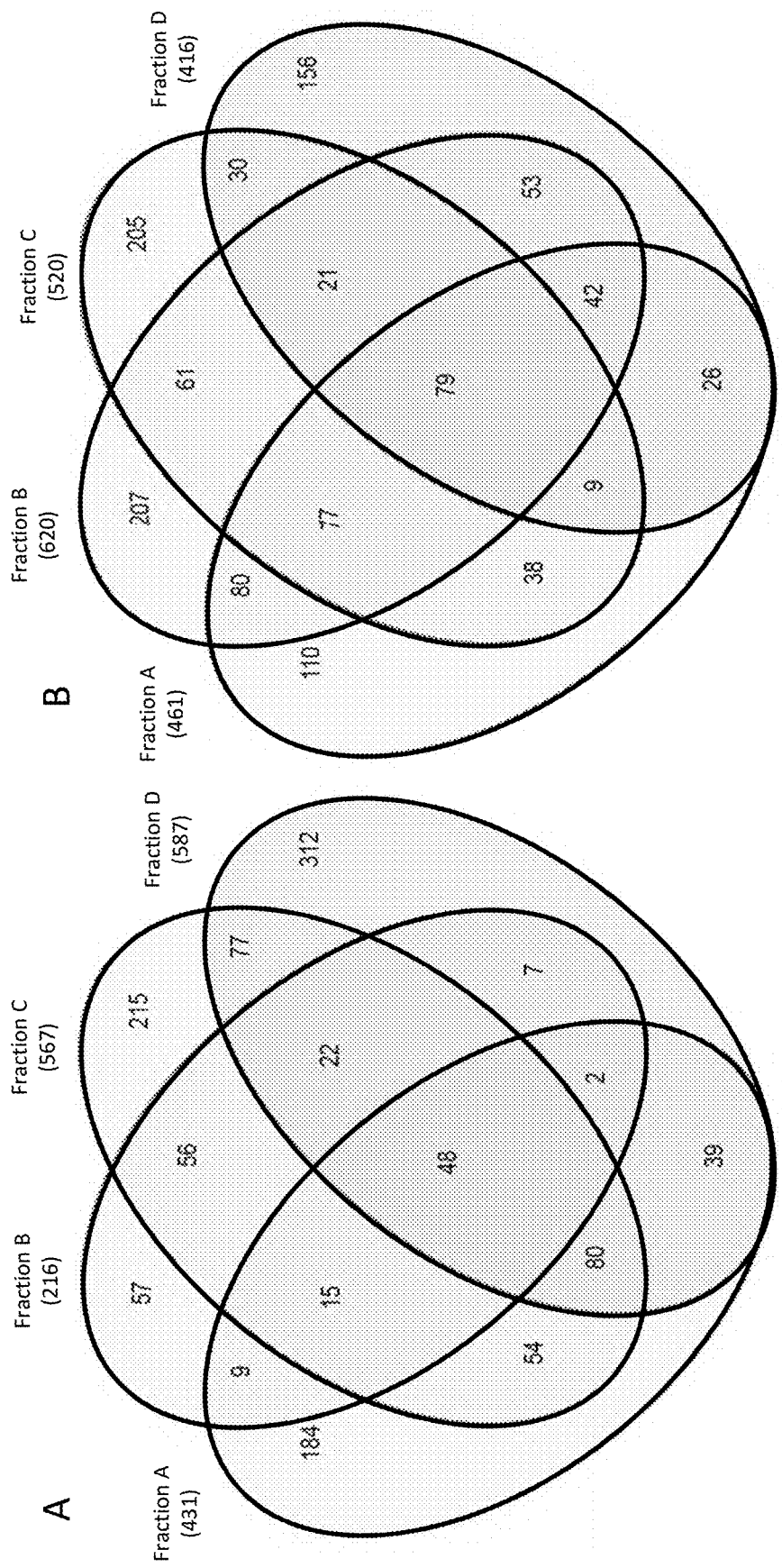
FIG. 21 shows the Venn diagrams for the m/z values in (A) light and (B) dark grown fractions.

Venn diagram analyses of the four AF4 fractions revealed only 79 (11.7%) and 48 (6.3%) common features in all light and dark fractions, respectively (FIG. 21). Most features were unique to one specific AF4 fraction, showing that the AF4 method allows the isolation of unique cellular features. The light fractions showed more unique features than the dark fractions (except fraction B), with light fraction D showing the most unique features (312).

In terms of compositional abundance, protein, lipid, lignin, unsaturated hydrocarbons, and carbohydrates dominated the composition of unique peaks in fractions grown under light and dark conditions (FIG. 22). The lower lipid abundances in dark grown cells relative to light grown cells ($p<0.05$; except fraction B), without wishing to be bound by theory, could be explained by the diversion of lipids to photosynthetic pathways upon differentiation of the cells (Matsuda et al., 2011; Schwartzbach and Shigeoka, 2017). Comparable results were found in previous studies (Rosenberg and Pecker, 1964; Constantopoulos and Bloch, 1967) where lipid content in *Euglena* was altered with increasing light. Lipid characteristics such as higher reduction state, hydrophobic character and the ability to be efficiently packed into the cell and generate high amounts of energy upon oxidation, suggest this class is a reserve for rebuilding the cell after stress has been alleviated (Moralez-Sanchez et al., 2016). Without wishing to be bound by theory, this could explain why lipid abundances were higher in *Euglena* dark fractions than light fractions as previously shown (Li et al., 2014). The greater protein abundance in light cells may be related to the active photosynthetic light system as synthesis of the precursor molecules for the light harvesting chlorophyll a/b binding protein of photosystem II (LHCPII) increased 50-100-fold upon exposure of dark grown resting *Euglena* cells to light (Kishore and Schwartzbach, 1992).

When comparing AF4 fractions, the abundance of protein compounds in light conditions decreased from fraction A to D (i.e. with increasing retention time and thus molecular weight; Schimpf et al., 2000), while the converse was found for lipid compounds ($p<0.05$; FIG. 22A). The increase in proportion of lipids in different cellular fractions (A-D) indicated larger size cellular material was lipid-rich. A decrease in proportion of protein compounds in different fractions (A-D) could be due to organelles of higher molecular weight exhibiting lower protein content. No significant change in protein and lipids was found in AF4 dark fractions ($p<0.05$; FIG. 22B). The dark and light cellular fractions (A-D) did not show any significant differences in double bonded structures (DBE) or O/C ratios, indicating comparable levels in aromatic and oxygenated compounds. Significant differences in m/z values were found ($p<0.05$), with higher m/z values in the dark fractions. This Example shows that fraction C from dark grown cells was the most enriched in lignin+protein+carbohydrates ($p<0.05$), which are compound classes associated with metal binding.

Figure 23:
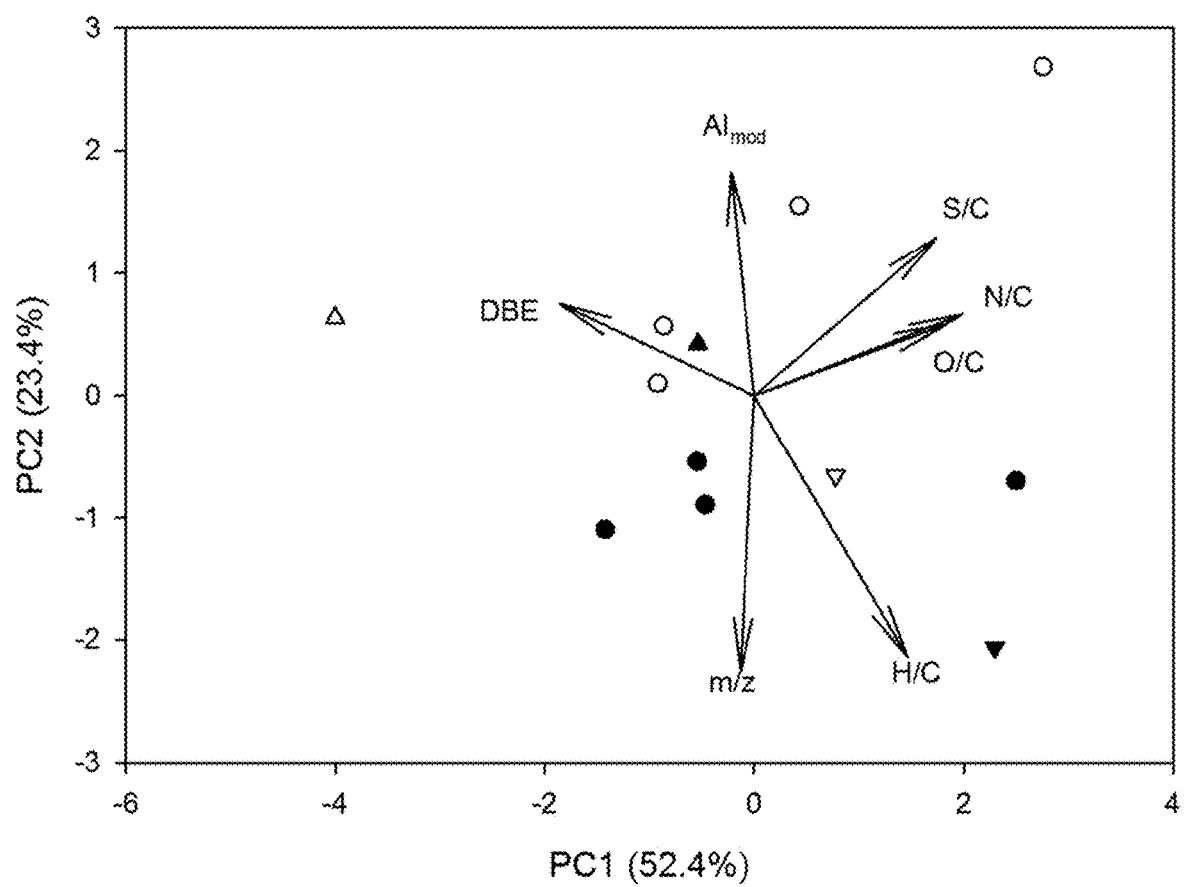
FIG. 23 shows the multivariate variation among cellular composition of AF4 fractions in terms of compound class abundances in light (open) and dark (closed) conditions. The combined and unfractionated samples are indicated by a triangle up and a triangle down, respectively. Vectors indicate the direction and strength of each variable to the overall distribution.

PCA analysis of elemental ratios (O/C, H/C, N/C, and S/C), Almod, double bonded structures (DBE) and m/z in fractions A-D revealed distinct patterns between light and dark fractions (FIG. 23). The first two principal components (PC) represented 52.4% and 23.4% of the total variance, respectively. Light and dark fractions were mainly separated along the PC2 axis. The dark fractions (except fraction A) were characterized by higher m/z and lower Almod than the light fractions, showing the significant differences in molecular composition of cells grown in light and dark conditions. The positive PC1 and PC2 scores of light fractions B and C indicated the prevalence of O-, N- and S-rich compounds compared to the dark fractions B and C. Light fractions A and D were strongly shifted to the left quadrant, revealing their greater abundance of DBE compared to light fractions B and C.

IV. Conclusions

The presence of carboxylic and proteins, functional groups typically involved in transition metal and rare earth metal (REE) binding, were confirmed by FTIR spectroscopy in exponential and stationary growth phases of dark and light grown cultures. No major differences in FTIR-based structural composition were found between growth phases. The structural composition of *E. gracilis* cells based on Orbitrap Q-Exactive showed that lignin, carbohydrate and aromatic were the most abundant in dark grown conditions with glucose supplementation. This confirms the differences in physiological states of the cell, in different growth and culture conditions. Based on the results presented, conditions that would potentially facilitate the most efficient metal removal, in particular for REE, would be dark grown *E. gracilis* cells grown with glucose supplementation at the exponential phase of growth. Using constraints to identify compound classes (lipid, protein, tannin, carbohydrate, aromatics, and unsaturated hydrocarbons) is a novel way of determining the different families of compounds in algal cells. The lignin, aromatics, protein and carbohydrate compound classes are potential ones for REE removal via biosorption.

Molecular composition was different between AF4 fractions with the aromatic character being enhanced in some AF4 fractions. Based on the composition of fractionationed cells, fraction C of dark grown cells was the most favorable fraction for metal binding and thus metal removal and extraction.

A greater variability in features shared by AF4 fraction in cells grown in light conditions was found. Dark conditions were superior in terms of the cellular abundance of aromatic+protein+carbohydrates compounds compared to light conditions, showing that *Euglena* cultured under this condition would be most useful for extraction of metals.

Figure 24:
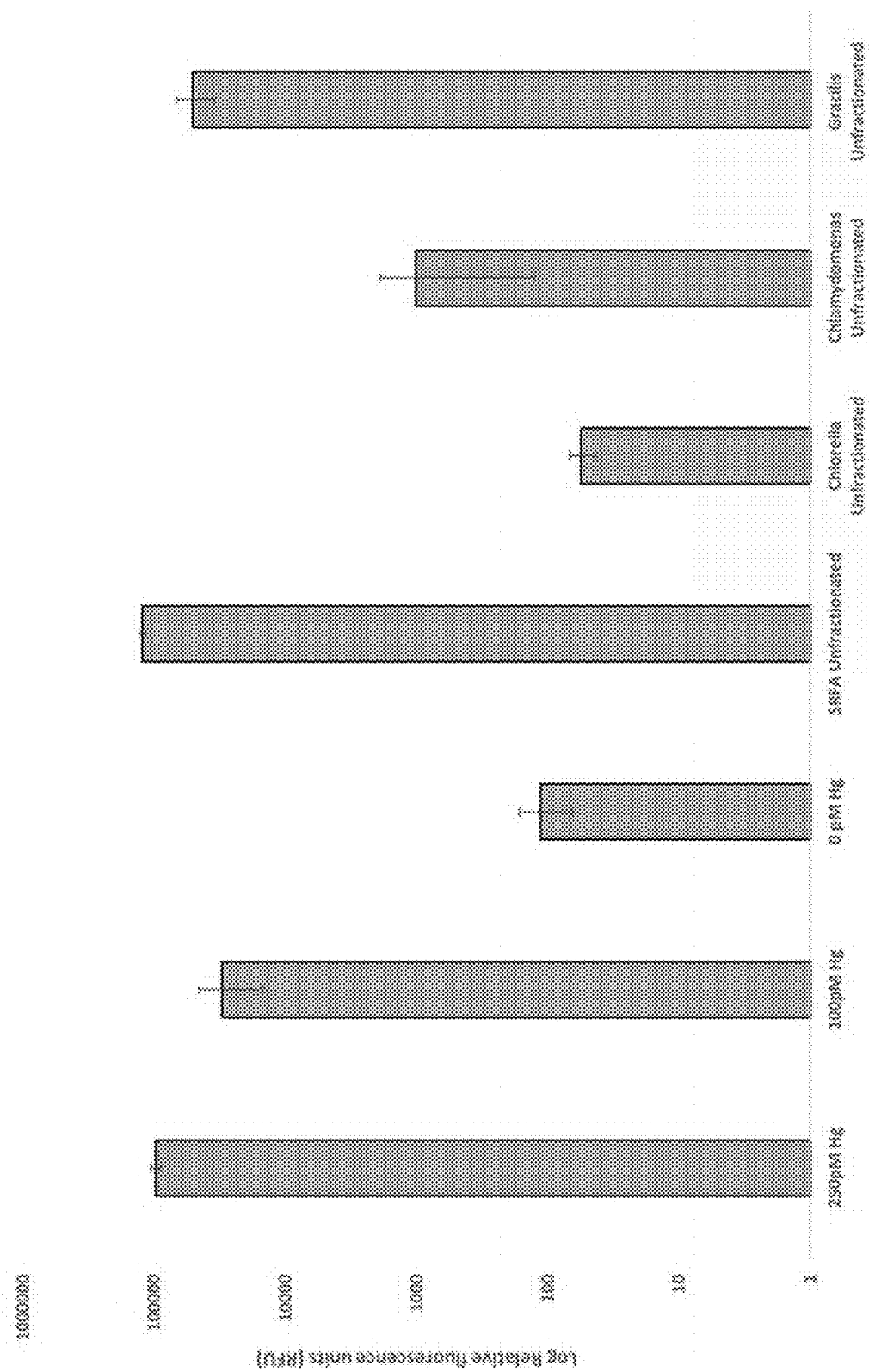
FIG. 24 shows bioluminescence response as a function of different unfractionated algae exposed to 250 pM of $Hg(NO_3)_2$.

Example 4: Use of Diffusive Gradient in Thin Films (DGTs) Technologies, Dialysis Algal Cells or Exudates, for Metal Remediation in Waters 1. Introduction The size of the *Euglena* exudates may be small enough to diffuse through *E. coli* cell membranes. *E. coli* cells have been used as biosensor of Hg mobilization (Chiasson-Gould et al., 2014). FIG. 24 shows that bioluminescence induced by free 250 pM Hg or 250 pM Hg exposed to *Euglena* exudates in *E. coli* biosensor was comparable. Therefore, if the *Euglena* exudates are to be used in a filtration apparatus to remove metal, a system should be in place to ensure that the exudates do not diffuse out of the apparatus. With this in mind, the use of dialysis bag was investigated to determine whether it could prevent exudates diffusion. In the present disclosure, dialysis bag studies showed that it was feasible to retain the exudates in the dialysis bags.

The size of the *Euglena* exudates may be small enough to diffuse through *E. coli* cell membranes. *E. coli* cells have been used as biosensor of Hg mobilization (Chiasson-Gould et al., 2014). FIG. 24 shows that bioluminescence induced by free 250 pM Hg or 250 pM Hg exposed to *Euglena* exudates in *E. coli* biosensor was comparable. Therefore, if the *Euglena* exudates are to be used in a filtration apparatus to remove metal, a system should be in place to ensure that the exudates do not diffuse out of the apparatus. With this in mind, the use of dialysis bag was investigated to determine whether it could prevent exudates diffusion. In the present disclosure, dialysis bag studies showed that it was feasible to retain the exudates in the dialysis bags.

II. Experimental Procedures

A. Algal Culture and Sample Preparation

*Euglena gracilis* cells were cultured at 29° C. under a 18:6 hr light:dark (2000-2500 lax) cycle in 500 mL autoclaved modified Hutner medium (*Euglena gracilis* medium or EGM; Dunstaffnage Marine Laboratory Culture Collection of Algae and Protozoa). The cells ($10^6$ cells/mL) were harvested in the exponential growth phase and their exudates isolated using precombusted 0.2 μm nitrocellulose filters. Suwannee River fulvic acid (SRFA) standard obtained from the International Humic Substances Society (IHSS) was diluted in Milli-Q water to a final concentration of 7 mg·$L^{-1}$.

To determine influence of growth conditions on metal sorption *Euglena gracilis* cells were cultured as above in normal or Hg-amended (0.5 ppb) autoclaved EGM at pH 3.60. For cells cultured in Hg-amended medium (i.e. Hg-adapted cells), the medium was spiked with 0.5 ppb Hg in freshly autoclaved medium at the end of each exponential phase. Normal and Hg-adapted cells after 2-4 (younger generation) and 11 cycles (older generation) were put in dialysis bags and immersed in normal autoclaved medium spiked with metals and continuously stirred for three days. The concentrations of metal in the cells were measured using triple quadrupole ICP-MS (Agilent 8800, Trent Water Quality Centre).

B. Dialysis Bag

Five milliliter membrane tubing (0.1-0.5 kDa Biotech Cellulose Ester; Spectrum Labs) were closed using locking nylon membrane clamps. Before use, the dialysis membranes were left in Milli-Q water overnight. To assess the actual cutoff of the dialysis bags, a series of known molecular weight macromolecules (rhodamine-B, vitamin B-12, cytochrome, lysozyme and albumin) was used. Five milliliter of each macromolecule solution (~1 g·$L^{-1}$; n=2-4) was loaded in the dialysis bag and continuously stirred at 600 rpm for 3 to 5 days. Absorbances in the macromolecule feed solution ($a_{initial}$) and in the dialysate after 3 to 5 days ($a_{dialysate}$) were measured on a 2550 UV-visible diode array spectrophotometer (Shimadzu) equipped with a 10-cm quartz cell. The rejection rate was calculated as follows:

$$\% R = \frac{a_{initial} - a_{dialysate}}{a_{initial}} \times 100$$

Five milliliter of samples (i.e. *Euglena* cells or exudates or SRFA) were loaded into dialysis bags with nominal cutoffs of 0.1-0.5 kDa. The bags were placed in a continuously stirred 500 mL beaker containing freshly autoclaved (cells and exudates) or Milli-Q water (SRFA). The beakers were continuously stirred for 3-5 days at room temperature.

C. Hg-Amended Growth Condition

The influence of growth conditions on metal sorption *Euglena gracilis* cells was determined by culturing the cells as above in normal or Hg-amended (0.5 ppb) autoclaved EGM at pH 3.60. For cells cultured in Hg-amended medium, the medium was spiked with 0.5 ppb Hg in freshly autoclaved medium at the end of each exponential phase. Normal and Hg-adapted cells after 2-4 (younger generation) and 11 cycles (older generation) were put in dialysis bags and immersed in normal autoclaved medium spiked with metals and continuously stirred for three days. The concentrations of metal in the cells were measured using triple quadrupole ICP-MS (Agilent 8800, Trent Water Quality Centre). The metal sorption ratio is calculated as follows:

$$\text{Metal sorption ratio} = \frac{\text{Concentration of metal in the cells after three days}}{\text{Initial concentration of metal in the cells}}$$

D. Asymmetrical Flow Field-Flow Fractionation

Asymmetrical flow field-flow fractionation (AF4) equipped with a 300 Da polyethersulfonate (PES) membrane, and a UV-Visible diode array detector was utilized (Guéguen and Cuss, 2011). The molecular weight (MW) calibration was performed with macromolecules: laser grade rhodamine B (479 Da; Acros Organics), Trypan blue (961 Da; Sigma-Aldrich), vitamin B12 (1330 Da; Sigma-Aldrich), bovine heart cytochrome C (12,400 Da; Sigma-Aldrich) and hen egg white lysozyme (14,000 Da; Fluka), were prepared in the carrier solution. A log-log retention time versus MW calibration curve was plotted and subsequently used to calculate the MW of samples.

E. Diffusive Gradient in Thin Films (DGTs) Technologies

Diffusive gradient in thin films (DGTs) technologies function as passive samplers that concentrate metals from dissolved, aquatic phases (Davison and Zhang, 1994). Currently, synthetic Chelex binding gels serve as the site of metal interaction and concentrations; however, manufacturing Chelex gels requires many chemicals and can be time consuming. To combat this, this disclosure shows the incorporation of non-living Euglena cells and/or exudates released by Euglena as the new binding sorbent for the passive concentration and removal of metals (FIGS. 25A and B). The DGT samplers were composed of a binding gel layer (immobilized Euglena cells or Chelex resin), a 0.5 mm diffusive acrylamide-based gel layer and a 0.45 um cellulose nitrate filter. By embedding Euglena cells in an immobilized matrix, this disclosure shows that the need for synthetic Chelex gels is omitted. The disclosure provides an all organic solution for metal removal. This biosorbent DGT is useful in contaminated sites to monitor, accumulate and eventually remove metals from contaminated aquatic sources.

The E. gracilis cells were harvested at the exponential phase and centrifuged at 4000-5000 rpm for 6 min and washed three times with deionized water to remove any remaining culture medium from the cells. Cells were lyophilized overnight and mechanically homogenized via mortar and pestle.

The DGT preparation was conducted in metal-free 10,000 class (ISO 7) clean room to minimize metal contamination. In order to prepare DGT resin binding gels, 3 g of Euglena cells or Chelex-100 resin was added to 10 mL polyacrylamide gel (15% acrylamide—FisherScientific, 0.3% DGT cross-linker—DGTResearch) in a pre-cleaned polypropylene tube. 50 μL of 10% (w/w) APS (>98%, FisherScientific) and 15 TEMED (FisherScientific) were added and mixed well. The gels were cast immediately between glass plates spaced with 0.25 mm thick, acid-bathed, polystyrene spacers. Following polymerization (60 min at 40-45° C.), the gels were hydrated in MilliQ water for at least 24 h. The MilliQ water was changed several times to remove any impurities and unreacted reagents. The gels were stored in 0.1M $NaNO_3$ solution.

DGT devices were submerged into the stirred multi-element solution (50 ppb), kept at 25° C., for different periods of time (e.g. 1, 2, 3, 4, and 5d). At each sampling interval, two DGT units were removed from the solution. Binding gels were eluted in 1 M double distilled nitric acid for 24 h before ICPMS analysis (Agilent 8800, Trent Water Quality Centre). Indium and rhodium were used as internal standards. The accuracy of the ICP-MS measurements was assessed using SLRS-5 reference water (National Research Council, Canada). The measured metal concentrations were within 5% of the certified values. Blank concentrations were assessed by measuring the mass of metal present in binding gels.

III. Results and Discussion

A. Dialysis of Macromolecules

The retention characteristics of dialysis bags may vary with the operating conditions. Thus, the rejection rate (% R) was determined by integrity tests based on macromolecules with a known molecular weight MW (Table 21). Rejection rates averaged 99 to 100% for all macromolecules supporting that compounds with MW greater than the smaller macromolecule MW (i.e. Rhodamine B) are retained in the dialysis bags. As SRFA (1.1 kDa) and Euglena exudates (1.6 kDa) have higher MW than Rhodamine-B, they should be preferentially retained in the dialysis bags.

TABLE 21

Retention characteristics of dialysis bags

| Standard | Molecular weight (kDa) | % R |
|---|---|---|
| Rhodamine B | 0.5 | 99 |
| Vitamin B12 | 1.3 | 99 |
| Cytochrome C | 12 | 100 |
| Lysozyme | 14.3 | 100 |
| Albumin | 66 | 100 |

B. Dialysis of Euglena and SRFA

Figure 26:
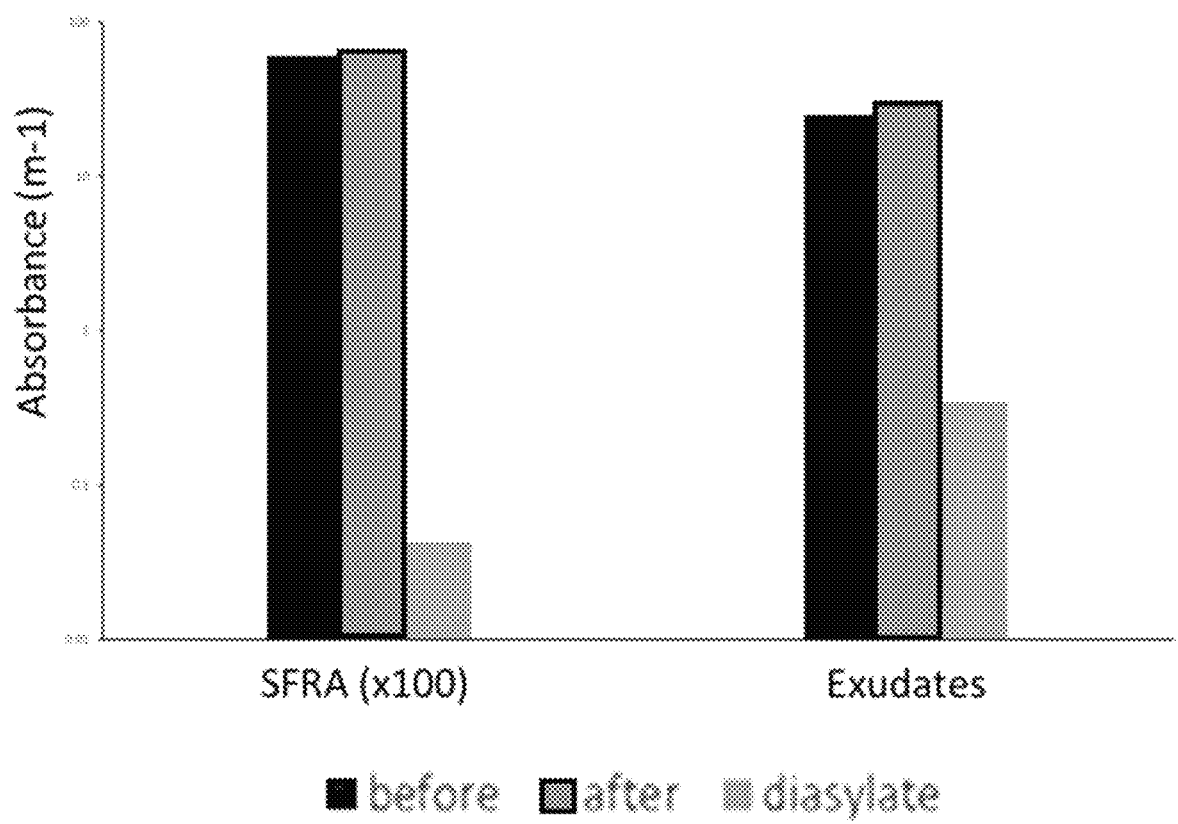
FIG. 26 shows the performance of dialysis bag to retain small (SRFA), medium (*Euglena* exudates) and large compounds (*Euglena* cells).

The performance of dialysis bag to retain small (SRFA), medium (Euglena exudates) and large compounds (Euglena cells) was assessed in laboratory settings. >99% of SRFA and Euglena exudates remained in the dialysis bags after 5 days (FIG. 26), congruent with MW results. Only 0.1 to 1.2% of the original material contained the dialysis bag was found in the dialysate after 4 days (FIG. 26). The Euglena exudates dialysate was slightly more enriched compared to SRFA due to differences in MW distribution (FIG. 27). The <0.5 kDa fraction was slightly more abundant in Euglena exudates than SRFA as confirmed by the higher signal reported in the dialysate (FIG. 27).

Figure 28:
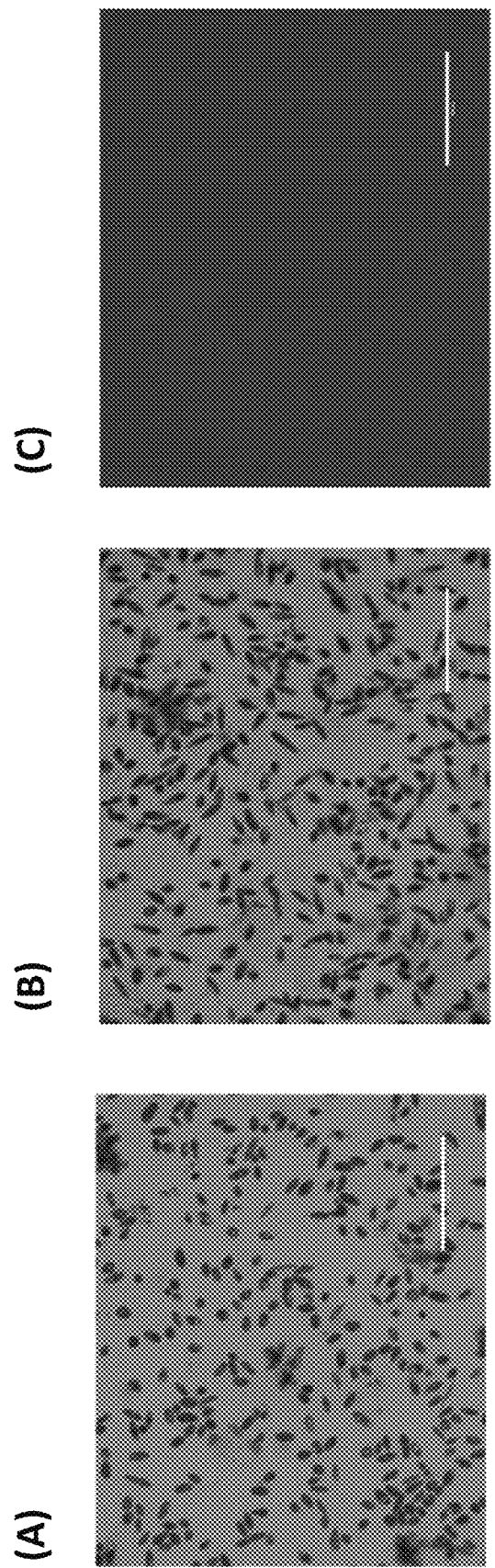
FIG. 28 shows that no *Euglena* cells were noticeable in the dialysate after 4 days (C). All original cells (A) were kept in the dialysis bag after 4 days (B).

Similarly, no Euglena cells were noticeable in the dialysate after 4 days (FIG. 28C). Together these results showed that Euglena cells and exudates in dialysis bags are efficiently deployed in wastewaters or mining process water to remove contaminants.

Figure 29:
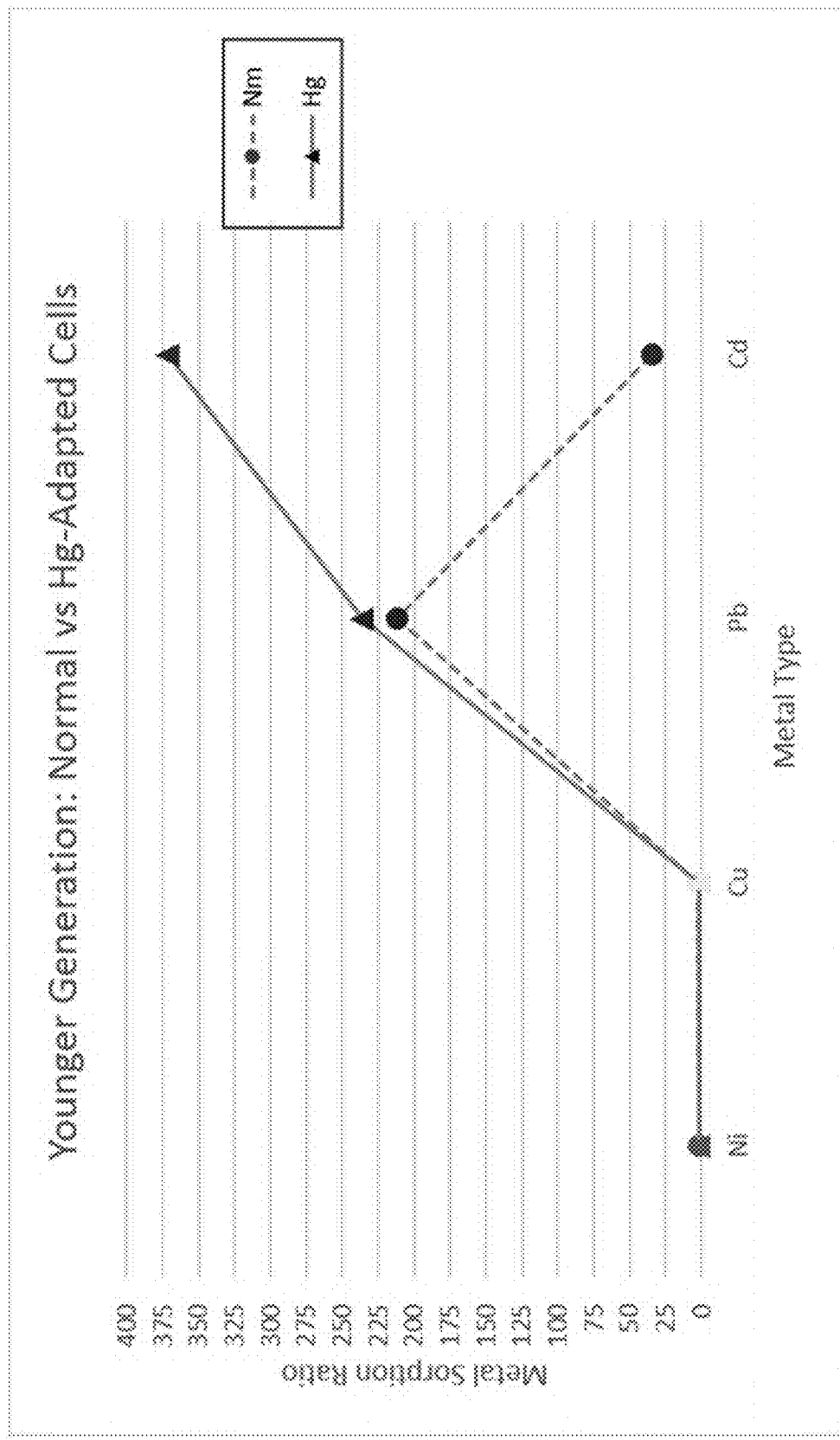
FIG. 29 shows change in metal sorption of the younger generation cells grown in normal (Nm) versus Hg-adapted *Euglena gracilis* cells.

Next, Euglena cells contained in dialysis bags were used to assess the effects of Hg-adaptation on metal sorption. In younger generation cells (2-4 cycles), higher sorption of Pb and Cd, but not Ni and Cu, was found in Hg-adapted cells (FIG. 29). The sorption ratio was relatively different for Cd, where the Hg-adapted cells showed an approximately ten times higher sorption ratio in comparison to normal cells. The sorption increased as follows:

Normal cells Ni=Cu<Cd<Pb

Hg-adapted cells Ni=Cu<Pb<Cd

Figure 30:
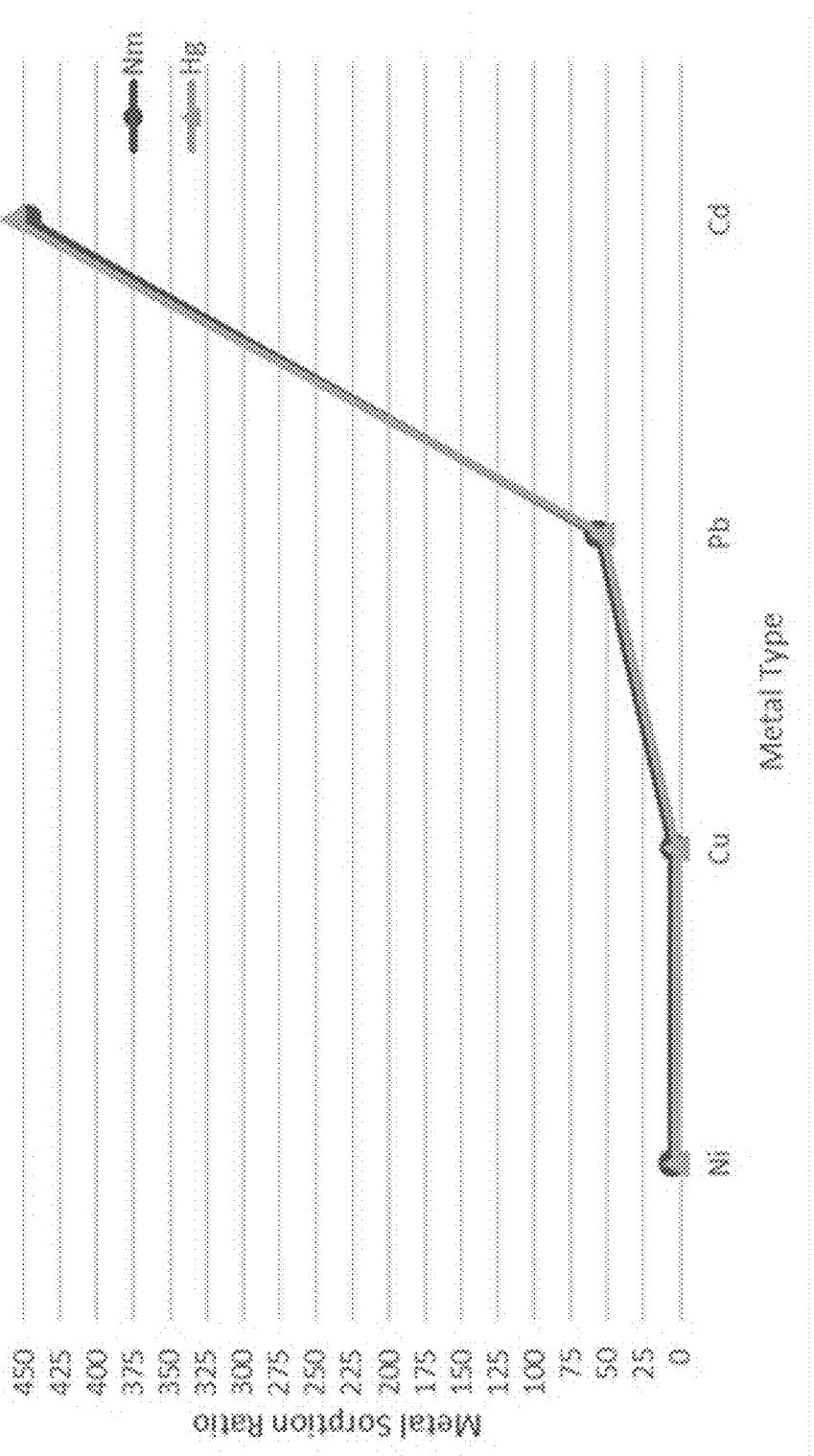
FIG. 30 shows change in metal sorption of the older generation grown in normal (Nm) versus Hg-adapted *Euglena gracilis* cells.

By contrast, in older generation cells (11 cycles), no significant change in metal sorption was found between normal and Hg-adapted Euglena cells (FIG. 30). For the older generation cells in both culture conditions, the trend was as follows: Ni≅Cu<Pb<Cd.

Figure 31:
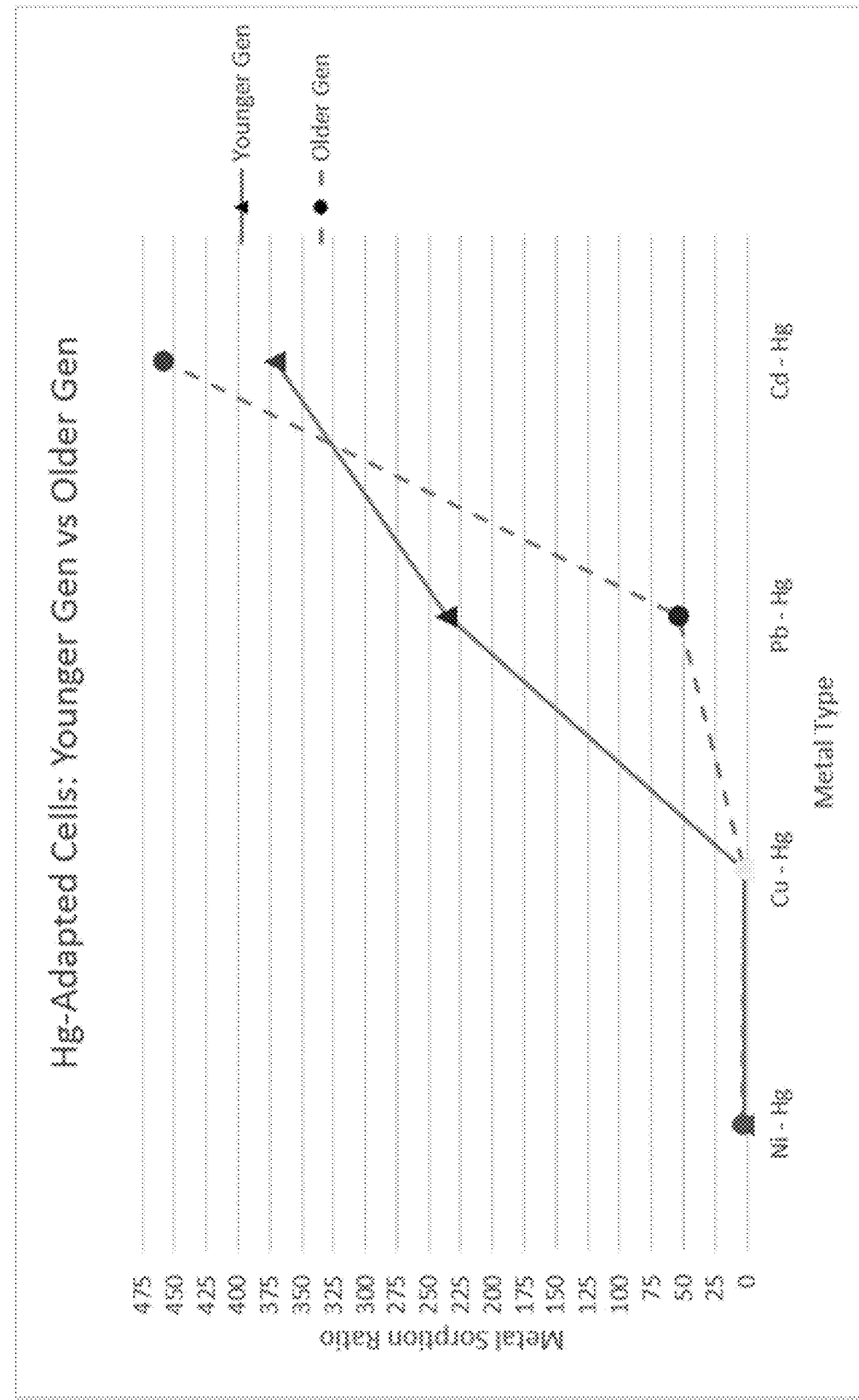
FIG. 31 shows metal sorption ratio of the younger and older generations of Hg-adapted *Euglena gracilis* cells.

A comparison between younger generation and older generation Hg-adapted cells found that younger generation cells showed a 4.5-fold increase in Pb sorption relative to the older generation cells (FIG. 31). In contrast, greater metal sorption was associated with the older generation for Cd in Hg-adapted cells. No significant difference in Ni and Cu sorption was found between younger and older generations of Hg-adapted cells.

C. Euglena-DGT

Figure 32:
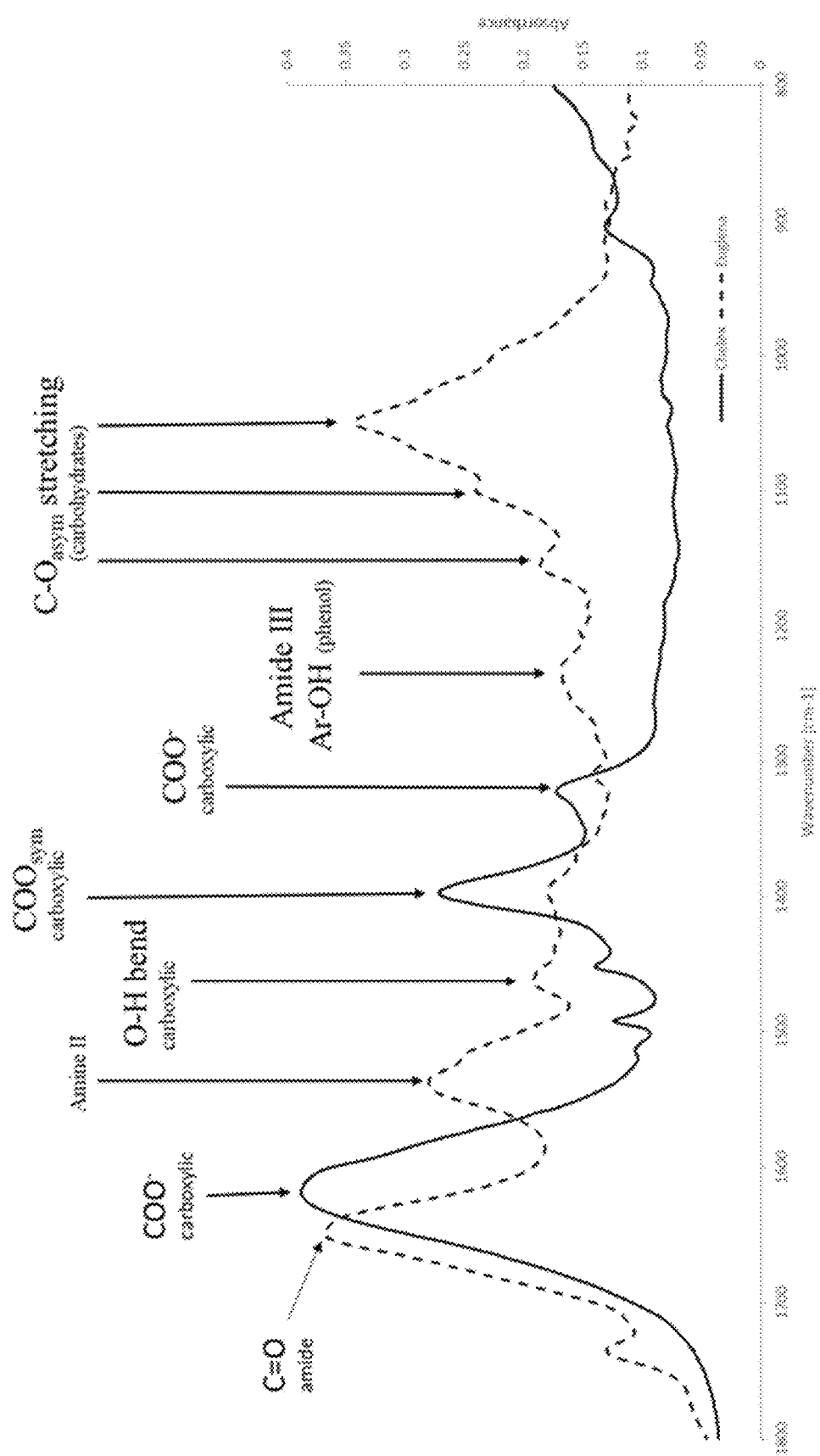
FIG. 32 shows the FTIR spectra of Chelex (solid) and *Euglena* cells (dashed).
Figure 33:
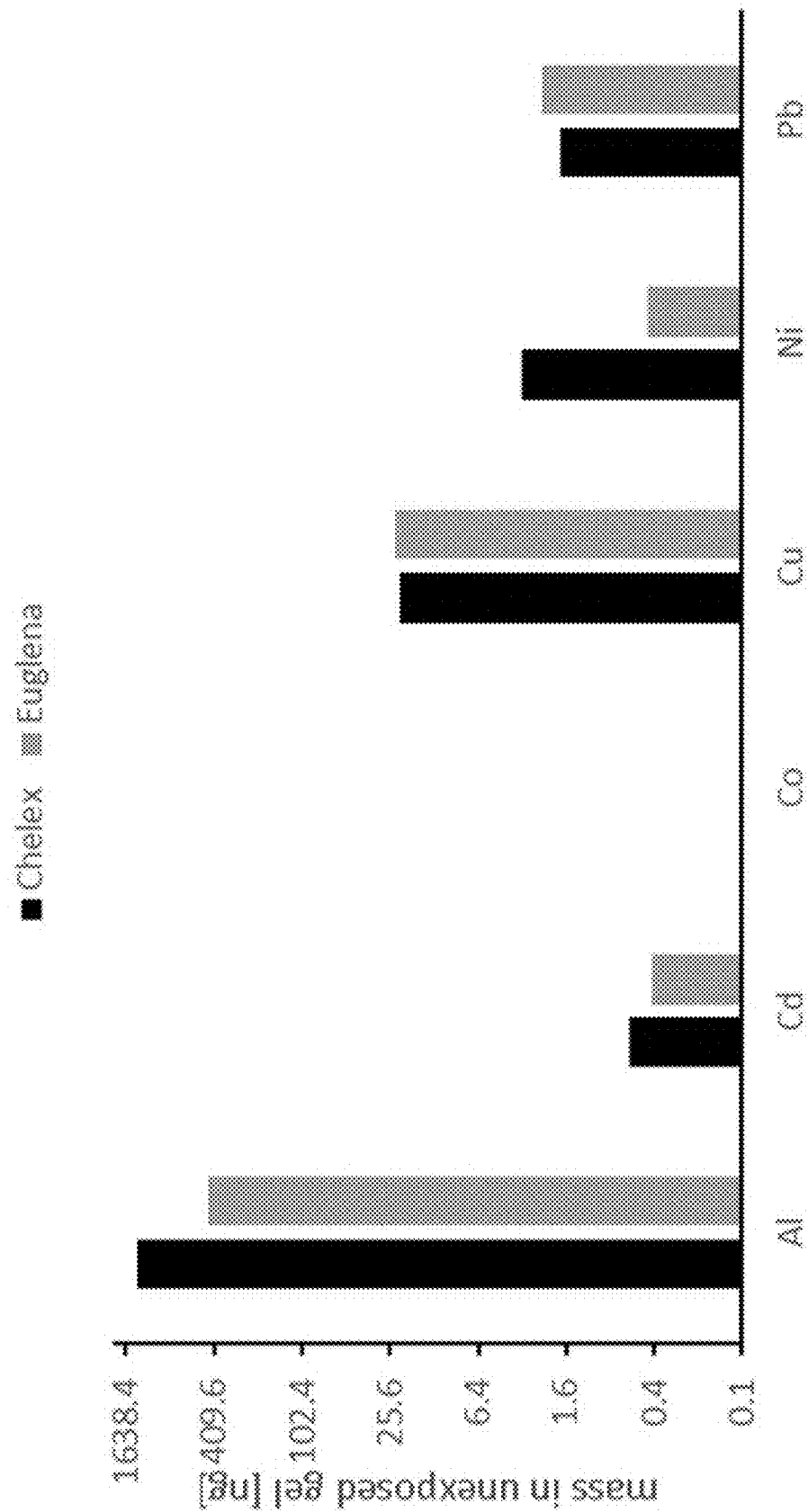
FIG. 33 shows the accumulated metal mass in unexposed DGT-Chelex and DGT-*Euglena* resin.
Figure 34:
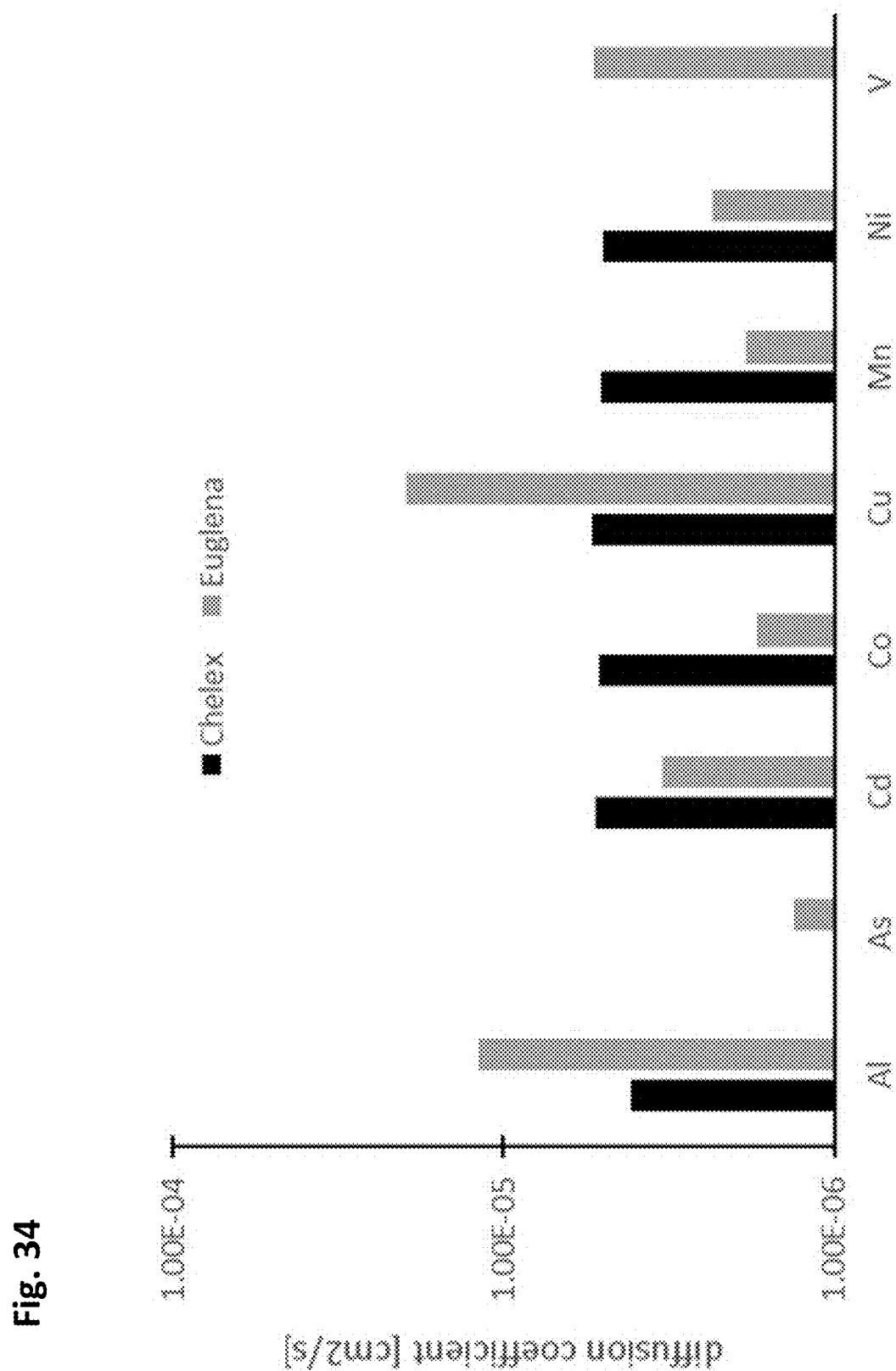
FIG. 34 shows the diffusion coefficient of DGT-*Euglena* binding resin at 20° C.

The FTIR spectra of lyophilized *E. gracilis* showed several bands in the 1900 to 500 cm$^{-1}$ range (FIG. 32), indicative of functional groups. The bands at 1310 (COO), 1394 (COO$_{sym}$) and 1450 cm$^{-1}$ (O—H bend) were well defined in Chelex-100 compared to *Euglena*, confirming that carboxylic functional groups are dominant in Chelex-100. The absorbance of these carboxylic bands was reduced in *Euglena*, indicating that they were found in *Euglena* but not as abundant as in Chelex-100. The bands at 1044, 1110 and 1197 cm$^{-1}$ (C—O$_{asym}$) represented carbohydrates and was only found in *Euglena*. The presence of carbohydrates was congruent with algal metabolomics process. The amide III and Ar—OH (1232 cm$^{-1}$) was also unique to *Euglena*. These FTIR results showed that *Euglena* possessed all functional groups (i.e. carboxylic, phenolic, amide and sulfur) required in metal binding.

The triplicate DGT units deployed for 72 h in 50 ug L$^{-1}$ showed that all metals were accumulated onto both *Euglena* and Chelex binding gels (Table 22). Type-B metals (Cd and Pb) were equally accumulated on both binding gels whereas the intermediate metals (Co and Ni) were preferentially accumulated on the DGT-Chelex units. Cu was more accumulated on DGT-*Euglena* units, without wishing to be bound by theory, could be due to its complexation with 0-, N- and S-containing functional groups. No N- (FIG. 22) and S-containing functional groups were found on Chelex resin.

TABLE 22

Accumulated mass (M) on DGT-*Euglena* resin gels as a function of time (in days) metal

| | |
|---|---|
| Al | M = 73.07 t + 132 (r$^2$ = 0.95) |
| V | M = 32,86 t + 11.28 (r$^2$ = 89) |
| Mn | M = 11.41 t + 13.91 (r$^2$ = 0.81) |
| Co | M = 10.59 t + 11.54 (r$^2$ = 0.76) |
| Ni | M = 14.37 t + 17.83 (r$^2$ = 0.72) |
| Cu | M = 120.99 t + 0.00 (r$^2$ = 0.93) |
| As | M = 8.10 t + 10.47 (r$^2$ = 0.71) |
| Cd | M = 20.45 t + 6.29 (r$^2$ = 0 91) |

Based on the diffusion properties, the mass of metal accumulated onto the *Euglena* resin (M) was proportional to the exposure time (0.71<r$^2$<0.98, FIG. 24), implying that increasing exposure time increased metal extraction. The diffusion coefficient values for metals ranged from 1.32× 10$^{-6}$ to 1.97×10$^{-5}$ at 21° C. (FIG. 25). The diffusion coefficients for Al and Cu were significantly greater in DGT-*Euglena* than in DGT-Chelex. Unlike DGT-Chelex, the DGT-*Euglena* showed a linear accumulation of metalloids, including As and V, showing that DGT-*Euglena* was suitable for metalloid extraction.

IV. Conclusions

The Hg-adaptation experiment showed that metal sorption was dependent on the growth conditions, cell generation, and the metal. Pb and Cd sorption, unlike Ni and Cu sorption, was enhanced in Hg-adapted cells, supporting that Hg-induced stress changed the cellular sorption properties. The sorption enhancement was mainly associated with cells recently grown in the presence of Hg, which indicated a temporal element for the metal sorption ability of *Euglena* cells following Hg-adaptation.

The application of the presented methods could ultimately be applied for the sequestration and immobilization of metal ions in contaminated waters. The trapping of dissolved organic matter (DOM) within the porous dialysis bag allows for the internalization of metal ions from the environment and the subsequent binding to exudates and algal cells trapped within the bag. This approach is useful for any source of microorganism derived DOM larger than the molecular weight cut-off. By trapping cells and/or algal exudates within the dialysis bag, dual remediation effect can occur whereby there is 1) immobilization of larger molecular weight contaminant-DOM complexes that remain in the bag and 2) the uptake/sorption of contaminant-DOM complexes by algal cells.

The immobilization of *Euglena* cells allows for the extraction and sequestration of metals and metalloids from the environment. This approach is useful for any cellular fractions or metabolites from microorganisms. The skilled person would readily recognize that the DGT-*Euglena* is useful for any metals and metalloids that can bind to O-, N- and S-groups present on cells and metabolites.

While the present disclosure has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE SPECIFICATION

Abbas, S. H., Ismail, I. M., Mostafa, T. M., and Sulaymon, A. H., 2014. Biosorption of heavy metals: a review. Journal of Chemical Science and Technology 3, 74-102.

Becker, J. W., Berube, P., Follett, C., Waterbury, J., Chisolm, S., Delong, E., and Repeta, D. (2014). Closely related phytoplankton species produce similar suites of dissolved organic matter. Front Microbiol 5: 111. doi:10.3389/fmicb.2014.00111.

Burdin, K. S., and Bird, K. T., 1994. Heavy metal accumulation by carrageenan and agar producing algae. Botanica Marina 37, 467-470.

Chen, Z., Ma, W., and Han, M., 2008. Biosorption of nickel and copper onto treated alga (*Undaria pinnatifida*): application of isotherm and kinetic models. Journal of Hazardous Materials 155, 327-333.

Chiasson-Gould S. A., Blasis M. J., and Poulain J. A., 2014. Dissolved Organic Matter Kinetically Controls Mercury Bioavailability. Environ. Sci. Technol. 48, 3153-3161.

Constantopoulos, G., and Bloch, K. (1967). Effect of light intensity on the lipid composition of *Euglena gracilis*. J. Biol. Chem., 242(15), 3538-3542.Cordero, B., Lodeiro, P., Herrero, R., de Vicente, S., and Esteban, M., 2004. Biosorption of cadmium by *Fucus spiralis*. Environmental Chemistry 1, 180-187.

Davison, W., Zhang, H., 1994. In situ speciation measurements of trace components in natural waters using thin-film gels. Nature 367, 546e548.

Donmez, G., Aksu, Z., Ozturk, A., and Kutsal, T., 1999. A comparative study on heavy metal biosorption characteristics of some algae. Process Biochemistry 34, 885-892.

Doshi, H., Ray, A., and Kothari, I. L., 2007. Bioremediation potential of live and dead *Spirulina*: spectroscopic, kinetics and SEM studies. Biotechnology and Bioengineering 96, 1051-1063.

Fogg, G. E., 1957. Relationships between metabolism and growth in plankton algae. Microbiology, 16(1), 294-297.

Fomina, M., and Gadd, G. M., 2014. Biosorption: current perspectives on concept, definition and application. Bioresource Technology 160, 3-14.

Fourest, E., and Volesky, B., 1997. Alginate Properties and Heavy Metal Biosorption by Marine Algae. Applied Biochemistry and Biotechnology 67, 215-226.

Fu, F., and Wang, Q., 2011. Removal of heavy metal ions from wastewaters: a review. Journal of Environmental Management 92, 407-418.

Gardea-Torresdey, J. L., Becker-Hapak, M. K., Hosea, J. M., and Darnall, D. W., 1990. Effect of chemical modification of algal carboxyl groups on metal ion binding. Environmental Science & Technology 24, 1372-1378.

Gekeler, W., Grill, E., Winnacker, E.-L., and Zenk, M. H., 1988. Algae sequester heavy metals via synthesis of phytochelatin complexes. Archives of Microbiology 150, 197-202.

Gopalapillai, Y., Chakrabarti, C. L., and Lean, D. R. S., 2008. Assessing toxicity of mining effluents: equilibrium- and kinetics-based metal speciation and algal bioassay. Environmental Chemistry 5, 307-315.

Guéguen, C., & Cuss, C. W., 2011. Characterization of aquatic dissolved organic matter by asymmetrical flow field-flow fractionation coupled to UV-Visible diode array and excitation emission matrix fluorescence. Journal of Chromatography A, 1218, 4188-4198.

Helms, J. R., Stubbins, A., Ritchie, J. D., Minor, E. C., Kieber, D. J., Mopper, K., 2008. Absorption spectral slopes and slope ratios as indicators of molecular weight, source, and photobleaching of chromophoric dissolved organic matter. Limnol. Oceanogr. 53, 955-969. doi: 10.4319/lo.2008.53.3.0955.

Hemes, P. J., Bergamaschi, B. A., Eckard, R. S., Spencer, R. G. M., 2009. Fluorescence-based proxies for lignin in freshwater dissolved organic matter. *J. Geophys. Res.* 114:G4. doi: 10.1029/2009JG000938.

Ho, Y. S., and McKay, G., 1998. A comparison of chemisorption kinetic models applied to pollutant removal on various sorbents. Process Safety and Environmental Protection 76, 332-340.

Ho, Y. S., Wase, D. A. J., and Forster, C. F., 1996. Kinetic studies of competitive heavy metal adsorption by sphagnum moss peat. Environmental Technology 17(1): 71-77.

Jaikumar, V., and Ramamurthi, V., 2009. Effect of biosorption parameters kinetics isotherm and thermodynamics for acid green dye biosorption from aqueous solution by brewery waste. International journal of chemistry 1, p 2.

Kadukova, J., and Vircikova, E. 2005. Comparison of differences between copper bioaccumulation and biosorption. Environment international 31, 227-232.

Keller, W., Yan, N. D., Gunn, J. M., and Heneberry, J., 2007. Recovery of acidified lakes: lessons from Sudbury, Ontario, Canada. In Acid Rain-Deposition to Recovery. Springer. pp. 317-322.

Kishore, R., and Schwartzbach, S. D., 1992. Translational control of the synthesis of the *Euglena* light harvesting chlorophyll a/b binding protein of photosystem II. Plant Sci., 85(1), 79-89. doi:10.1016/0168-9452(92)90096-5.

Kizilkaya, B., Turker, G., Akgul, R., and Dogan, F., 2012. Comparative study of biosorption of heavy metals using living green algae *Scenedesmus quadricauda* and *Neochloris pseudoalveolaris*: Equilibrium and kinetics. Journal of Dispersion Science and Technology 33, 410-419.

Koren, L. E., and Hutner, S. H., 1967. High-yield media for photosynthesizing *Euglena gracilis* Z. J Protozool 14.

Kreutzweiser, D., Beall, F., Webster, K., Thompson, D., and Creed, I., 2013. Impacts and prognosis of natural resource development on aquatic biodiversity in Canada's boreal zone 1. Environmental Reviews 21, 227-259.

Kumar, K. S., Dahms, H.-U., Won, E.-J., Lee, J.-S., and Shin, K.-H., 2015. Microalgae-A promising tool for heavy metal remediation. Ecotoxicology and environmental safety 113, 329-352.

Lagergren, S., 1898. About the theory of so-called adsorption of soluble substances. Kungliga Svenska Vetenskapsakademiens Handlingar 24, 1-39.

Li, Y.-R., Wen-Tien, T., Yi-Chyun, H., Meng-Zhi, X., and Jen-Jeng, C., 2014. Comparison of autotrophic and mixotrophic cultivation of green microalgal for biodiesel production. Energy Procedia. 52: 371-376. doi: 10.1016/j.egypro.2014.07.088.

Liu, Y., Cao, Q., Luo, F., and Chen, J., 2009. Biosorption of $Cd\ 2+$, $Cu\ 2+$, $Ni\ 2+$ and $Zn\ 2+$ ions from aqueous solutions by pretreated biomass of brown algae. Journal of Hazardous Materials 163, 931-938.

Lu, C. J., Benner, R., Fichot, C. G., Fukuda, H., Yamashita, Y., Ogawa, H., 2016. Sources and transformations of dissolved lignin phenols and chromophoric dissolved organic matter in Otsuchi Bay, Japan. *Frontiers in Marine Science.* 3, 85. doi:10.3389/fmars.2016.00085.

Mandavi, H., Ulrich, A. C., and Liu, Y., 2012. Metal removal from oil sands tailings pond water by indigenous microalga. Chemosphere 89, 350-354.

Malik, A., 2004. Metal bioremediation through growing cells. Environment International 30, 261-278.

Mangal, V., Stock, N. L., and Guéguen, C., 2016. Molecular characterization of phytoplankton dissolved organic matter (DOM) and sulfur components using high resolution Orbitrap mass spectrometry. Anal Bioanal Chem 408, 1891-1900.

Matsuda, F., Hayashi, M., and Kondo, A., 2011. Comparative profiling analysis of central metabolites in *Euglena gracilis* under various cultivation conditions. *Biosci. Biotechnol. Biochem,* 75(11), 2253-2256. doi:10.1271/bbb.110482.

Medeiros, P., Seidel, M., Powers, L., Dittmar, T., Hansell, D., Miller, W. (2015). Dissolved organic matter composition and photochemical transformations in the northern North Pacific Ocean. *Geophys. Res. Lett.* 42(3), 863-870. doi:10.1002/2014GL062663.

Mendoza-Cozatl, D. G., Rangel-Gonzalez, E., and Moreno-Sanchez, R, 2006. Simultaneous $Cd2+$, $Zn2+$, and $Pb2+$ uptake and accumulation by photosynthetic *Euglena gracilis*. Archives of environmental contamination and toxicology 51, 521-528.

Michalak, I., Chojnacka, K., and Witek-Krowiak, A., 2013. State of the art for the biosorption process-a review. Applied biochemistry and biotechnology 170, 1389-1416.

Nestle, N., 2002. NMR studies on heavy metal immobilization in biosorbents and mineral matrices. Reviews in Environmental Science & Biotechnology 1, 215-225.

Ohno, T., and Ohno, P. E., 2013. Influence of heteroatom pre-selection on the molecular formula assignment of soil organic matter components determined by ultrahigh resolution mass spectrometry. Anal Bioanal Chem 405, 3299-3306.

Olaveson, M. M., and Nalewajko, C., 2000. Effects of acidity on the growth of two *Euglena* species. Hydrobiologia 433, 39-56.

O'Neill, E. C., Trick, M., Hill, L., Rejzek, M., Dusi, R. G., Hamilton, C. J., and Field, R. A., 2015. The transcriptome of *Euglena gracilis* reveals unexpected metabolic capabilities for carbohydrate and natural product biochemistry. *Mol Biosyst*, 11(10), 2808-2820. doi:10.1039/c5mb00319a.

Opsahl, S., Benner, R., 1998. Photochemical reactivity of dissolved lignin in river and ocean waters. *Limnol. Oceanogr.* 43, 1297-1304. doi:10.4319/10.1998.43.6.1297.

Plazinski, W., 2013. Binding of heavy metals by algal biosorbents. Theoretical models of kinetics, equilibria and thermodynamics. Advances in colloid and interface science 197, 58-67.

Rao, S. P., Kalyani, S., Suresh Reddy, K. V. N., and Krishnaiah, A., 2005. Comparison of biosorption of nickel (II) and copper (II) ions from aqueous solution by Sphaeroplea algae and acid treated Sphaeroplea algae. Separation science and technology 40, 3149-3165.

Rodriguez-Zavala, J. S., Garcia-Garcia, J. D., Ortiz-Cruz, M. A., and Moreno-Sanchez, R. 2007. Molecular mechanisms of resistance to heavy metals in the protist *Euglena gracilis*. Journal of Environmental Science and Health Part A 42, 1365-1378.

Rosenberg, A., and Pecker, M., 1964. Lipid alterations in *Euglena gracilis* cells during light-induced greening. *Biochem.* 3(2), 254-258. doi: 10.1021/bi00890a019.

Šantek, B., Friehs, K., Lotz, M., and Flaschel, E., 2012. Production of paramylon, a β-1, 3-glucan, by heterotrophic growth of *Euglena gracilis* on potato liquor in fed-batch and repeated-batch mode of cultivation. Engineering in Life Sciences, 12(1), 89-94. doi:10.1002/elsc.201100025

Schimpf, M. E., Caldwell, K., and Giddings, J. C. (2000). *Field-Flow Fractionation Handbook*: Wiley.

Schwartzbach, S. D., and Shigeoka, S., 2017. *Euglena*: Biochemistry, Cell and Molecular Biology. *Adv. Exp. Med. Biol.*, 979. doi:10.1007/978-3-319-54910-1.

Spencer, R., Stubbins, A., Hernes, P., Baker, A., Mopper, K., Aufdenkampe, A., Dyda, R., Mwamba, V., Mangangu, A., Wabakanghanzi, J., Six, J., 2009. Photochemical degradation of dissolved organic matter and dissolved lignin phenols from the Congo River. *J. Geophys. Res.* 114. doi:10.1029/2009JG000968.

Tien, C.-J., Sigee, D. C., and White, K. N., 2005. Copper adsorption kinetics of cultured algal cells and freshwater phytoplankton with emphasis on cell surface characteristics. Journal of Applied Phycology 17, 379-389.

Volesky, B., 2001. Detoxification of metal-bearing effluents: biosorption for the next century. Hydrometallurgy 59, 203-216.

Volesky, B., 2003. Sorption and biosorption. BV Sorbex. Montreal, QC.

Wang, J., and Chen, C., 2009. Biosorbents for heavy metals removal and their future. Biotechnology advances 27, 195-226.

Winter, C., Winter, M., and Pohl, P., 1994. Cadmium adsorption by non-living biomass of the semi-macroscopic brown alga, *Ectocarpus siliculosus*, grown in axenic mass culture and localisation of the adsorbed Cd by transmission electron microscopy. Journal of Applied Phycology 6, 479-487.

The invention claimed is:

1. A method of binding a target metal, comprising:
contacting a solution containing
i) a target metal with
ii) an encapsulated dried *Euglena* biomass or a fraction thereof;
an encapsulated wet *Euglena* biomass, or a fraction thereof; or
an encapsulated exudate of a culture of algal flagellate or a fraction thereof;
to form a complex between the target metal, and the encapsulated dried *Euglena* biomass or the fraction thereof, the encapsulated wet *Euglena* biomass or the fraction thereof, or the encapsulated exudate or the fraction thereof;
wherein the method further comprises separating the complex from the solution; and
wherein the separation comprises contacting the complex with a microorganism or microorganism material to sequester the complex.

2. The method of claim 1, wherein the algal flagellate is a Chlamydomonadaceae, a Cryptophyceae, a Dinoflagellate, an Euglenaceae, a Haptophyta, or mixtures thereof, and/or the algal flagellate is a *Chlamydomonas* sp., a *Cryptophyta* sp., a *Dinophyta* sp., an *Euglena* sp., or mixtures thereof, and/or the algal flagellate is *Chlamydomonas reinhardtii*, *Euglena gracilis*, *Euglena mutabilis*, or combinations thereof, and/or the algal flagellate is *Euglena gracilis*.

3. The method of claim 1, wherein the metal comprises silver, gold, aluminum, arsenic, barium, beryllium, bismuth, calcium, cadmium, cobalt, chromium, copper, iron, potassium, lithium, magnesium, manganese, molybdenum, sodium, nickel, phosphorus, platinum, palladium, lead, antimony, selenium, tin, strontium, thallium, titanium, uranium, vanadium, tungsten, yttrium, zinc, scandium, lanthanum, a rare earth element, or a divalent transition metal.

4. The method of claim 1, wherein the solution is water, and/or wastewater, and/or domestic wastewater, urban wastewater, industrial wastewater or combinations thereof, and/or effluent from a mining operation, and wherein the method is for remediation of water or wastewater having one or more metals to be removed, and/or for remediation of mining process water having the metals to be removed and the water is mining process water.

5. The method of claim 1, wherein the encapsulated exudate of a culture of algal flagellate, the encapsulated dried *Euglena* biomass, or the encapsulated wet *Euglena* biomass, is sphericated or gelificated, and/or wherein the encapsulated exudate of a culture of algal flagellate comprises glutathione, metallothioneins, phytochelatins, polyphosphates, polysaccharides, or combinations thereof.

6. The method of claim 5, wherein the spherification or gelification process comprises encapsulating the exudate of a culture of algal flagellate, dried *Euglena* biomass, or the encapsulated wet *Euglena* biomass in an immobilizing matrix, and/or encapsulating the exudate in an immobilizing matrix comprising a resin, a polymer plastic or diffusive gradient in thin films (DGT), and/or encapsulating the exudate in an immobilizing matrix comprising agar, agarose, alginate, carrageenan, cellulose, chitosan, polystyrene, polyurethane, polyvinyl, or combinations thereof, and/or encapsulating the exudate in an immobilizing matrix comprising sodium alginate.

7. The method of claim 1, wherein the encapsulated exudate of a culture of algal flagellate, the encapsulated dried *Euglena* biomass, or the encapsulated wet *Euglena* biomass are housed in a containment element, and/or the encapsulated exudates are housed in a containment element comprises a semi-permeable membrane, and/or the encapsulated exudates are housed in a containment element comprises a semi-permeable membrane comprises integral asymmetric membrane or thin film composite membrane.

8. The method of claim 1, wherein amount or type of metal sequestered per weight of active material of the encapsulated dried *Euglena* biomass is modified by post-harvest treatment, and/or wherein amount or type of metal sequestered per weight of active material of the encapsulated dried *Euglena* biomass is modified by post-harvest treatment comprises heating the biomass or fraction thereof, prior to spherification or gelification.

9. The method of claim 8, wherein the encapsulated exudate of a culture of algal flagellate, the encapsulated wet *Euglena* biomass, the encapsulated dried *Euglena* biomass, and/or the post-harvest treated encapsulated dried *Euglena* biomass comprising different metal binding selectivities are housed in a plurality of columns, the columns arranged to produce a column effluent, and/or columns arranged in a series comprising at least a first column, a second column and a third column, and the solution flows through the columns sequentially to produce the column effluent, and/or columns arranged in a series comprising a first column selectively binds to copper, a second column selectively binds to silver, and a third column selectively binds to gold.

10. The method of claim 1, further comprising desorbing the target metal, and/or desorbing the target metal comprising contacting the complex with a desorbent, and/or wherein the target metal is a precious metal, and/or the target metal is gold, silver, platinum, or palladium, and/or wherein after desorbing the target metal from the complex, the encapsulated exudate of a culture of algal flagellate or a fraction thereof, the encapsulated dried *Euglena* biomass or a fraction thereof, or the encapsulated wet *Euglena* biomass or a fraction thereof, contacts a second solution containing a target metal.

11. The method of claim 10, wherein the desorbent comprises an acidic or basic solution, and/or one or more of hydrochloric acid, nitric acid, sulphuric acid and citric acid, and/or one or more of sodium hydroxide, sodium carbonate, and sodium bicarbonate, and/or potassium cyanide or thiourea.

12. The method of claim 1, wherein the encapsulated dried *Euglena* biomass or the fraction thereof, is an encapsulated non-living dried *Euglena* biomass or the fraction thereof.

13. The method of claim 1, wherein the encapsulated wet *Euglena* biomass or the fraction thereof, is an encapsulated non-living wet *Euglena* biomass or the fraction thereof.

14. The method of claim 1, wherein the encapsulated exudate or the fraction thereof is an encapsulated non-living exudate or the fraction thereof.

15. A biosorbent element comprising a substrate carrying encapsulated non-living dried *Euglena* biomass, encapsulated non-living wet *Euglena* biomass, or encapsulated non-living exudates of *Euglena*, or a fraction thereof, in sufficient quantity to adsorb metals from solution passing therethrough.

16. The biosorbent element of claim 15, wherein the biosorbent element is a biosorbent diffusive gradient across a plurality of thin films.

17. The biosorbent element of claim 15, wherein the biosorbent element binds metals comprise silver, gold, aluminum, arsenic, barium, beryllium, bismuth, calcium, cadmium, cobalt, chromium, copper, iron, potassium, lithium, magnesium, manganese, molybdenum, sodium, nickel, phosphorus, platinum, palladium, lead, antimony, selenium, tin, strontium, thallium, titanium, uranium, vanadium, tungsten, yttrium, zinc, scandium, lanthanum, rare earth elements and divalent transition metals.

18. The biosorbent element of claim 15, wherein the biosorbent element is for use in remediation of wastewater having the metals to be adsorbed, and/or the biosorbent element is for use in remediation of wastewater before the wastewater contacts activated carbon.

19. The biosorbent element of claim 18, wherein the wastewater is domestic wastewater, urban wastewater, industrial wastewater or combinations thereof, and/or wherein the wastewater is industrial wastewater comprising effluent from a mining operation.

20. The biosorbent element of claim 15, wherein the encapsulated dried *Euglena* biomass, or a fraction thereof, or the encapsulated wet *Euglena* biomass, or a fraction thereof, or the encapsulated exudates of a culture of *Euglena*, or a fraction thereof, comprises glutathione, metallothioneins, phytochelatins, polyphosphates, polysaccharides, or combinations thereof, and/or is contained in a dialysis container or dialysis bag, and/or is embedded in a diffusive gradient in a plurality of thin films, and/or is embedded in a diffusion gradient technology (DGT).

21. The biosorbent element of claim 15, wherein the encapsulated dried *Euglena* biomass, or a fraction thereof, or the encapsulated wet *Euglena* biomass, or a fraction thereof, or the encapsulated exudates of a culture of *Euglena*, or a fraction thereof, is spherical and/or gelatinous, and/or wherein the biosorbent element comprises an immobilizing matrix, and/or wherein the biosorbent element comprises immobilizing matrix comprising a resin or a polymer plastic, and/or wherein the biosorbent element comprises immobilizing matrix comprising agar, agarose, alginate, carrageenan, cellulose, chitosan, polystyrene, polyurethane, polyvinyl, or combinations thereof, and/or wherein the immobilizing matrix comprises sodium alginate.

* * * * *